United States Patent
Boudreaux

(10) Patent No.: US 12,239,404 B2
(45) Date of Patent: Mar. 4, 2025

(54) TORQUE-BASED TRANSITION BETWEEN OPERATING GEARS

(71) Applicant: Cilag GmbH International, Zug (CH)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 985 days.

(21) Appl. No.: 17/137,852

(22) Filed: Dec. 30, 2020

(65) Prior Publication Data

US 2022/0202514 A1 Jun. 30, 2022

(51) Int. Cl.
*A61B 17/32* (2006.01)
*A61B 17/29* (2006.01)
(Continued)

(52) U.S. Cl.
CPC .............. *A61B 34/37* (2016.02); *A61B 17/29* (2013.01); *A61B 17/2909* (2013.01); *B25J 9/04* (2013.01);
(Continued)

(58) Field of Classification Search
CPC . A61B 34/37; A61B 2017/2923; A61B 34/30; A61B 2034/302; A61B 2034/305; A61B 2034/303; A61B 17/068; A61B 17/29; A61B 2017/2912–2924; B25J 9/04; B25J 9/1035; B25J 9/1633;
(Continued)

(56) References Cited

U.S. PATENT DOCUMENTS 1,752,937 A * 4/1930 Barnett ................... F16D 41/22
74/333
2,621,531 A * 12/1952 Friedrich ................. B23Q 5/12
74/333
(Continued)

FOREIGN PATENT DOCUMENTS

EP 3192461 A1 * 7/2017 ....... A61B 17/00234
KR 20120068597 A 6/2012

OTHER PUBLICATIONS

"Gear" [https://en.wikipedia.org/wiki/Gear, dated Nov. 6, 2015]. (Year: 2015).*
(Continued)

*Primary Examiner* — Brooke Labranche
*Assistant Examiner* — Mitchell Brian Hoag

(57) ABSTRACT

A surgical tool configured to receive rotary inputs from a robotic surgical system. The surgical tool comprises a distal end effector comprising jaws for clamping tissue therebetween, an intermediate shaft portion coupled to the distal end effector, and a proximal housing coupled to the intermediate shaft portion. The proximal housing comprises an arrangement of rotary drives comprising a first rotary drive. The first rotary drive comprises an input shaft configured to receive a rotary input from the robotic surgical system, a transition nut slidably positioned on the input shaft, and an output gear. The first rotary drive further comprises a high-speed gear configured to selectively drive the output gear, a high-torque gear configured to selectively drive the output gear, and a spring arrangement configured to bias the transition nut along the input shaft from a high-speed operating state to a high-torque operating state upon obtaining a threshold torque.

20 Claims, 31 Drawing Sheets

(51) Int. Cl.
  *A61B 34/37*   (2016.01)
  *B25J 9/04*    (2006.01)
  *B25J 9/10*    (2006.01)
  *B25J 9/16*    (2006.01)
  *B25J 15/02*   (2006.01)
  *B25J 18/04*   (2006.01)
  *A61B 17/068*  (2006.01)
  *A61B 34/30*   (2016.01)

(52) U.S. Cl.
  CPC .......... *B25J 9/1035* (2013.01); *B25J 9/1633* (2013.01); *B25J 15/0213* (2013.01); *B25J 18/04* (2013.01); *A61B 17/068* (2013.01); *A61B 2017/2923* (2013.01); *A61B 2017/2943* (2013.01); *A61B 2034/304* (2016.02); *A61B 2034/305* (2016.02); *A61B 2034/306* (2016.02)

(58) Field of Classification Search
  CPC ....... B25J 15/0213; B25J 18/04; B25B 23/14; B25B 23/141; B25D 16/003; B25D 2250/165; F61D 7/046; F61D 43/2022; F61D 43/2024; F61D 43/2026; F61D 43/00; F16D 41/185
  USPC ....... 74/490.01, 665 GA, 665 K, 665 P, 333; 173/216, 176, 178
  See application file for complete search history.

(56) References Cited

U.S. PATENT DOCUMENTS

| | | | |
|---|---|---|---|
| 2,706,544 A * | 4/1955 | Schuman ................. | B23Q 5/10 192/84.1 |
| 4,114,464 A * | 9/1978 | Schubert .............. | B25J 15/0213 623/64 |
| 4,785,180 A | 11/1988 | Dietrich et al. | |
| 4,823,885 A * | 4/1989 | Okumura ................ | B25F 5/001 173/217 |
| 5,021,969 A | 6/1991 | Okamura et al. | |
| 5,259,259 A * | 11/1993 | Inokuchi ................. | B25F 5/001 192/48.92 |
| 5,403,312 A | 4/1995 | Yates et al. | |
| 5,688,270 A | 11/1997 | Yates et al. | |
| 5,709,680 A | 1/1998 | Yates et al. | |
| 5,762,458 A | 6/1998 | Wang et al. | |
| 5,855,553 A | 1/1999 | Tajima et al. | |
| 5,855,583 A | 1/1999 | Wang et al. | |
| 5,878,193 A | 3/1999 | Wang et al. | |
| 6,120,433 A | 9/2000 | Mizuno et al. | |
| 6,132,368 A | 10/2000 | Cooper | |
| 6,587,750 B2 | 7/2003 | Gerbi et al. | |
| 6,679,406 B2 | 1/2004 | Sakai et al. | |
| 6,804,012 B2 | 10/2004 | Gombert | |
| 6,810,281 B2 | 10/2004 | Brock et al. | |
| 6,951,535 B2 | 10/2005 | Ghodoussi et al. | |
| 7,000,818 B2 | 2/2006 | Shelton, IV et al. | |
| 7,422,139 B2 | 9/2008 | Shelton, IV et al. | |
| 7,464,849 B2 | 12/2008 | Shelton, IV et al. | |
| 7,516,675 B2 | 4/2009 | Kurtz et al. | |
| 7,524,320 B2 | 4/2009 | Tierney et al. | |
| 7,607,557 B2 | 10/2009 | Shelton, IV et al. | |
| 7,621,730 B2 | 11/2009 | Del Rio et al. | |
| 7,670,334 B2 | 3/2010 | Hueil et al. | |
| 7,673,783 B2 | 3/2010 | Morgan et al. | |
| 7,681,661 B2 | 3/2010 | Sakai et al. | |
| 7,747,311 B2 | 6/2010 | Quaid, III | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 7,996,110 B2 | 8/2011 | Lipow et al. | |
| 8,063,883 B2 | 11/2011 | Senft et al. | |
| 8,079,950 B2 | 12/2011 | Stern et al. | |
| 8,210,411 B2 | 7/2012 | Yates et al. | |
| 8,215,533 B2 | 7/2012 | Viola et al. | |
| 8,220,688 B2 | 7/2012 | Laurent et al. | |
| 8,224,484 B2 | 7/2012 | Swarup et al. | |
| 8,308,040 B2 | 11/2012 | Huang et al. | |
| 8,393,514 B2 | 3/2013 | Shelton, IV et al. | |
| 8,523,043 B2 | 9/2013 | Ullrich et al. | |
| 8,561,870 B2 | 10/2013 | Baxter, III et al. | |
| 8,608,045 B2 | 12/2013 | Smith et al. | |
| 8,684,253 B2 | 4/2014 | Giordano et al. | |
| 8,716,973 B1 | 5/2014 | Lammertse | |
| 8,733,613 B2 | 5/2014 | Huitema et al. | |
| 8,888,789 B2 | 11/2014 | Prisco et al. | |
| 8,979,872 B2 | 3/2015 | Harris et al. | |
| 8,996,173 B2 | 3/2015 | Itkowitz et al. | |
| 9,050,083 B2 | 6/2015 | Yates et al. | |
| 9,055,961 B2 | 6/2015 | Manzo et al. | |
| 9,072,535 B2 | 7/2015 | Shelton, IV et al. | |
| 9,101,358 B2 | 8/2015 | Kerr et al. | |
| 9,161,817 B2 | 10/2015 | Olson et al. | |
| 9,186,046 B2 | 11/2015 | Ramamurthy et al. | |
| 9,274,047 B2 | 3/2016 | Velten et al. | |
| 9,345,481 B2 | 5/2016 | Hall et al. | |
| 9,500,473 B2 | 11/2016 | Ramamurthy et al. | |
| 9,801,679 B2 | 10/2017 | Trees et al. | |
| 9,808,246 B2 | 11/2017 | Shelton, IV et al. | |
| 9,812,035 B2 | 11/2017 | Stuart et al. | |
| 9,827,059 B2 | 11/2017 | Robinson et al. | |
| 9,855,060 B2 | 1/2018 | Ardel et al. | |
| 10,052,766 B2 | 8/2018 | Shirakyan et al. | |
| 10,159,506 B2 | 12/2018 | Boudreaux et al. | |
| 10,198,086 B2 | 2/2019 | Parazynski et al. | |
| 10,398,434 B2 | 9/2019 | Shelton, IV et al. | |
| 10,398,517 B2 | 9/2019 | Eckert et al. | |
| 10,441,281 B2 | 10/2019 | Shelton, IV et al. | |
| 10,441,370 B2 | 10/2019 | Millman et al. | |
| 10,470,830 B2 | 11/2019 | Hill et al. | |
| 10,485,527 B2 | 11/2019 | Shelton, IV et al. | |
| 10,485,617 B2 | 11/2019 | Crawford et al. | |
| 10,499,996 B2 | 12/2019 | de Almeida Barreto | |
| 10,507,068 B2 | 12/2019 | Kopp et al. | |
| 10,548,679 B2 | 2/2020 | Carlson et al. | |
| 10,610,313 B2 | 4/2020 | Bailey et al. | |
| 10,653,486 B2 | 5/2020 | Ishihara et al. | |
| 10,660,719 B2 | 5/2020 | De Mathelin et al. | |
| 10,792,034 B2 | 10/2020 | Scheib et al. | |
| 10,806,478 B2 | 10/2020 | Boudreaux et al. | |
| 10,835,332 B2 | 11/2020 | Manzo et al. | |
| 10,925,598 B2 | 2/2021 | Scheib et al. | |
| 10,932,772 B2 | 3/2021 | Shelton, IV et al. | |
| 10,993,729 B1 | 5/2021 | Aman et al. | |
| 11,000,270 B2 | 5/2021 | Scheib et al. | |
| 11,013,563 B2 | 5/2021 | Shelton, IV et al. | |
| 11,045,175 B2 | 6/2021 | Coelho, Jr. et al. | |
| 11,076,923 B1 | 8/2021 | Adelman | |
| 11,207,064 B2 * | 12/2021 | Shelton, IV ........... | A61B 34/37 |
| 11,213,361 B2 | 1/2022 | Denlinger et al. | |
| 11,259,793 B2 | 3/2022 | Scheib et al. | |
| 11,284,957 B2 | 3/2022 | Denlinger et al. | |
| 11,304,692 B2 | 4/2022 | Scheib | |
| 11,369,366 B2 | 6/2022 | Scheib et al. | |
| 11,419,604 B2 | 8/2022 | Scheib et al. | |
| 11,432,885 B2 | 9/2022 | Shelton, IV et al. | |
| 11,471,151 B2 | 10/2022 | Scheib et al. | |
| 11,471,229 B2 | 10/2022 | Denlinger et al. | |
| 11,490,981 B2 | 11/2022 | Denlinger et al. | |
| 11,559,298 B2 | 1/2023 | Scheib et al. | |
| 11,564,678 B2 | 1/2023 | Scheib et al. | |
| 11,571,205 B2 | 2/2023 | Scheib et al. | |
| 11,583,350 B2 | 2/2023 | Denlinger et al. | |
| 11,666,401 B2 | 6/2023 | Denlinger et al. | |
| 11,690,690 B2 | 7/2023 | Denlinger et al. | |
| 11,701,190 B2 | 7/2023 | Denlinger et al. | |
| 11,754,712 B2 | 9/2023 | Scheib | |
| 2003/0109857 A1 | 6/2003 | Sanchez et al. | |
| 2004/0128026 A1 | 7/2004 | Harris et al. | |
| 2004/0221674 A1 | 11/2004 | Kornelson | |
| 2004/0243147 A1 | 12/2004 | Lipow | |
| 2007/0021738 A1 | 1/2007 | Hasser et al. | |
| 2007/0144298 A1 | 6/2007 | Miller | |
| 2007/0175955 A1 | 8/2007 | Shelton et al. | |

(56) References Cited

U.S. PATENT DOCUMENTS

| | | |
|---|---|---|
| 2008/0001919 A1 | 1/2008 | Pascucci |
| 2010/0262162 A1 | 10/2010 | Omori |
| 2010/0286480 A1 | 11/2010 | Peine et al. |
| 2010/0302017 A1 | 12/2010 | Guglielmo |
| 2011/0295242 A1 | 12/2011 | Spivey et al. |
| 2012/0143353 A1 | 6/2012 | Kishi |
| 2012/0154564 A1 | 6/2012 | Hoffman et al. |
| 2012/0158011 A1 | 6/2012 | Sandhu et al. |
| 2012/0221145 A1 | 8/2012 | Ogawa |
| 2012/0292369 A1 | 11/2012 | Munro, III et al. |
| 2013/0087355 A1 | 4/2013 | Oomori et al. |
| 2013/0238048 A1 | 9/2013 | Almendinger et al. |
| 2014/0001231 A1 | 1/2014 | Shelton, IV et al. |
| 2014/0005661 A1* | 1/2014 | Shelton, IV ....... A61B 18/1445 606/41 |
| 2014/0005676 A1* | 1/2014 | Shelton, IV ......... A61B 17/062 606/130 |
| 2014/0102741 A1 | 4/2014 | Sekino et al. |
| 2014/0160015 A1 | 6/2014 | Ogawa et al. |
| 2014/0263552 A1 | 9/2014 | Hall et al. |
| 2014/0343566 A1 | 11/2014 | Wenderow et al. |
| 2015/0053739 A1* | 2/2015 | Morgan ............... A61B 17/068 227/175.1 |
| 2015/0245874 A1 | 9/2015 | Hatta |
| 2015/0366624 A1 | 12/2015 | Kostrzewski et al. |
| 2016/0000449 A1 | 1/2016 | Aman et al. |
| 2016/0353969 A1 | 12/2016 | Kikuchi |
| 2017/0021738 A1 | 1/2017 | Brochhaus |
| 2017/0055819 A1 | 3/2017 | Hansen et al. |
| 2017/0224428 A1 | 8/2017 | Kopp |
| 2017/0239005 A1* | 8/2017 | Cohen .................. B25J 18/025 |
| 2017/0251900 A1 | 9/2017 | Hansen et al. |
| 2018/0049812 A1* | 2/2018 | Yates .................... A61B 46/10 |
| 2018/0049835 A1* | 2/2018 | Shelton, IV ........... A61B 34/32 |
| 2018/0147019 A1 | 5/2018 | Farritor et al. |
| 2019/0041891 A1 | 2/2019 | Parazynski |
| 2019/0200905 A1 | 7/2019 | Shelton, IV et al. |
| 2019/0201142 A1 | 7/2019 | Shelton, IV et al. |
| 2019/0307524 A1 | 10/2019 | Popovic |
| 2020/0015899 A1 | 1/2020 | Scheib et al. |
| 2020/0015900 A1 | 1/2020 | Scheib et al. |
| 2020/0015904 A1 | 1/2020 | Scheib et al. |
| 2020/0015907 A1 | 1/2020 | Scheib |
| 2020/0015917 A1 | 1/2020 | Cavalier et al. |
| 2020/0015924 A1 | 1/2020 | Scheib et al. |
| 2020/0138534 A1 | 5/2020 | Garcia Kilroy et al. |
| 2020/0289205 A1 | 9/2020 | Scheib et al. |
| 2020/0289216 A1 | 9/2020 | Denlinger et al. |
| 2020/0289228 A1 | 9/2020 | Denlinger et al. |
| 2021/0059777 A1 | 3/2021 | Overmyer et al. |
| 2021/0259683 A1* | 8/2021 | Zemlok ............... A61B 17/1114 |
| 2022/0039895 A1* | 2/2022 | Adams ..................... B25J 9/102 |
| 2022/0117461 A1 | 4/2022 | Shvalb et al. |
| 2022/0202437 A1 | 6/2022 | Overmyer et al. |
| 2022/0202517 A1 | 6/2022 | Overmyer et al. |
| 2022/0203519 A1 | 6/2022 | Overmyer et al. |

OTHER PUBLICATIONS

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Kurata, et al., "Time-of-flight Near-infrared Spectroscopy for Nondestructive Measurement of Internal Quality in Grapefruit," Journal, May 2013, pp. 225-228, vol. 138, Issue 3, Journal of the American Society for Horticultural Science, Japan.

* cited by examiner

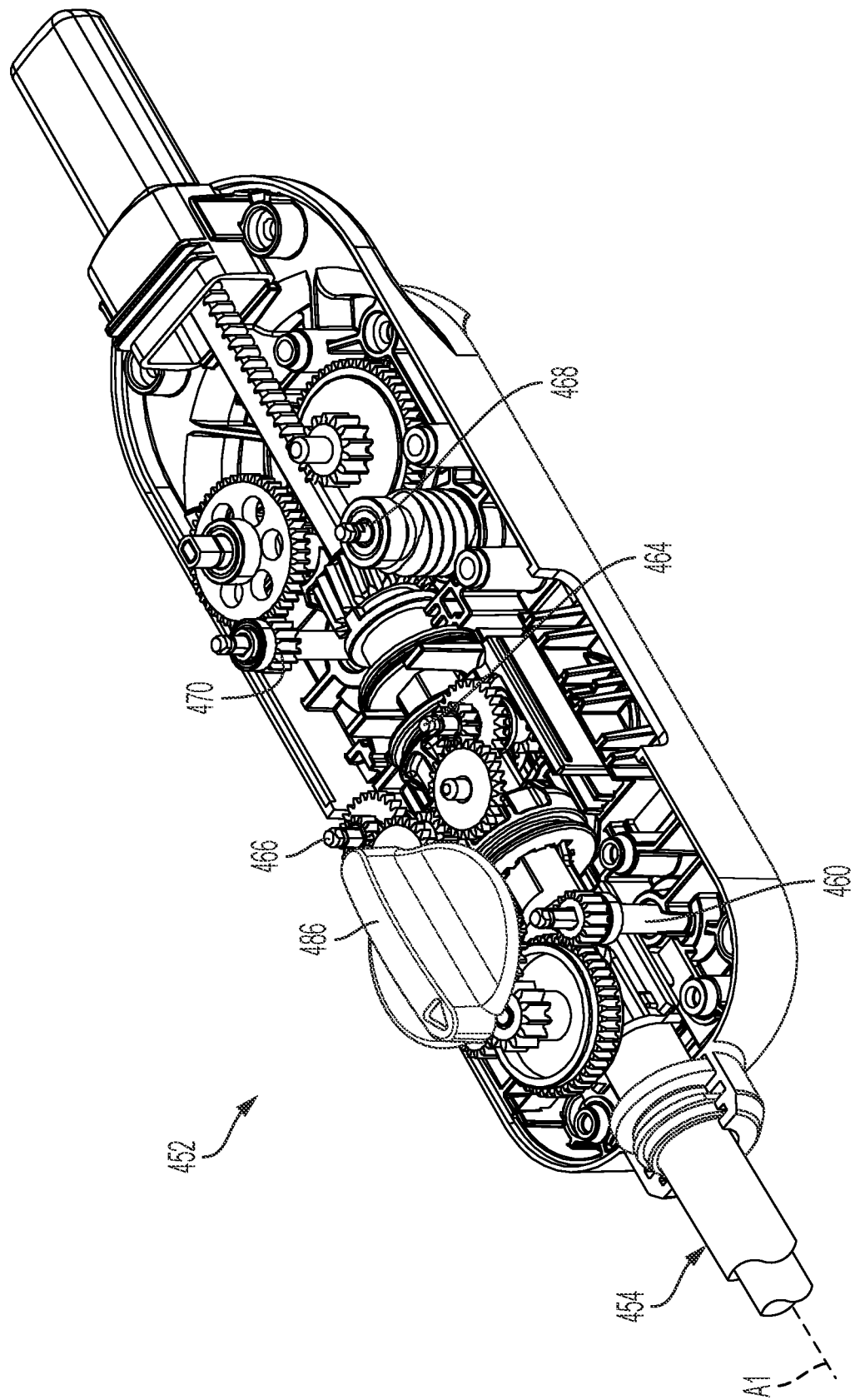

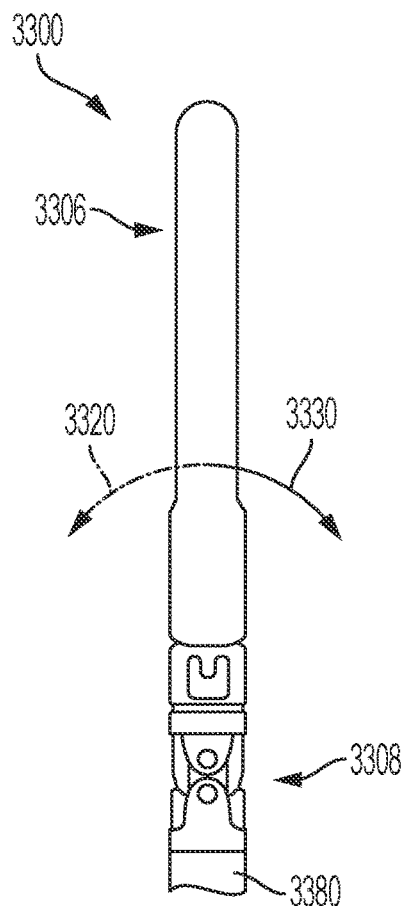
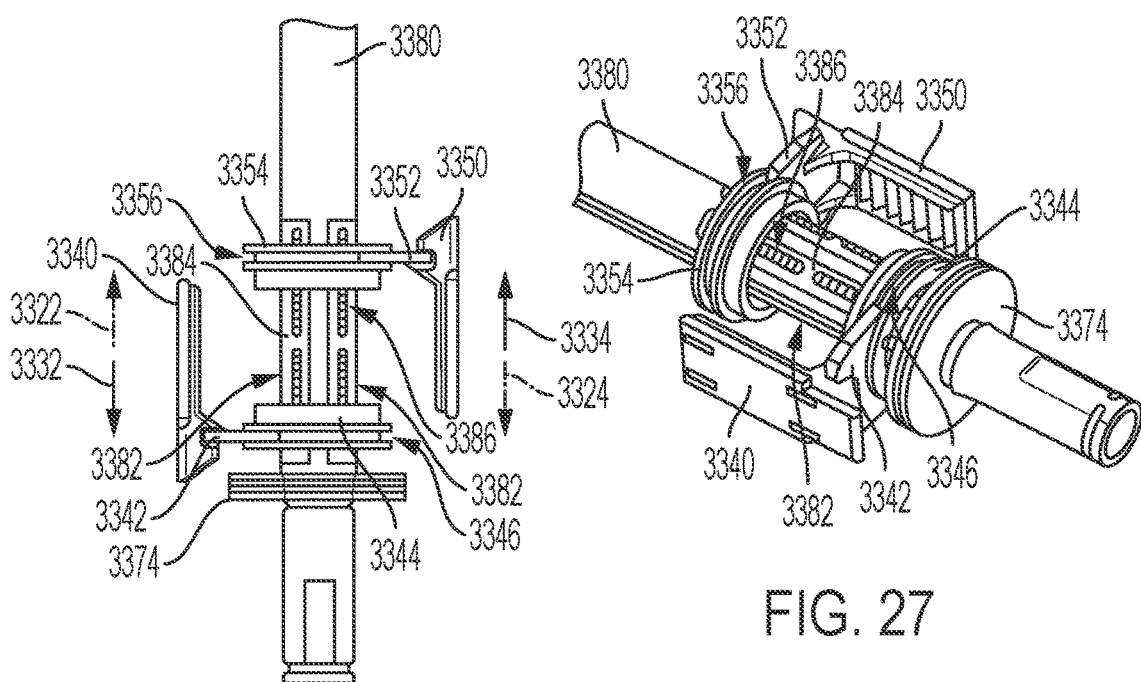
FIG. 26
FIG. 27

TORQUE-BASED TRANSITION BETWEEN OPERATING GEARS

BACKGROUND

The present disclosure relates to robotic surgical systems. Robotic surgical systems can include a central control unit, a surgeon's command console, and a robot having one or more robotic arms. Robotic tools can be releasably mounted to the robotic arm(s). The number and type of robotic tools can depend on the type of surgical procedure. In certain instances, robotic surgical systems can be used in connection with one or more displays and/or one or more handheld surgical instruments during a surgical procedure.

SUMMARY

In one aspect, the present disclosure provides a surgical tool configured to receive rotary inputs from a robotic surgical system. The surgical tool comprises a distal end effector comprising jaws for clamping tissue therebetween, an intermediate shaft portion coupled to the distal end effector, and a proximal housing coupled to the intermediate shaft portion. The proximal housing comprises an arrangement of rotary drives comprising a first rotary drive. The first rotary drive comprises an input shaft configured to receive a rotary input from the robotic surgical system, a transition nut slidably positioned on the input shaft, and an output gear. The first rotary drive further comprises a high-speed gear configured to selectively drive the output gear, a high-torque gear configured to selectively drive the output gear, and a spring arrangement configured to bias the transition nut along the input shaft from a high-speed operating state, in which the transition nut is in driving engagement with the high-speed gear, to a high-torque operating state, in which the transition nut is in driving engagement with the high-torque gear upon obtaining a threshold torque.

In another aspect, the present disclosure provides a surgical tool for a robotic surgical system. The surgical tool comprises a distal end effector comprising jaws for clamping tissue therebetween, an intermediate shaft portion coupled to the distal end effector, and a proximal housing coupled to the intermediate shaft portion. The proximal housing comprises an input shaft configured to receive a rotary input from the robotic surgical system, a transition nut slidably positioned on the input shaft, and an output gear. The proximal housing further comprises a first rotary drive configured to selectively drive the output gear, a second rotary drive configured to selectively drive the output gear, and a spring arrangement configured to bias the transition nut along the input shaft to couple the input shaft with either the first rotary drive or the second rotary drive based on a threshold torque applied to the transition nut.

In another aspect, the present disclosure provides a rotary drive system for rotating a drive screw in a robotic surgical tool. The rotary drive system comprises an input shaft configured to receive a rotary input from a robotic surgical system, a transition nut slidably positioned on the input shaft, and an output gear drivingly coupled to an output shaft. The rotary drive system further comprises a first rotary drive configured to selectively drive the output gear, a second rotary drive configured to selectively drive the output gear, and a spring arrangement configured to bias the transition nut along the input shaft into engagement with either the first rotary drive or the second rotary drive based on a threshold torque applied to the transition nut.

FIGURES

The novel features of the various aspects are set forth with particularity in the appended claims. The described aspects, however, both as to organization and methods of operation, may be best understood by reference to the following description, taken in conjunction with the accompanying drawings in which:

FIG. 6A is a perspective, detail view of a portion of the surgical stapling tool of FIG. 6 depicting a proximal tool base and rotary drives housed therein, with certain components removed from the proximal tool base for clarity, in accordance with at least one aspect of the present disclosure.

FIG. 26 is an elevation view of portions of a robotic surgical tool including an internal shaft, an articulation joint, a surgical end effector, and an articulation system including articulation yokes, in accordance with at least one aspect of the present disclosure.

FIG. 27 is a perspective view of a proximal portion of the articulation system including the articulation yokes and a portion of the internal shaft of the robotic surgical tool of FIG. 26, in accordance with at least one aspect of the present disclosure.

FIGS. 30A-D are elevation views of a visual display for a surgical imaging system depicting portions of a robotic surgical tool during a surgical operation, the views depicting a process to convey information to a clinician with an end effector overlay feature in the visual display, in accordance with at least one aspect of the present disclosure.

Figure 31:
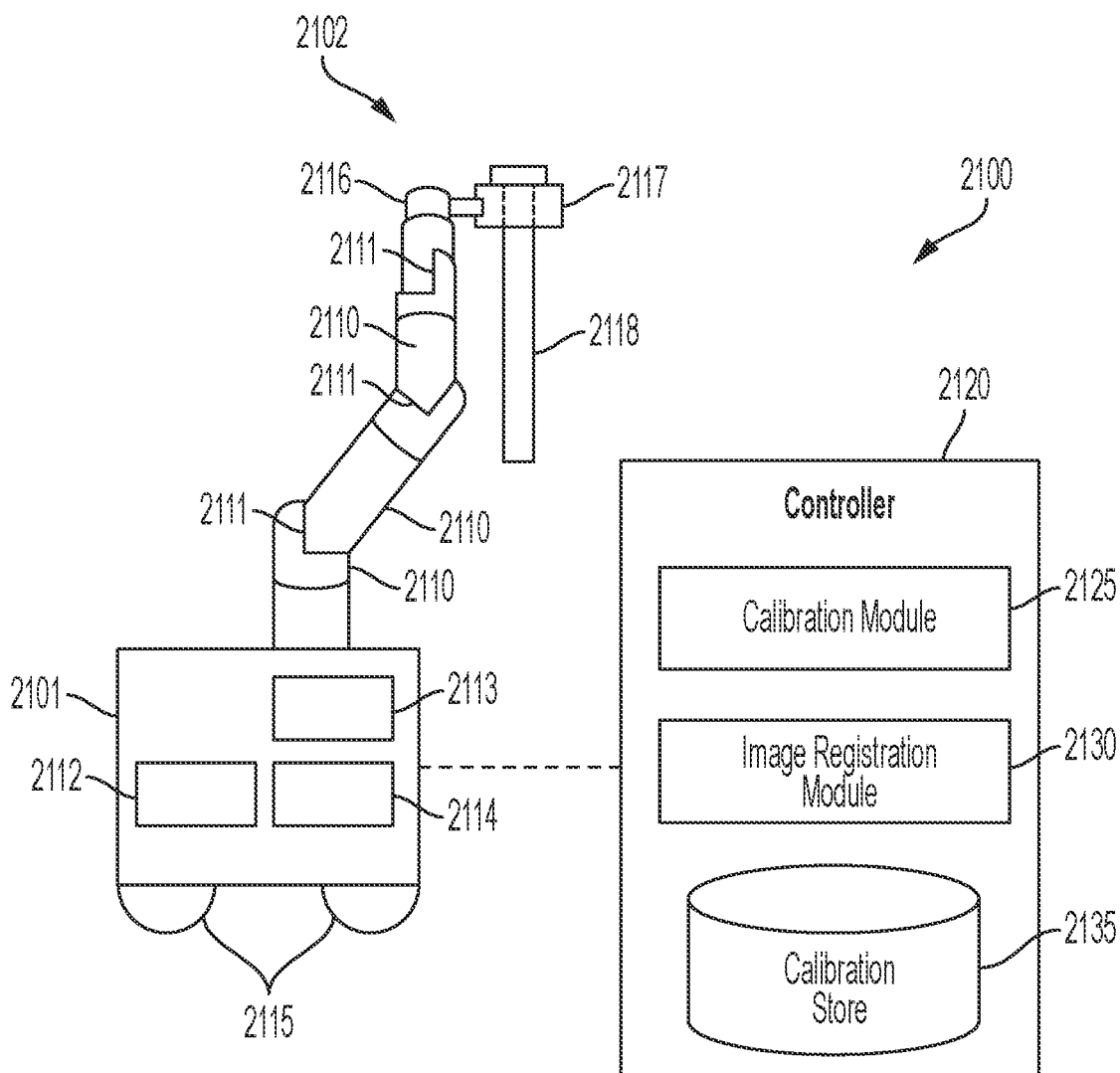

FIG. 31 is a schematic view of a robotic surgical system, in accordance with at least one aspect of the present disclosure.

Figure 32:
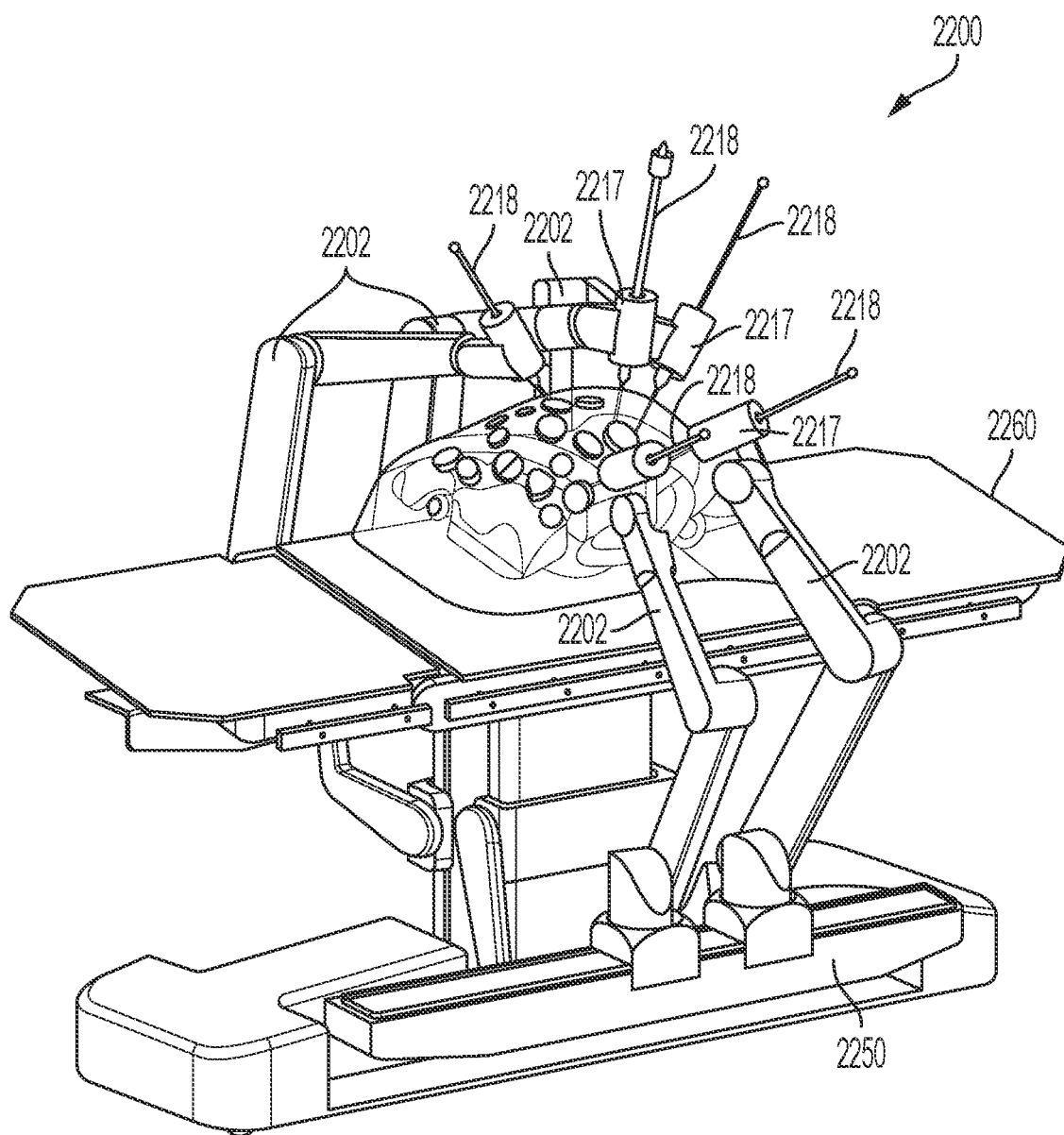

FIG. 32 is a perspective view of a surgical robot, in accordance with at least one aspect of the present disclosure.

Figure 33:
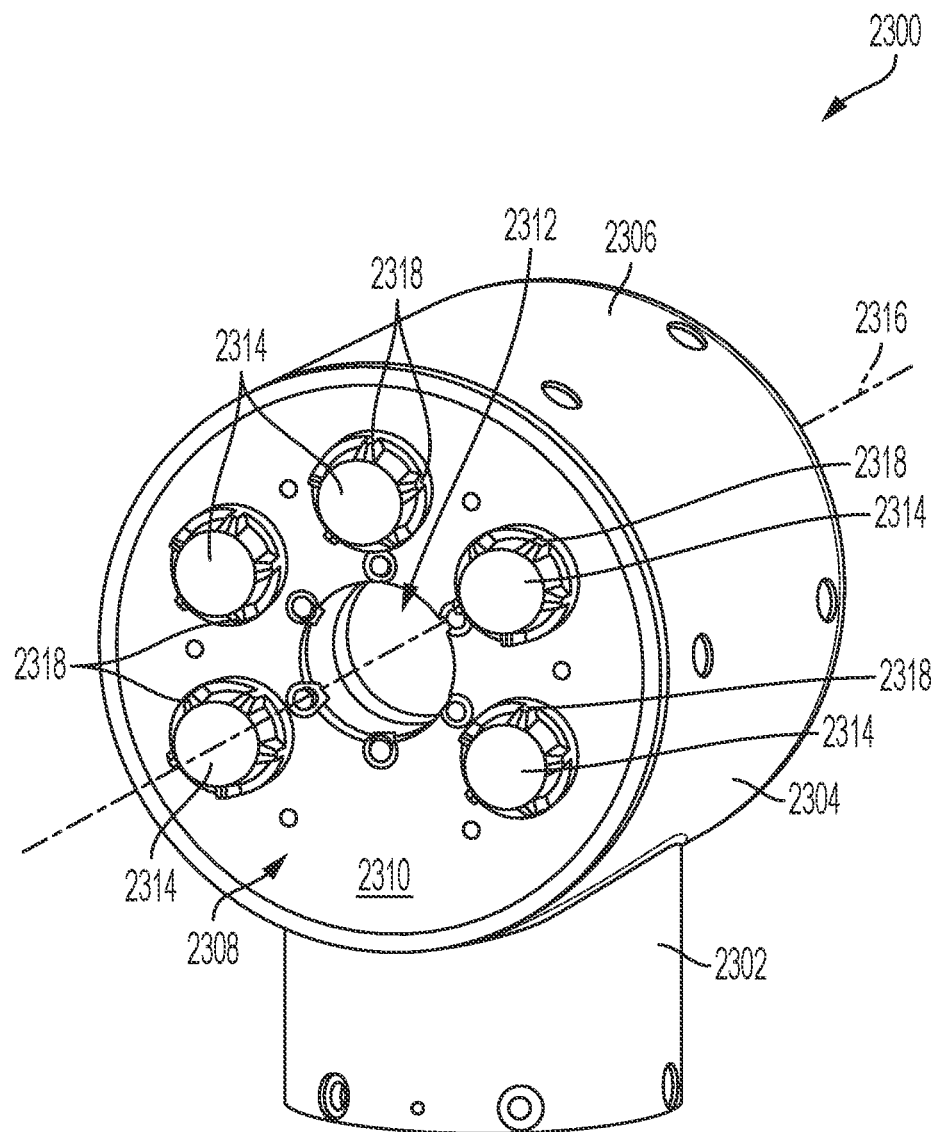

FIG. 33 is a perspective view of a tool driver for the robotic surgical system of FIG. 31 and the surgical robot of FIG. 32, in accordance with at least one aspect of the present disclosure.

Figure 34:
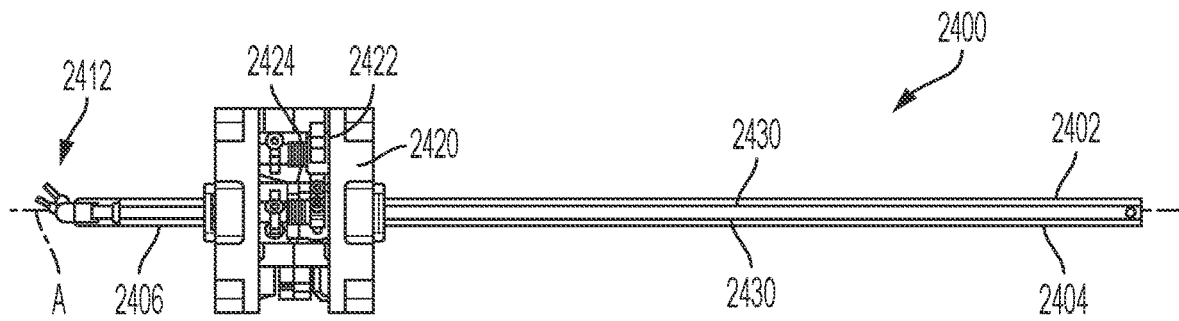

FIG. 34 is an elevation view of a surgical tool for use with the tool driver of FIG. 33, in accordance with at least one aspect of the present disclosure.

Figure 35:
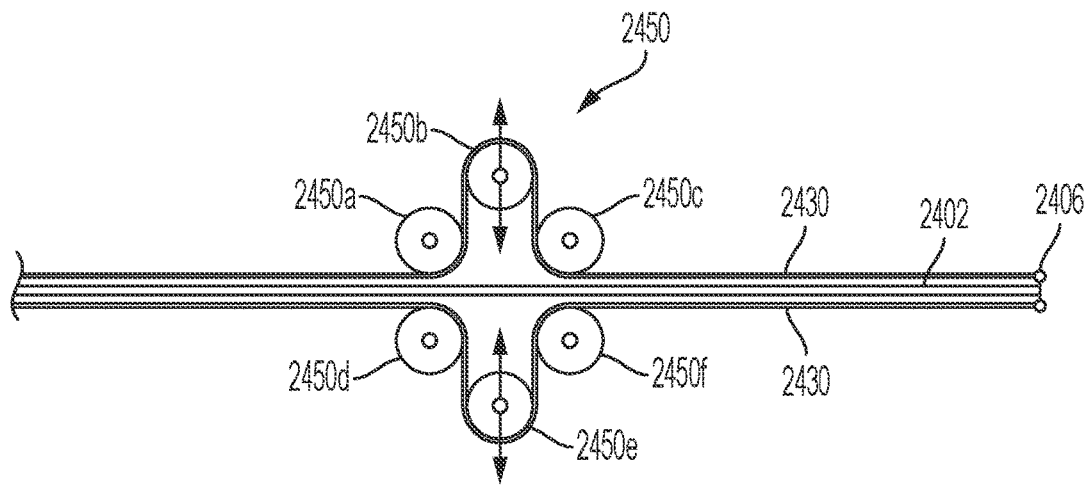

FIG. 35 is a plan view of an actuation mechanism for actuating an end effector of the surgical tool of FIG. 34, in accordance with at least one aspect of the present disclosure.

Figure 36:
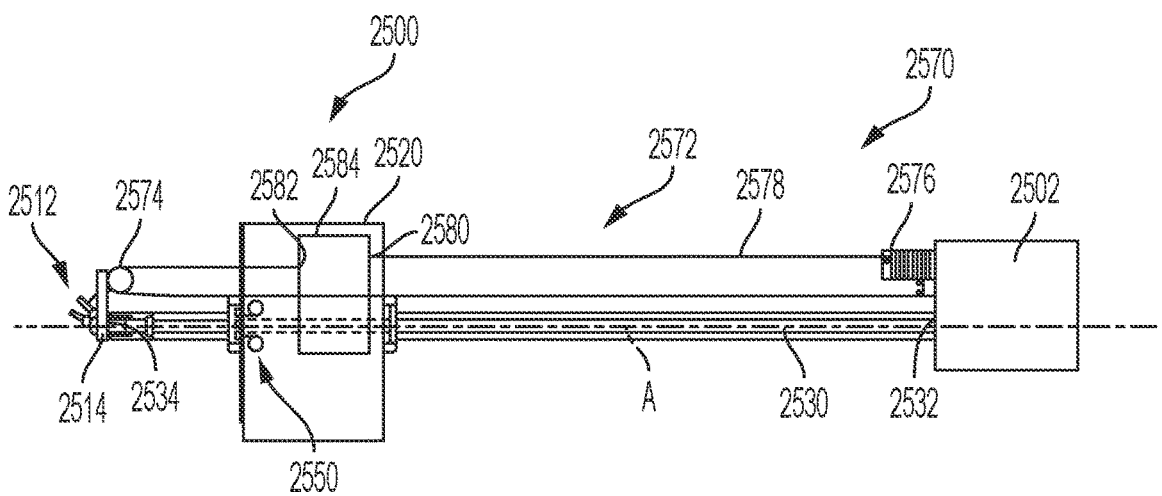

FIG. 36 is an elevation view of an actuation mechanism for translating the surgical tool of FIG. 34 relative to the tool driver of FIG. 33, in accordance with at least one aspect of the present disclosure.

Figure 37:
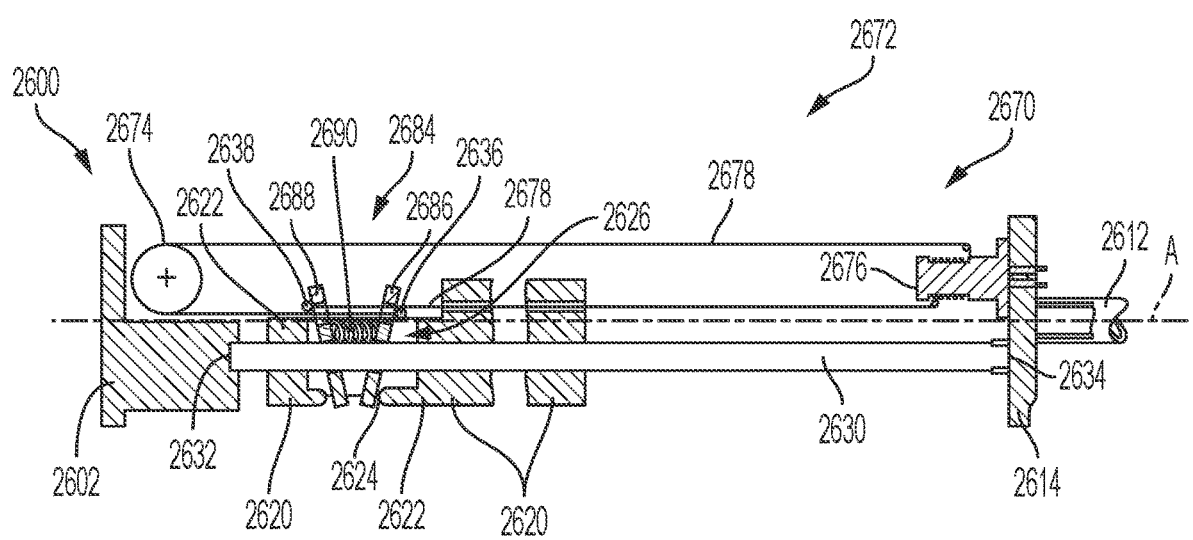

FIG. 37 is a cross-sectional elevation view of a portion of a surgical tool including an actuation mechanism for translating the surgical tool relative to a tool driver, in accordance with at least one aspect of the present disclosure.

Figure 38:
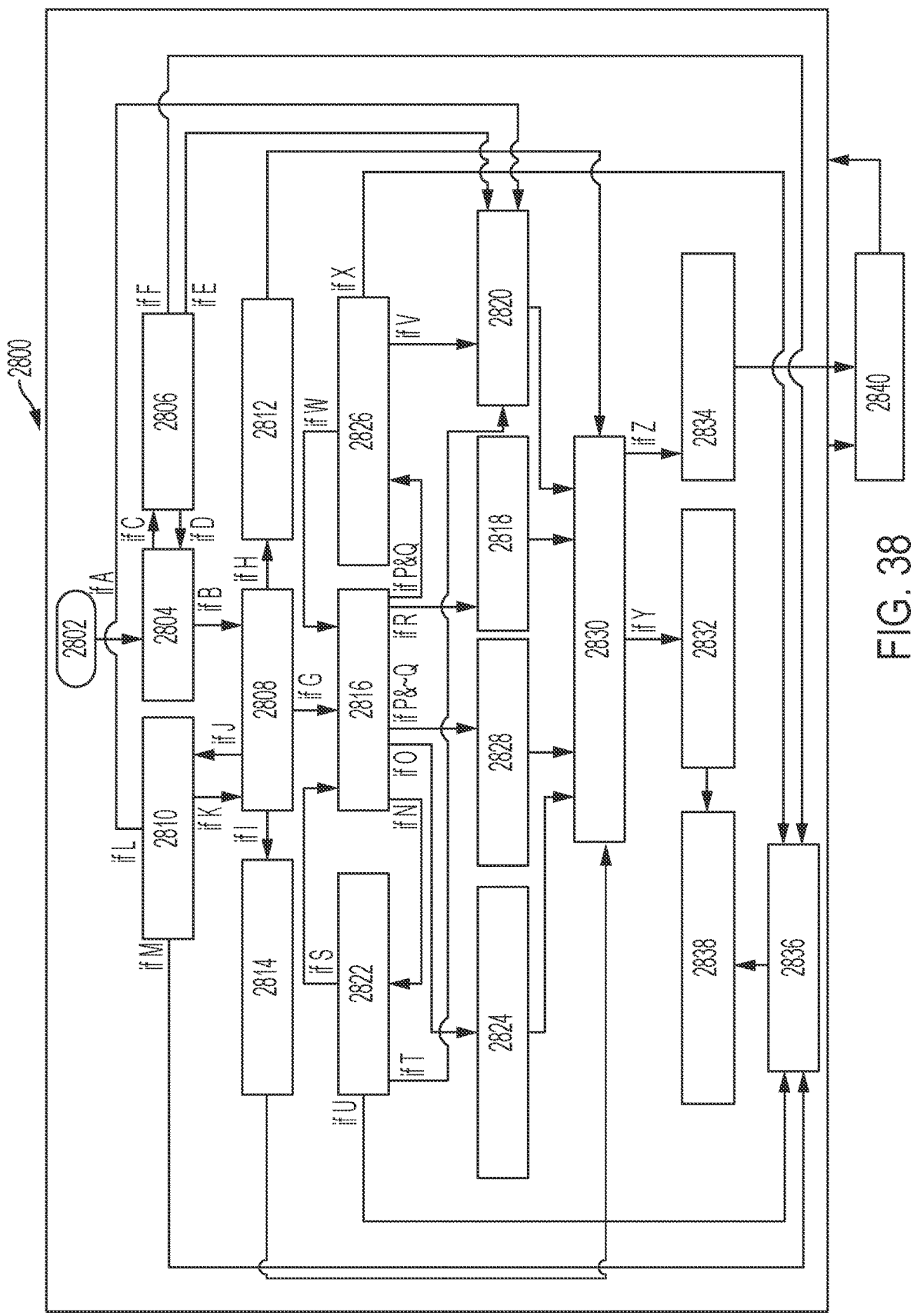

FIG. 38 is a flowchart depicting a transection operation for a surgical tool, in accordance with at least one aspect of the present disclosure.

Figure 39:
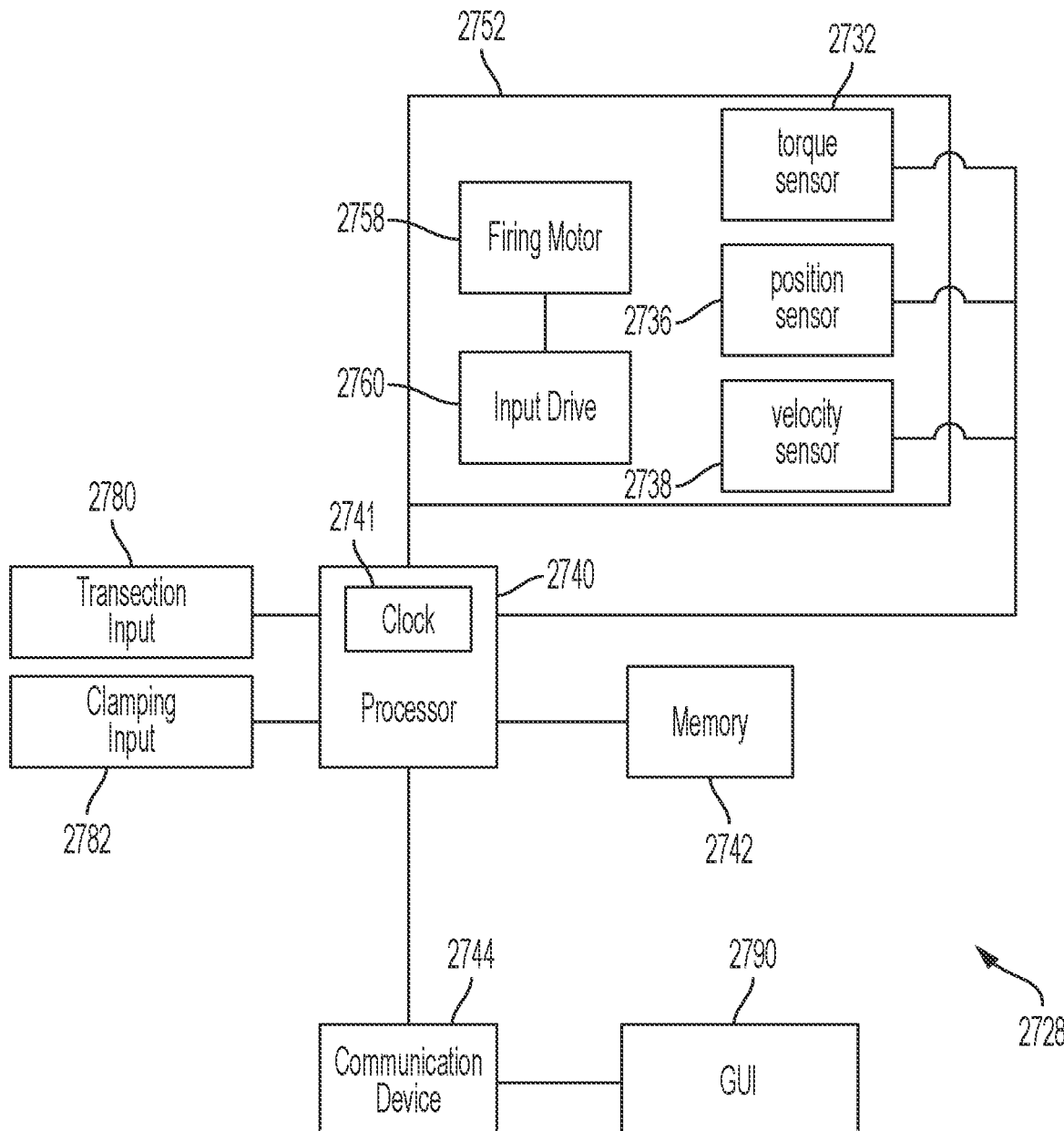

FIG. 39 is a control circuit diagram for implementing the transection operation, in accordance with at least one aspect of the present disclosure.

Corresponding reference characters indicate corresponding parts throughout the several views. The exemplifications set out herein illustrate certain embodiments of the invention, in one form, and such exemplifications are not to be construed as limiting the scope of the invention in any manner.

DESCRIPTION

Applicant of the present application also owns the following U.S. Patent Applications, filed on Dec. 30, 2020, each of which is herein incorporated by reference in its entirety:

U.S. patent application Ser. No. 17/137,829, titled SURGICAL TOOL WITH TOOL- BASED TRANSLATION AND LOCK FOR THE SAME, now U.S. Patent Application Publication No. 2022/0202437;

U.S. patent application Ser. No. 17/137,846, titled ROBOTIC SURGICAL TOOLS HAVING DUAL ARTICULATION DRIVES, U.S. Patent Application Publication No. 20220202517; and U.S. patent application Ser. No. 17/137,857 titled DUAL DRIVING PINION CROSSCHECK, now U.S. Pat. No. 11,813,746.

Applicant of the present application also owns U.S. patent application Ser. No. 16/553,725, titled ARTICULATING INCLUDING ANTAGONISTIC CONTROLS FOR ARTICULATION AND CALIBRATION, filed Aug. 28, 2019, which is incorporated by reference herein in its entirety.

Applicant of the present application also owns U.S. Provisional Patent Application No. 62/611,339, titled ROBOT ASSISTED SURGICAL PLATFORM, filed Dec. 28, 2017, which is incorporated by reference herein in its entirety.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS; and U.S. patent application Ser. No. 15/940,711, titled SENSING ARRANGEMENTS FOR ROBOT-ASSISTED SURGICAL PLATFORMS.

Before explaining various aspects of a robotic surgical platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Minimally-invasive surgery (MIS), such as laparoscopic surgery, typically involves techniques intended to reduce tissue damage during a surgical procedure. For example, laparoscopic procedures can involve creating a number of small incisions in the patient (e.g., in the abdomen) and introducing one or more surgical tools (e.g., end effectors and an endoscope) through the incisions into the patient. Surgical procedures may then be performed using the introduced surgical tools and with visualization aid provided by the endoscope, for example. Exemplary surgical visualization systems are further described in the following references, which are incorporated by reference herein in their respective entireties:

U.S. Patent Application Publication No. 2020/0015923 A1, titled SURGICAL VISUALIZATION PLATFORM, which published on Jan. 16, 2020;

U.S. Patent Application Publication No. 2020/0015904 A1, titled SURGICAL VISUALIZATION CONTROLS, which published on Jan. 16, 2020;

U.S. Patent Application Publication No. 2020/0015900 A1, titled CONTROLLING AN EMITTER ASSEMBLY PULSE SEQUENCE, which published on Jan. 16, 2020;

U.S. Patent Application Publication No. 2020/0015668 A1, titled SINGULAR EMR SOURCE EMITTER ASSEMBLY, which published on Jan. 16, 2020;

U.S. Patent Application Publication No. 2020/0015925 A1, titled COMBINATION EMITTER AND CAMERA ASSEMBLY, which published on Jan. 16, 2020;

U.S. Patent Application Publication No. 2020/0015899 A1, titled SURGICAL VISUALIZATION WITH PROXIMITY TRACKING FEATURES, which published on Jan. 16, 2020;

U.S. Patent Application Publication No. 2020/0015903 A1, titled SURGICAL VISUALIZATION OF MULTIPLE TARGETS, which published on Jan. 16, 2020;

U.S. Pat. No. 10,792,034, titled VISUALIZATION OF SURGICAL DEVICES, which was issued on Oct. 6, 2020;

U.S. Patent Application Publication No. 2020/0015897 A1, titled OPERATIVE COMMUNICATION OF LIGHT, which published on Jan. 16, 2020;

U.S. Patent Application Publication No. 2020/0015924 A1, titled ROBOTIC LIGHT PROJECTION TOOLS, which published on Jan. 16, 2020;

U.S. Patent Application Publication No. 2020/0015898 A1, titled SURGICAL VISUALIZATION FEEDBACK SYSTEM, which published on Jan. 16, 2020;

U.S. Patent Application Publication No. 2020/0015906 A1, titled SURGICAL VISUALIZATION AND MONITORING, which published on Jan. 16, 2020;

U.S. Patent Application Publication No. 2020/0015907 A1, titled INTEGRATION OF IMAGING DATA, which published on Jan. 16, 2020;

U.S. Patent Application Publication No. 2020/0015806 A1, titled ROBOTICALLY-ASSISTED SURGICAL SUTURING SYSTEMS, which published on Jan. 16, 2020;

U.S. Patent Application Publication No. 2020/0015901 A1, titled SAFETY LOGIC FOR SURGICAL SUTURING SYSTEMS, which published on Jan. 16, 2020;

U.S. Patent Application Publication No. 2020/0015914 A1, titled ROBOTIC SYSTEMS WITH SEPARATE PHOTOACOUSTIC RECEIVERS, which published on Jan. 16, 2020; and U.S. Patent Application Publication No. 2020/0015902 A1, titled FORCE SENSOR THROUGH STRUCTURED LIGHT DEFLECTION, which published on Jan. 16, 2020.

MIS may provide certain benefits, such as reduced patient scarring, less patient pain, shorter patient recovery periods, and/or lower medical treatment costs associated with patient recovery. Recent technological developments allow robotic systems to perform more MIS procedures. The robotic systems typically include one or more robotic arms for manipulating surgical tools based on commands from a remote operator (e.g. surgeon/clinician). A robotic arm may, for example, support at its distal end various surgical devices such as surgical end effectors, imaging devices, and cannulas for providing access to the patient's body cavity and organs.

Existing robotically-assisted surgical systems typically consist of a surgeon console and a patient-side cart with one or more interactive robotic arms controlled from the console. For example, one robotic arm can support a camera and the other robotic arm(s) can support robotic tools such as scalpels, scissors, graspers, and staplers, for example. Various exemplary robotic tools are further described herein.

A robotic surgical system disclosed herein can be a software-controlled, electro-mechanical system designed for surgeons to perform MIS procedures. The robotic surgical system can be used with an endoscope, compatible endoscopic instruments, and accessories. The system may be used by trained physicians in an operating room environment to assist in the accurate control of compatible endoscopic instruments during robotically-assisted urologic, gynecologic, gastrological, and other laparoscopic surgical procedures. The compatible endoscopic instruments and accessories for use with the surgical system are intended for endoscopic manipulation of tissue including stapling, grasping, cutting, blunt and sharp dissection, approximation, ligation, electrocautery, and suturing, for example.

Figure 1:
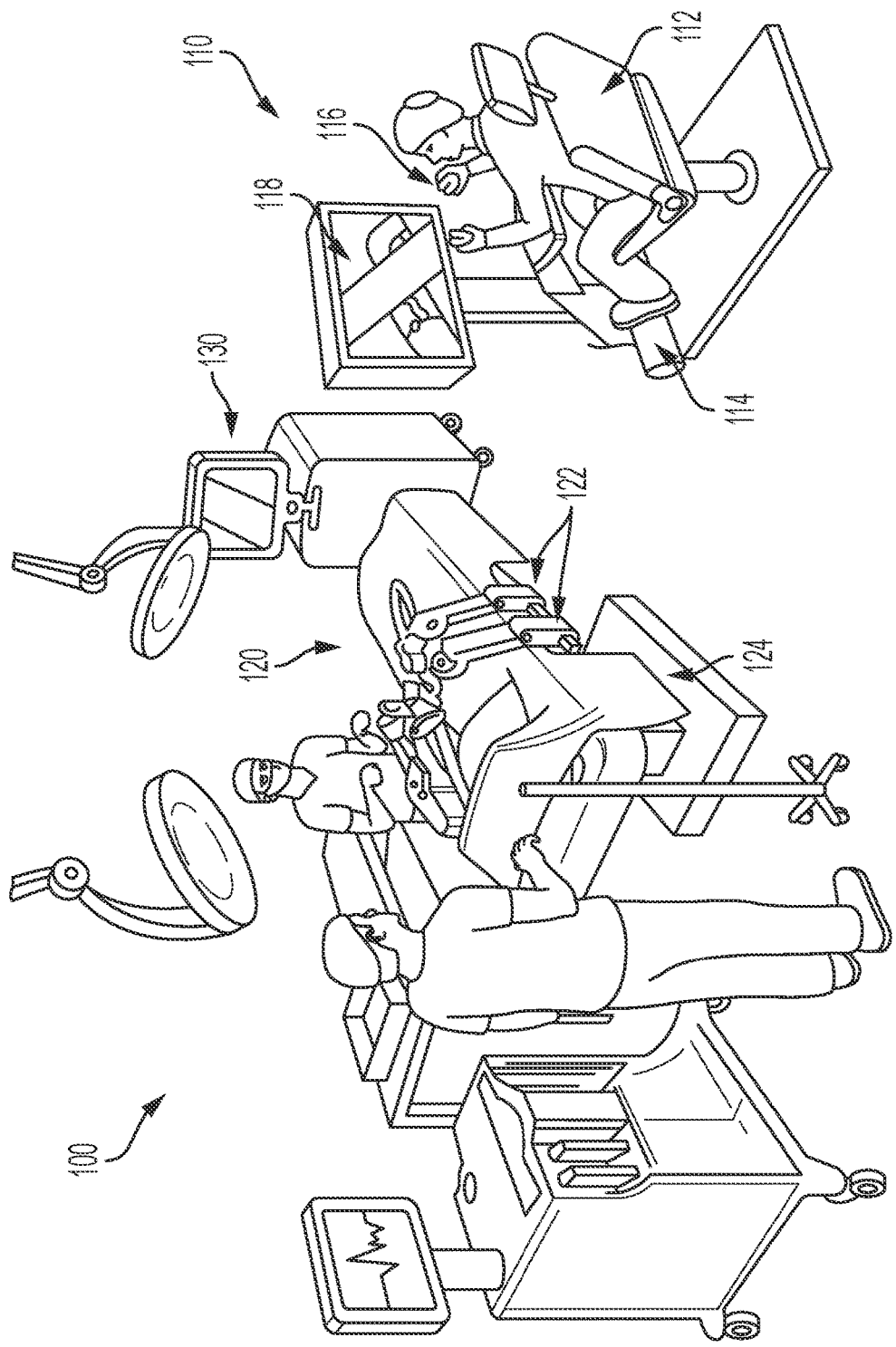
FIG. 1 is a schematic depicting an operating room including a robotic surgical system having multiple robotic arms, in accordance with at least one aspect of the present disclosure.

An example operating room environment is shown in FIG. 1. A robotic surgical system 100 is shown in the operating room, and the robotic surgical system 100 includes a user console 110, a control tower 130, and a surgical robot 120 having one or more robotic surgical arms 122 mounted on a surgical platform 124 (e.g., a table or a bed). Clinicians can mount surgical tools with end effectors to the distal ends of the robotic arms 122 for executing a surgical procedure. The robotic arms 122 are table-mounted, but in other configurations, the robotic arms can be mounted to a cart, a floor, a ceiling, a sidewall, or other suitable support surfaces. In various instances, the robotic arms can be supported by a free-standing robot having a base and/or upright column, as further described in U.S. patent application Ser. No. 16/553,725, titled ARTICULATING INCLUDING ANTAGONISTIC CONTROLS FOR ARTICULATION AND CALIBRATION, filed Aug. 28, 2019. U.S. patent application Ser. No. 16/553,725, titled ARTICULATING INCLUDING ANTAGONISTIC CONTROLS FOR ARTICULATION AND CALIBRATION, filed Aug. 28, 2019 is incorporated by reference herein in its entirety.

Generally, a user, such as a surgeon or other operator, is positioned at the user console 110 to remotely manipulate the robotic arms 122 and/or surgical instruments via teleoperation. The user console 110 can be located in the same operating room as the robotic system 100, as shown in FIG. 1. In other environments, the user console 110 can be located in an adjacent or nearby room, or tele-operated from a remote location in a different building, city, or country. The user console 110 can comprise a seat 112, pedals 114, one or more handheld user interface devices (UIDs) 116, and a display 118 configured to display, for example, a view of the surgical site inside a patient. As shown in the exemplary user console 110, a surgeon sitting in the seat 112 and viewing the open display 118 can manipulate the pedals 114 and/or handheld user interface devices 116 to remotely control the robotic arms 122 and/or surgical instruments mounted to the distal ends of the arms 122. Exemplary robotic input devices are further described in the following references, which are incorporated by reference herein in their respective entireties:

U.S. Patent Application Publication No. 2020/0289219 A1, titled INPUT CONTROLS FOR ROBOTIC SURGERY, which published on Sep. 17, 2020;
U.S. Patent Application Publication No. 2020/0289228 A1, titled DUAL MODE CONTROLS FOR ROBOTIC SURGERY, which published on Sep. 17, 2020;
U.S. Patent Application Publication No. 2020/0289216 A1, titled MOTION CAPTURE CONTROLS FOR ROBOTIC SURGERY, which published on Sep. 17, 2020;
U.S. Patent Application Publication No. 2020/0289229 A1, titled ROBOTIC SURGICAL CONTROLS HAVING FEEDBACK CAPABILITIES, which published on Sep. 17, 2020;
U.S. Patent Application Publication No. 2020/0289230 A1, titled ROBOTIC SURGICAL CONTROLS WITH FORCE FEEDBACK, which published on Sep. 17, 2020;
U.S. Patent Application Publication No. 2020/0289217 A1, titled JAW COORDINATION OF ROBOTIC SURGICAL CONTROLS, which published on Sep. 17, 2020;
U.S. Patent Application Publication No. 2020/0289220 A1, titled ROBOTIC SURGICAL SYSTEMS WITH MECHANISMS FOR SCALING SURGICAL TOOL MOTION ACCORDING TO TISSUE PROXIMITY, which published on Sep. 17, 2020;
U.S. Patent Application Publication No. 2020/0289205 A1, titled ROBOTIC SURGICAL SYSTEMS WITH MECHANISMS FOR SCALING CAMERA MAGNIFICATION ACCORDING TO PROXIMITY OF SURGICAL TOOL TO TISSUE, which published on Sep. 17, 2020;
U.S. Patent Application Publication No. 2020/0289221 A1, titled ROBOTIC SURGICAL SYSTEMS WITH SELECTIVELY LOCKABLE END EFFECTORS, which published on Sep. 17, 2020;
U.S. Patent Application Publication No. 2020/0289222 A1, titled SELECTABLE VARIABLE RESPONSE OF SHAFT MOTION OF SURGICAL ROBOTIC SYSTEMS, which published on Sep. 17, 2020; and
U.S. Patent Application Publication No. 2020/0289223 A1, titled SEGMENTED CONTROL INPUTS FOR SURGICAL ROBOTIC SYSTEMS, which published on Sep. 17, 2020.

In some variations, a user can also operate the robotic surgical system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. In these variations, the user may perform both robotic-assisted MIS and manual laparoscopic surgery on a patient.

In some aspects, the communication between the surgical robot 120 and the user console 110 can be through the control tower 130, which can translate user input from the user console 110 to robotic control commands and transmit the control commands to the surgical robot 120. The control tower 130 can also transmit status and feedback from the robot 120 back to the user console 110. The connections between the surgical robot 120, the user console 110, and the control tower 130 can be via wired and/or wireless connections, and can be proprietary and/or performed using any of a variety of data communication protocols. Any wired connections can be built into the floor and/or walls and/or ceiling of the operating room. The robotic surgical system 100 can provide video output to one or more displays, including displays within the operating room, as well as remote displays accessible via the Internet or other networks. The video output or feed can also be encrypted to ensure privacy and all or portions of the video output can be saved to a server or electronic healthcare record system.

The robotic surgical system 100 can uniquely identify each tool (endoscope and/or surgical tool) as soon as it is attached to an arm 122 thereof, and can display the tool type and arm location on the display 118 at the user console 110 and/or a touchscreen display on the control tower 130. The corresponding tool functions can be enabled and activated using the master UIDs 116 and foot pedals 114. The patient-side assistant can attach and detach the tools, as required, throughout the procedure. A surgeon seated at the user console 110 can begin to perform surgery using the tools controlled by two master UIDs 116 and foot pedals 114. The system translates the surgeon's hand, wrist, and/or finger movements through the master UIDs 116 into precise real-time movements of the surgical tools. Therefore, the system constantly monitors every surgical maneuver of the surgeon and can pause instrument movement if the system is unable to precisely mirror the surgeon's hand motions.

Figure 2:
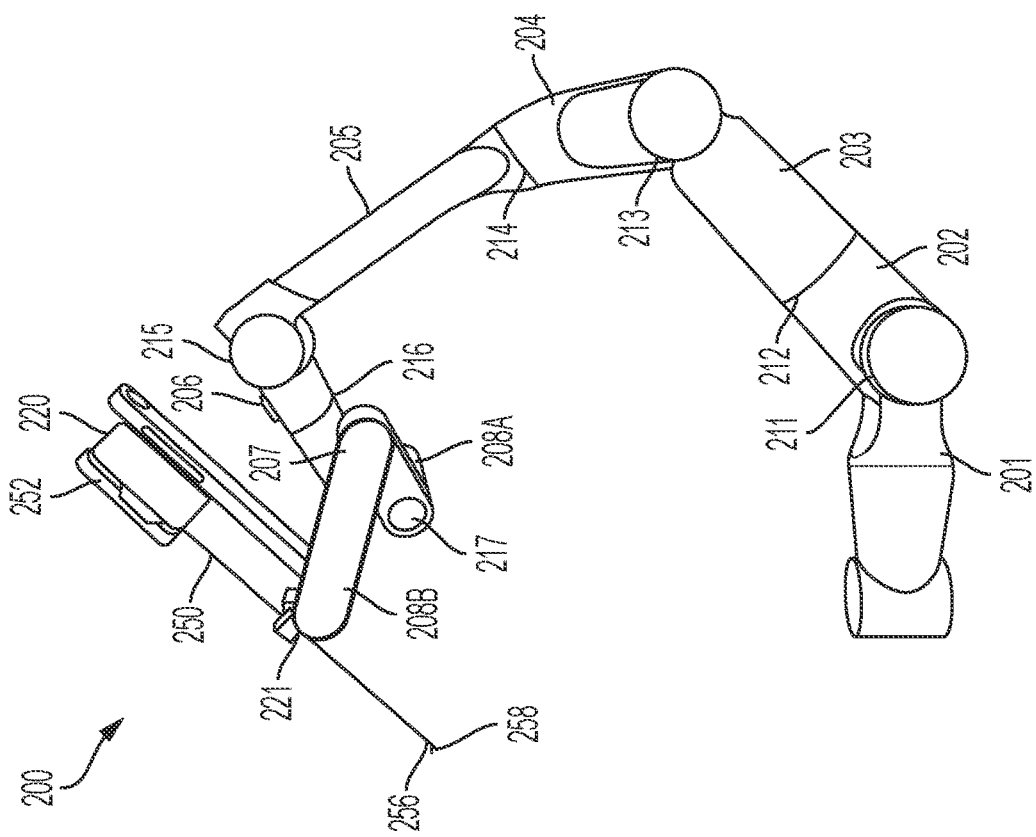
FIG. 2 is a perspective view of a robotic arm including a tool drive, and also depicting a robotic tool mounted to the tool drive, in accordance with at least one aspect of the present disclosure.

A robotic arm 200 is shown in FIG. 2. The robotic arm 200 can be incorporated into the surgical robot 120 (FIG. 1). For example, the robotic arm 200 can correspond to one of the robotic arms 122 (FIG. 1) of the surgical robot 120. The robotic arm 200 includes a tool drive 220 and a cannula 221. A robotic surgical tool 250 is mounted to the tool drive 220 and is installed in the cannula 221. The robotic arm 200 includes links (e.g., links 201, 202, 203, 204, 205, 206, 207, 208A, 208B) and actuated joint modules (e.g., joints 211, 212, 213, 214, 215, 216, 217) for actuating the plurality of links relative to one another. The joint modules can include various types, such as a pitch joint or a roll joint, which may substantially constrain the movement of the adjacent links around certain axes relative to others. The tool drive 220 is attached to the distal end of the robotic arm 200 and includes the sleeve or cannula 221 extending distally therefrom. The cannula 221 is configured to receive and guide the surgical tool 250 into the patient. The robotic tool 250 also includes an articulation joint or wrist 256 and an end effector 258 (FIG. 2) disposed at the distal end. The joint modules 211, 212, 213, 214, 215, 216, 217 of the robotic arm 200 can be actuated to position and orient the tool drive 220, which actuates the robotic wrist 256 and the end effector 258 for robotic surgery.

Figure 3:
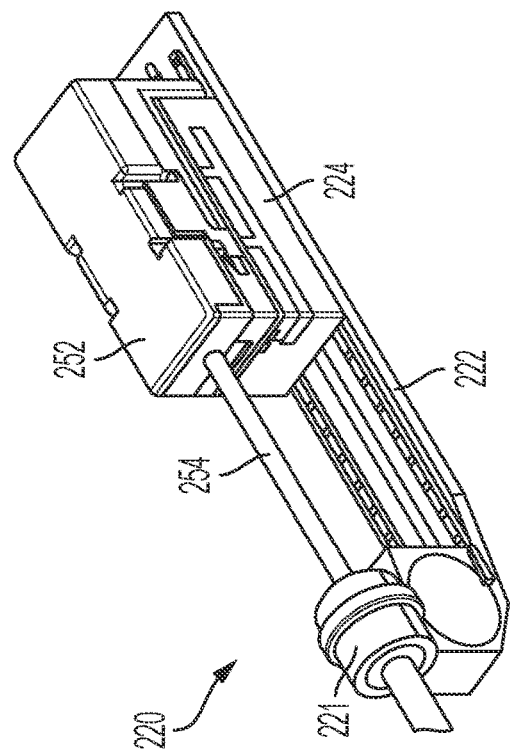
FIG. 3 is a perspective view of the tool drive of FIG. 2 and a proximal tool base of the robotic tool of FIG. 2 mounted to the tool drive, in accordance with at least one aspect of the present disclosure.
Figure 4:
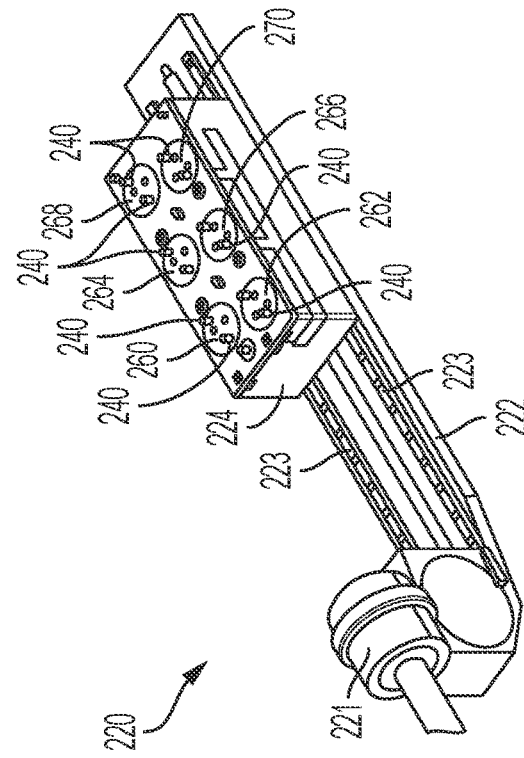
FIG. 4 is a perspective view of the tool drive of FIG. 2 without a robotic tool base mounted thereon, in accordance with at least one aspect of the present disclosure.

FIG. 3 depict the tool drive 220 with the surgical tool 250 mounted thereto and FIG. 4 depicts the tool drive 22 without a surgical tool mounted thereto. The tool drive 220 includes an elongated base (or "stage") 222 having longitudinal tracks 223 and a tool carriage 224, which is slidingly engaged with the longitudinal tracks 223. The stage 222 may be configured to couple to the distal end of a robotic arm 200 such that articulation of the robotic arm 200 positions and/or orients the tool drive 220 in space. Additionally, the tool carriage 224 is configured to receive a tool base 252 of the robotic tool 250. The robotic tool 250 also includes a tool shaft 254 extending from the tool base 252 and through the cannula 221.

Generally, the tool carriage 224 provides various degrees of freedom for the robotic tool 250 coupled to the tool carriage 224. For example, longitudinal movement of the tool carriage 224 along the longitudinal tracks 223 provides a translational degree of freedom for the surgical tool 250 along a tool axis. Alternative translational degrees of freedom, e.g. along an insertion axis, are further described herein.

Additionally, the tool carriage 224 provides a rotational degree of freedom for rotation of the surgical tool 250 around a tool axis, as well as various degrees of freedom for actuation or articulation of an end effector of the surgical tool (e.g., grasping or cutting). For example, the tool carriage 224 includes one or more motor drives (e.g., linear axis drive or rotary axis drive) whose outputs may be coupled to the input driving mechanisms of a surgical tool. A first motor drive may actuate a first degree of freedom, a second motor drive may actuate a second degree of freedom, and so on for all the additional motor drives in the tool carriage. For example, at least one motor drive may actuate rotation of the tool shaft in a first direction (e.g., clockwise) and another motor drive may actuate rotation of the tool shaft in a second direction opposite the first (e.g., counter-clockwise) in antagonistic fashion. Alternatively, at least one motor drive may actuate rotation of the tool shaft in two directions (e.g., both clockwise and counter-clockwise). Such actuation of the tool may involve, for example, a cable-driven mechanism or set of mechanisms in the tool that are coupled to the output of the motor drives in the tool carriage. Exemplary variations of the tool carriage are further described below.

The tool carriage 224 is configured to actuate a set of articulated movements of the robotic wrist 256 and the end effector 258 through a system of gears, shafts, cables, and/or wires that are manipulated and controlled by actuated drives. Referring to FIG. 4, the tool carriage 224 includes six motors and six corresponding rotary drivers 260, 262, 264, 266, 268, and 270, which are rotary inputs to a robotic tool. The rotary drivers 260, 262, 264, 266, 268, and 270 are arranged in two rows and extending longitudinally along the base. The rotary drivers 260, 262, 264, 266, 268, and 270 in FIG. 4 are slightly staggered to reduce the overall width of the tool carriage 224 such that the tool carriage 224 is more compact. Rotary drives 260, 264, and 268 are arranged in a first row and rotary drivers 262, 266, and 270 are arranged in a second row that is slightly longitudinally offset from the first row. Tool carriages having six rotary drives are further described in U.S. Patent Application Publication No. 2020/0138534, titled ROBOTIC SURGICAL SYSTEM, which published on May 7, 2020 and U.S. patent application Ser. No. 16/553,725, titled ARTICULATING INCLUDING ANTAGONISTIC CONTROLS FOR ARTICULATION AND CALIBRATION, filed Aug. 28, 2019, for example. U.S. Patent Application Publication No. 2020/0138534, titled ROBOTIC SURGICAL SYSTEM, which published on May 7, 2020 and U.S. patent application Ser. No. 16/553,725, titled ARTICULATING INCLUDING ANTAGONISTIC CONTROLS FOR ARTICULATION AND CALIBRATION, filed Aug. 28, 2019, are incorporated by reference herein in their respective entireties.

In other instances, the tool carriage 224 may include a different configuration of actuated drives. For example, U.S. Patent Application Publication No. 2019/0201111, titled DRIVE ARRANGEMENTS FOR ROBOTIC-ASSISTED SURGICAL PLATFORMS, which published on Jul. 4, 2019, describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, also describes tool carriages having various drive arrangements. U.S. Pat. No. 9,072,535, titled SURGICAL STAPLING INSTRUMENTS WITH ROTATABLE STAPLE DEPLOYMENT ARRANGEMENTS, which issued Jul. 7, 2015, and U.S. Patent Application Publication No. 2019/0201111, titled DRIVE ARRANGEMENTS FOR ROBOTIC-ASSISTED SURGICAL PLATFORMS, which published on Jul. 4, 2019, are incorporated by reference herein in their respective entireties. Alternative drive arrangements are further described herein.

Figure 5:
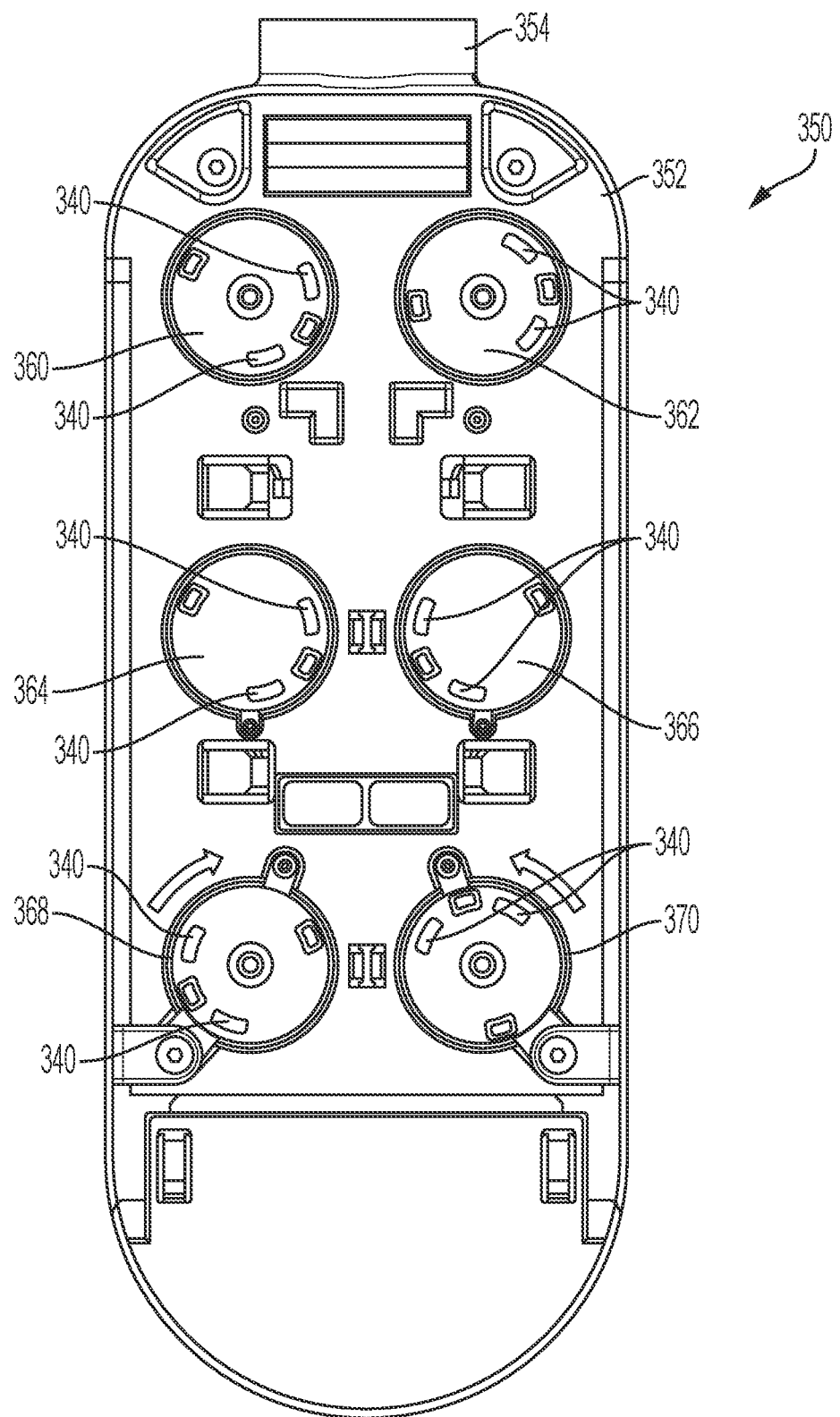
FIG. 5 is a plan view of a proximal portion of a robotic tool, in accordance with at least one aspect of the present disclosure.

Referring now to FIG. 5, a proximal portion of a robotic tool 350 is shown. The robotic tool 350 can be similar to the robotic tool 250 (FIGS. 2 and 3) in many aspects and can be adapted for use with the tool drive 220 (FIGS. 2-4) and the surgical robot 120 (FIG. 1), for example. The proximal portion of the robotic tool 350 includes a tool base 352; an elongate shaft 354 extends distally from the base 352 toward an end effector. The base 352 includes six rotary drives 360, 362, 364, 366, 368, and 370 that are configured to mate with six rotary motor-driven inputs on a tool carriage, such as the rotary drivers 260, 262, 264, 266, 268, and 270 on the tool carriage 224 (FIG. 4), for example. In various instances, each rotary drive 360, 362, 364, 366, 368, and 370 can be associated with a degree of freedom of the robotic tool 350. In other instances, one or more rotary drives can correspond to multiple degrees of freedom via a transmission. Exemplary drive arrangements for robotic tools are further described in U.S. Patent Application Publication No. 2019/0201111, titled DRIVE ARRANGEMENTS FOR ROBOTIC-ASSISTED SURGICAL PLATFORMS, which published on Jul. 4, 2019 and is incorporated by reference herein in its entirety.

Each rotary drive 360, 362, 364, 366, 368, and 370 includes a rotatable disc or puck configured to align and mate with the corresponding rotary driver 260, 262, 264, 266, 268, and 270 (FIG. 4). For example, the rotary drivers 260, 262, 264, 266, 268, and 270 and rotary drives 360, 362, 364, 366, 368, and 370 include one or more matable surface features 240 (FIG. 4) and 340 (FIG. 5), respectively, configured to facilitate mating engagement between the opposing surface features 240, 340 such that movement (i.e. rotation) of a given rotary driver 260, 262, 264, 266, 268, and 270 correspondingly moves (i.e. rotates) the associated rotary drive 360, 362, 364, 366, 368, and 370.

The tool carriage 224 can include torque sensors and rotary encoders, which may be incorporated into the motors of some or all of the rotary drivers 260, 262, 264, 266, 268, and 270. The torque sensors may be configured to measure the real-time torque loading on the motors, which corresponds to the torque loading assumed by the rotary drivers 260, 262, 264, 266, 268, and 270 and/or rotary drives 360, 362, 364, 366, 368, and 370 in the robotic tool 350 coupled thereto. The rotary encoders may measure the rotational motion or output of the motors, which corresponds to the rotational motion of the rotary drivers 260, 262, 264, 266, 268, and 270 and/or rotary drives 360, 362, 364, 366, 368, and 370. Monitoring torque loading and rotational motion of the motors may help determine if the surgical tool 350 is operating in accordance with the commands provided by the control tower 130. Additionally or alternatively, torque sensors and/or rotary encoders can be operatively coupled to one or more of the rotary drives 360, 362, 364, 366, 368, and 370 in the robotic tool 350.

Referring again to FIG. 5, the rotary drives 360, 362, 364, 366, 368, and 370 in the tool base 352 can implement the various degrees of freedom of the robotic tool 350. For example, the rotary drive 360 can correspond to a pitching motion of the robotic tool 350, the rotary drive 362 can correspond to a rolling motion of the robotic tool 350, the rotary drive 364 can correspond to a first yawing motion of the robotic tool 350, the rotary drive 366 can correspond to a second yawing motion of the robotic tool 350 in an opposite direction to the first yawing motion, for example, the rotary drive 368 can correspond to a clamping motion (e.g. closing of the jaws) of the robotic tool 350, and the rotary drive 370 can correspond to a firing motion (e.g. cutting and stapling of tissue) of the robotic tool 350. In such instances, a single rotary drive coupled to a single rotary input in the tool carriage is configured to close the jaws.

A transmission can allow a greater amount of degrees of freedom than an arrangement in which each motor and corresponding rotary input is dedicated to a single degree of freedom. In certain instances, to achieve a higher torque state-such as when firing a firing member through thick and/or tough tissue, which requires a high torque input-more than one rotary input on the tool carriage can be drivingly coupled to a degree of freedom. Such a drive arrangement is described in U.S. Patent Application Publication No. 2019/0201111, titled DRIVE ARRANGEMENTS FOR ROBOTIC-ASSISTED SURGICAL PLATFORMS, which published on Jul. 4, 2019, and which is incorporated by reference herein in its entirety. In other instances, as further described herein, a single rotary drive in the base 352 can selectively toggle between a high-speed mode and a high-torque mode via a torque transition member.

Figure 6:
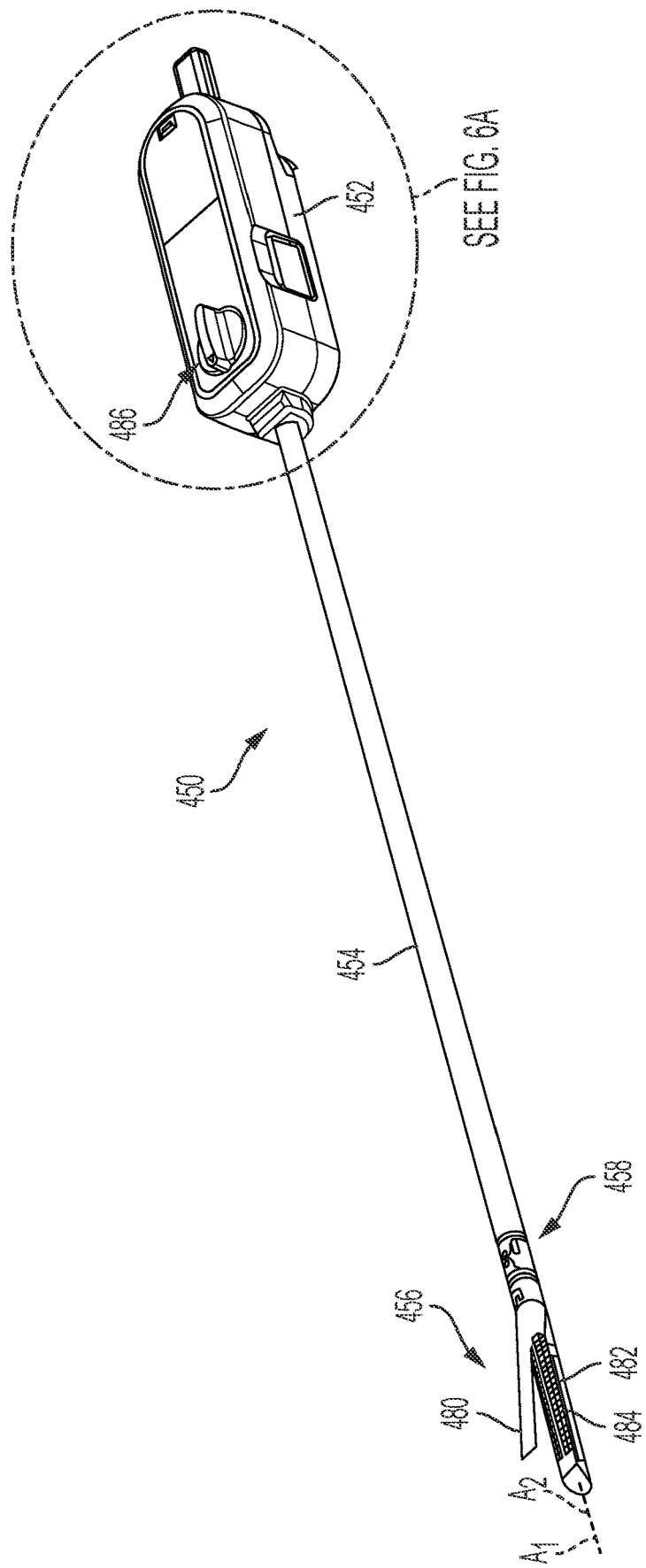
FIG. 6 is a perspective view of a surgical stapling tool, in accordance with at least one aspect of the present disclosure.

The robotic tool 350 can be a stapling tool that is configured to clamp, cut, and staple tissue. Referring now to FIG. 6, a surgical stapling tool 450 is shown. The surgical tool 450 is similar to the surgical tool 350 in many aspects and, therefore, may be used in conjunction with a robotic surgical system, such as the robotic surgical system 100 (FIG. 1) and with the robotic arm 200 (FIG. 2) and the tool drive 220 (FIGS. 2 and 3). The surgical stapling tool 450 includes a tool base, or proximal housing, 452 which is similar in many aspects to the tool base 352 (FIG. 5) and includes six rotary drives 460, 462, 464, 466, 468, and 470 (FIGS. 6A and 6B) similar to the rotary drives 360, 362, 364, 366, 368, and 370 (FIG. 5), for example. An elongate shaft 454 extends distally from the tool base 452. A distal end effector 456 is coupled to a distal end of the elongate shaft 454 at an articulation joint, or wrist joint, 458. The distal end effector 456 includes a first jaw 480 and a second jaw 482. The first jaw 480 and the second jaw 482 are configured to clamp tissue therebetween. For example, the first jaw 480 is a movable anvil, and the second jaw 482 is configured to support a fastener cartridge therein.

In other instances, the distal end effector 456 can include a fixed anvil and movable fastener cartridge. In still other instances, both jaws 480, 482 can be pivotable or otherwise movable between an open configuration and a clamped configuration to clamp tissue.

In other instances, the opposing jaws 480, 482 may form part of other types of end effectors with jaws such as, but not limited to, a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated 20 grasper, etc.) One or both of the jaws 480, 482 may be configured to pivot to actuate the end effector 456 between the open and closed positions.

The articulation joint 458 enables the end effector 456 to articulate or pivot relative to the shaft 454 and thereby position the end effector 456 at desired orientations and locations relative to a surgical site. In general, the articulation joint 458 includes a joint configured to allow pivoting movement of the end effector 456 relative to the shaft 454. The degrees of freedom of the wrist 458 can be represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 456) with respect to a given reference Cartesian frame. "Surge" can refer to forward and backward translational movement, "heave" can refer to translational movement up and down, and "sway" can refer to translational movement left and right. With regard to the rotational terms, "roll" can refer to tilting side to side, "pitch" can refer to tilting forward and backward, and "yaw" can refer to turning left and right.

The pivoting motion can include pitch movement about a first axis of the articulation joint 458 (e.g., X-axis), yaw movement about a second axis of the articulation joint 458 (e.g., Y-axis), and combinations thereof to allow for 360° rotational movement of the end effector 456 about the articulation joint 458. In other applications, the pivoting motion at the articulation joint 458 can be limited to movement in a single plane, e.g., only pitch movement about the first axis of the articulation joint 458 or only yaw movement about the second axis of the articulation joint 458, such that the end effector 456 moves only in a single plane.

The surgical tool 450 includes drive members that form part of an actuation system configured to facilitate articulation of the articulation joint 458 and actuation (operation) of the end effector 456 (e.g., clamping, firing, rotation, articulation, energy delivery, etc.). Some drive members may extend to the articulation joint 458, and selective actuation of these drive members causes the end effector 456 to articulate relative to the shaft 454 at the articulation joint 458. The end effector 456 is depicted in an unarticulated position in FIG. 6, in which a longitudinal axis A2 of the end effector 456 is substantially aligned with a longitudinal axis A1 of the shaft 454, such that the end effector 456 is at a substantially zero angle relative to the shaft 454. In an articulated position, the longitudinal axes A1, A2 would be angularly offset from each other such that the end effector 456 is at a non-zero angle relative to the shaft 454.

Other drive members may extend to the end effector 456, and selective actuation of those drive members may cause the end effector 456 to actuate, operate, or implement a surgical function. In the illustrated embodiment, actuating the end effector 456 may comprise closing and/or opening the second jaw 480 relative to the first jaw 482 (or vice versa), thereby enabling the end effector 456 to grasp or clamp onto tissue. In addition, once tissue is grasped or clamped between the opposing jaws 480, 482, actuating the end effector 456 may further comprise "firing" the end effector 456, which may refer to causing a cutting element or knife to advance distally within a slot 484 defined in the second jaw 482. As the cutting element moves distally, it may transect any tissue grasped between the opposing jaws 480, 482. Moreover, as the cutting element advances distally, a plurality of staples contained within the staple cartridge, (e.g., housed within the first jaw 482) may be urged or caromed into deforming contact with corresponding anvil surfaces (e.g., staple-forming pockets), provided on the second jaw 480. The deployed staples may form multiple rows of staples that seal opposing sides of tissue that may be transected with the knife or other cutting element.

In some aspects of the present disclosure, the surgical tool 450 may be configured to apply energy to tissue, such as radio frequency (RF) energy. In such cases, actuating the end effector 456 may further include applying energy to tissue grasped or clamped between two opposing jaws to cauterize or seal the captured tissue, for example.

In some aspects of the present disclosure, the surgical tool 450 may further include a manual closure device 486 accessible to a user on the exterior of the tool base or drive housing 452. The manual closure device 486 includes a knob that a clinician may grasp and actuate. The manual closure device 486 may be operatively coupled to various gears and/or drive members within the drive housing 452 to allow a clinician to manually open and close the jaws 480, 482. In some cases, a clinician may be able to fully clamp and fully unclamp the jaws 480, 482 with the manual closure device 486. Manual closure devices are further described in U.S. patent application Ser. No. 16/553,725, titled ARTICULATING INCLUDING ANTAGONISTIC CONTROLS FOR ARTICULATION AND CALIBRATION, filed Aug. 28, 2019, for example.

Figure 6B:
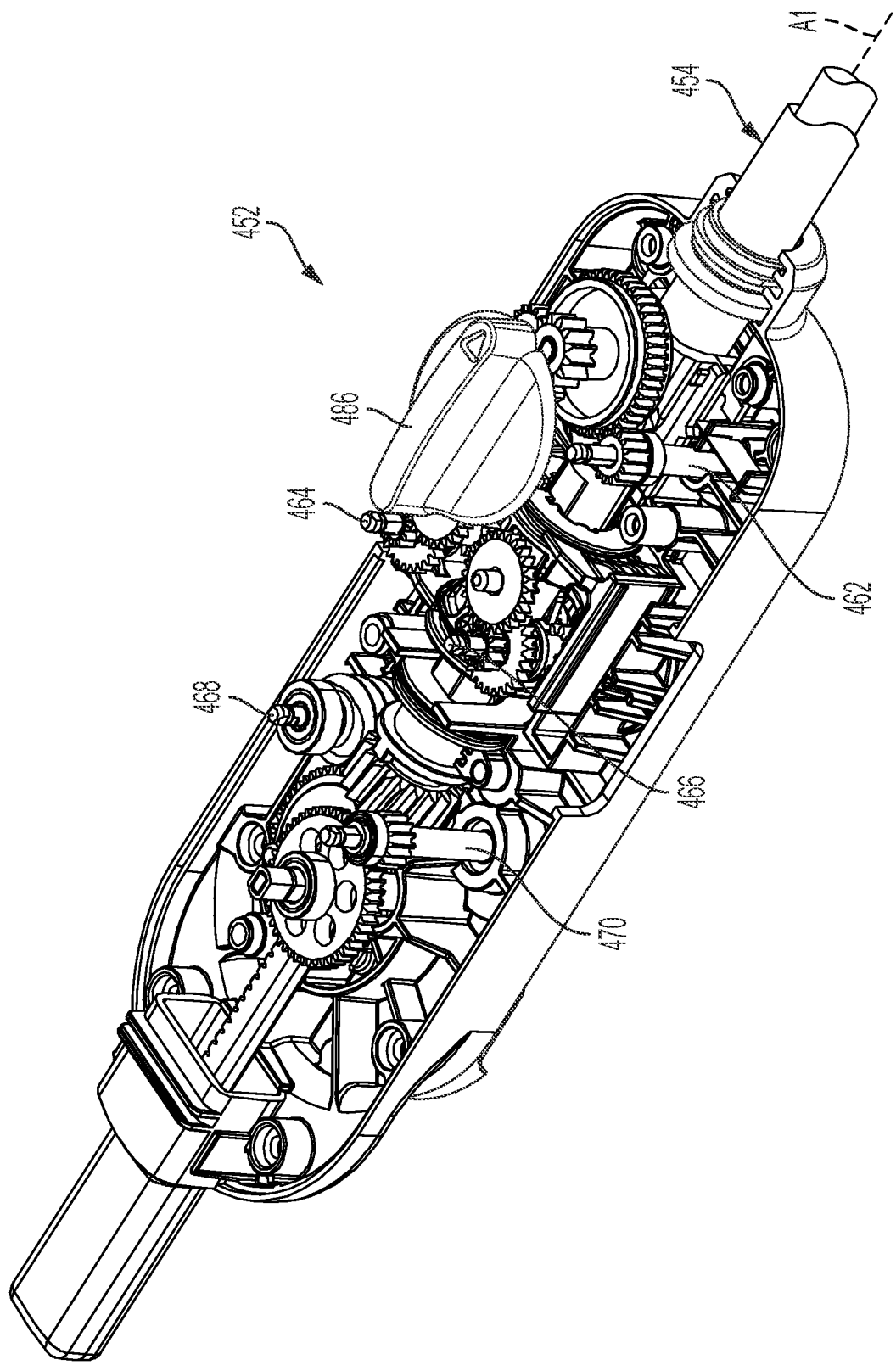
FIG. 6B is a perspective, detail view of the portion of the proximal tool base of FIG. 6A and with certain components removed for clarity, in accordance with at least one aspect of the present disclosure.
Figure 7:
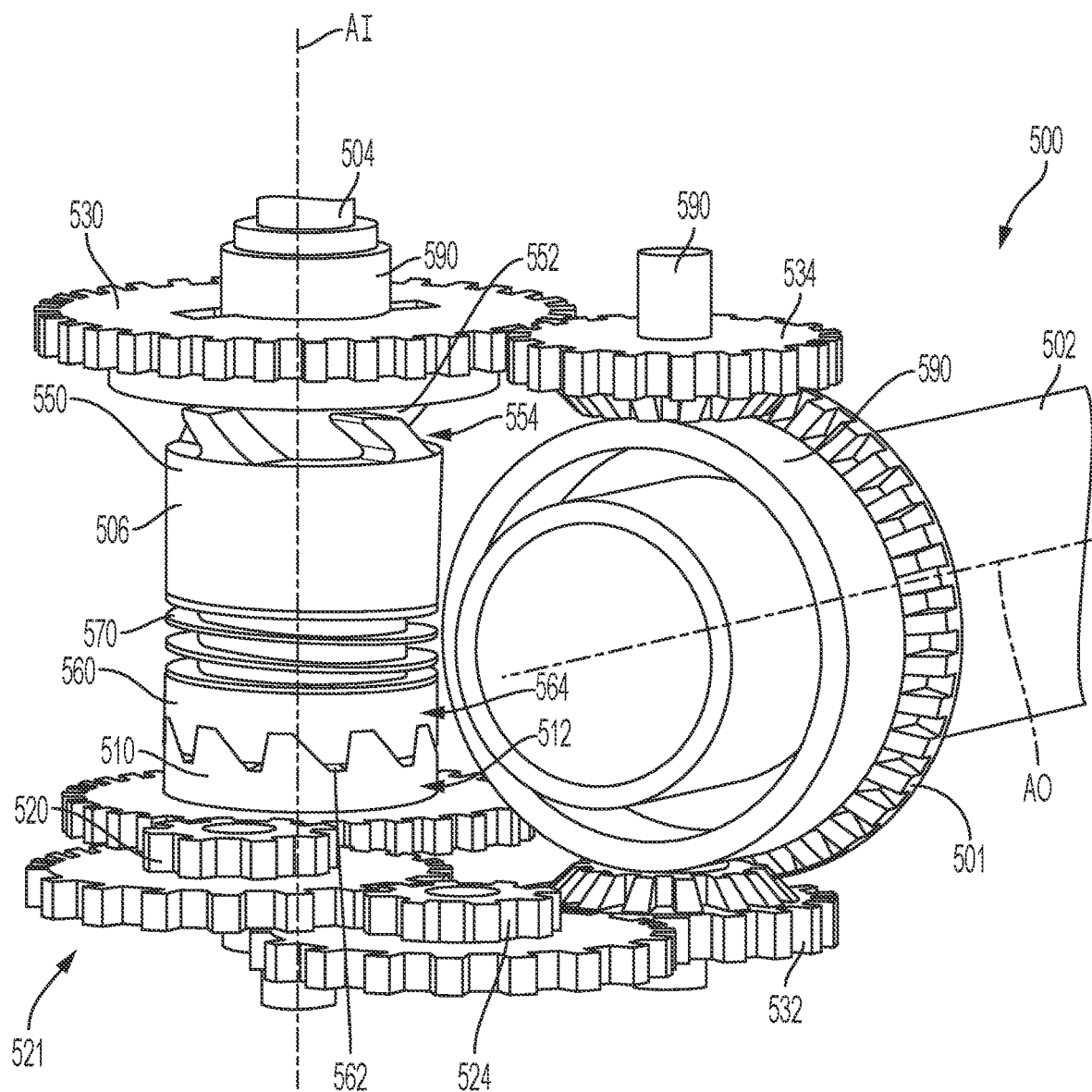
FIG. 7 is a perspective view of a rotary drive system for the surgical stapling tool of FIG. 6, wherein the rotary drive system includes a transition nut slidably positioned between a high-torque gear assembly and a high-speed gear assembly, in accordance with at least one aspect of the present disclosure.

Referring to FIGS. 6A and 6B, the upper portion of the drive housing 452 is omitted from this view to expose various internal working components and parts. Several components that would otherwise be included within the drive housing 452 are also omitted for clarity. The rotary drives 460, 462, 464, 466, 468, and 470 are housed in the tool base 452 and drivingly coupled to rotary drives on a tool drive (e.g. tool drive 220). The drive arrangements in FIGS. 6A and 6B are configured to transmit rotary motion from the rotary drives 460, 462, 464, 466, 468, and 470 along the shaft 454 and to the articulation joint 458 and/or the end effector 456. These drive arrangements are merely exemplary; alternative drive arrangements for conveying forces and motion from the rotary drives 460, 462, 464, 466, 468, and 470 toward the end effector 456 are envisioned.

In various instances, it can be desirable to use a single rotary drive for applications requiring both high speed and high torque. For example, it can be desirable to maximize the speed output from a rotary drive in certain instances and to maximize the torque output from the rotary drive in other instances. A gear train can increase the speed of the rotary drive; however, such a gear train can correspondingly decrease the maximum torque that the rotary drive transmits via the gear train. In certain instances, a first rotary drive can be used for a high-torque degree of freedom (e.g. clamping of tissue) and a second rotary drive can be used for a high-speed degree of freedom (e.g. grasping of tissue). U.S. Patent Application Publication No. 2019/0201111, titled DRIVE ARRANGEMENTS FOR ROBOTIC-ASSISTED SURGICAL PLATFORMS, which published on Jul. 4, 2019, describes drive arrangements in which a first rotary drive corresponds to a "high force" degree of freedom and a second rotary drive corresponds to a "low force" degree of freedom. Relying upon two rotary drives makes both rotary drives unavailable for other simultaneous actuations and/or degrees of freedom. As a result, one fewer rotary drive is available for other degrees of freedom, such as for articulation of the end effector, for example.

The motors in the tool driver, which drive the rotary drives, can be limited to a maximum number of rotations per second. For example, a motor for the robotic tool can rotate with a maximum speed of four rotations per second, or 240 RPMs. Certain robotic stapling tools utilize a drive screw to close the jaws and/or fire fasteners therefrom. When using such a drive screw, eight to ten rotations of the drive screw may be required to close the jaws. In such instances, it can take two to three seconds to complete these rotations and fully close the jaws. Similarly, it can take two to three seconds to complete these rotations and fully open the jaws. Employing a gear train can increase the output speed and, thus, reduce the time required to open and close the jaws; however, such a gear train would also reduce the maximum torque output, which may be problematic for certain surgical functions, such as clamping, cutting, and/or firing of staples into thick and/or tough tissue. The foregoing maximum motor speed, estimated number of drive screw rotations, and time to open/close the jaws are exemplary. In other instances, motors having different motor speeds and/or different drive screw arrangements can be utilized.

In certain instances, a rotary drive can switch between a high-torque operating state and a high-speed operating state to selectively transmit higher speeds or higher torques. For example, higher speeds can be utilized during closing or grasping with the end effector jaws and higher torques can be utilized during clamping or firing of the end effector. A torque transition member in the proximal housing of a robotic tool can switch a rotary drive between high-speed gearing on a first side and high-torque gearing on a second side. In various instances, a threshold torque applied to the torque transition member can effect the transition. For example, upon reaching the threshold torque, a spring-activated ramped cam surface of the transition member can shift from the high-speed gearing toward the high-torque gearing to drivingly couple the rotary drive to the high-torque gearing and, thus transmit a high maximum torque to the output gear.

For example, a surgical tool for use with a robotic surgical system can be configured to receive rotary inputs from the robotic surgical system, and the surgical tool can include a distal end effector comprising jaws for clamping tissue therebetween, an intermediate shaft portion coupled to the distal end effector, and a proximal housing coupled to the intermediate shaft portion, the proximal housing comprising an arrangement of rotary drives comprising a first rotary drive. The first rotary drive can comprise an input shaft configured to receive a rotary input from the robotic surgical system, a transition nut slidably positioned on the input shaft, an output gear, a high-speed gear configured to selectively drive the output gear, a high-torque gear configured to selectively drive the output gear, and a spring arrangement configured to bias the transition nut along the input shaft from a high-speed operating state, in which the transition nut is in driving engagement with the high-speed gear, to a high-torque operating state, in which the transition nut is in driving engagement with the high-torque gear upon obtaining a threshold torque.

The foregoing arrangement utilizes a single rotary drive to achieve higher speeds during a first operating state and higher torques during a second operating state. As a result, the other rotary drives can be free for articulation or other surgical functions. The robotic tool can also achieve a quick or higher speed closure or grasping without requiring a quick-grasp mechanism in the jaws for speeding of the jaw closure, for example. Additionally, the torque transition feature can implement the transition between the high-speed operating state and the high-torque operating state upon receiving a threshold torque. Complex programming or mechanisms are not required to effect the transition, which can allow the jaws to open and close quickly to manipulate or grasp tissue while also delivering sufficient torque for clamping and/or cutting tissue, for example. Because robotic stapling tools typically require high-speeds to clamp the jaws onto tissue and high-torques to fire the staples and/or cut the tissue, the torque-transition feature in the tool base can seamlessly and automatically toggle between the operating states to meet the requisite torque and speed requirements in both instances.

Referring to FIGS. 7-11, a rotary drive system 500 is shown. The rotary drive system 500 is positioned in the tool base or proximal housing of a robotic tool, such as the tool base 352 of the robotic tool 350 (FIG. 5) or the tool base 452 of the robotic stapling tool 450 (FIG. 6), for example. The tool base includes a frame 590, which supports rotary motion of components of the rotary drive system 500. In such instances, the rotary drive system 500 is one of the rotary drives in the tool base and is selectively coupled to one of the rotary drivers 260, 262, 264, 266, 268, and 270 in the carriage 224 of the tool driver 220 (FIG. 4). For example, the rotary drive system 500 can correspond to one of the rotary drives 360, 362, 364, 366, 368, and 370 in the base 352 (FIG. 5) and a motor in the carriage 224 is configured to transmit rotary motion to the rotary drive system 500 during use.

As further described herein, the tool base for a robotic tool can include a different number of rotary drives, for example. Moreover, the rotary drive system 500 can be incorporated into various proximal housings and/or tool bases for different robotic tools having one or more different surgical functions, for example.

The rotary drive system 500 is configured to drive an output shaft 502. The output shaft 502 is configured to drive a rotary drive screw in certain instances. Rotation of the rotary drive screw can effect an opening and closing motion of the jaws 480, 482 (FIG. 6) to grasp and clamp tissue therebetween. Rotary drive screws are further described in U.S. Provisional Patent Application No. 63/057,430, titled SURGICAL INSTRUMENTS WITH TORSION SPINE DRIVE ARRANGEMENTS, filed Jul. 28, 2020. Rotary drive shafts are described in U.S. Patent Application Publication No. 2014/0001231, titled FIRING SYSTEM LOCKOUT ARRANGEMENTS FOR SURGICAL INSTRUMENTS, which published Jan. 2, 2014. U.S. Provisional Patent Application No. 63/057,430, titled SURGICAL INSTRUMENTS WITH TORSION SPINE DRIVE ARRANGEMENTS, filed Jul. 28, 2020 and U.S. Patent Application Publication No. 2014/0001231, titled FIRING SYSTEM LOCKOUT ARRANGEMENTS FOR SURGICAL INSTRUMENTS, published Jan. 2, 2014, are incorporated by reference herein in their respective entireties.

The rotary drive system 500 includes an input shaft 504, which is configured to receive a rotary input from the robotic surgical system. For example, a motor in the carriage 224 is configured to drive rotation of the input shaft 504 when the robotic tool is mounted to the tool driver 220 (FIG. 3). The rotary drive system 500 includes a transition nut 506 slidably positioned on the input shaft 504. As further described herein, the transition nut 506 transitions the rotary drive system 500 between a high-speed operating state (FIG. 9) and a high-torque operating state (FIG. 11) based on the torque applied to the transition nut 506. The rotary drive system 500 also includes a spring arrangement, which is configured to bias the transition nut 506 along the input shaft 504 from the high-speed operating state to the high-torque operating state. In the high-speed operating state, the transition nut 506 is in driving engagement with a high-speed gear train 521. In the high-torque operating state, the transition nut 506 is in driving engagement with a high-torque gear 530.

Figure 8:
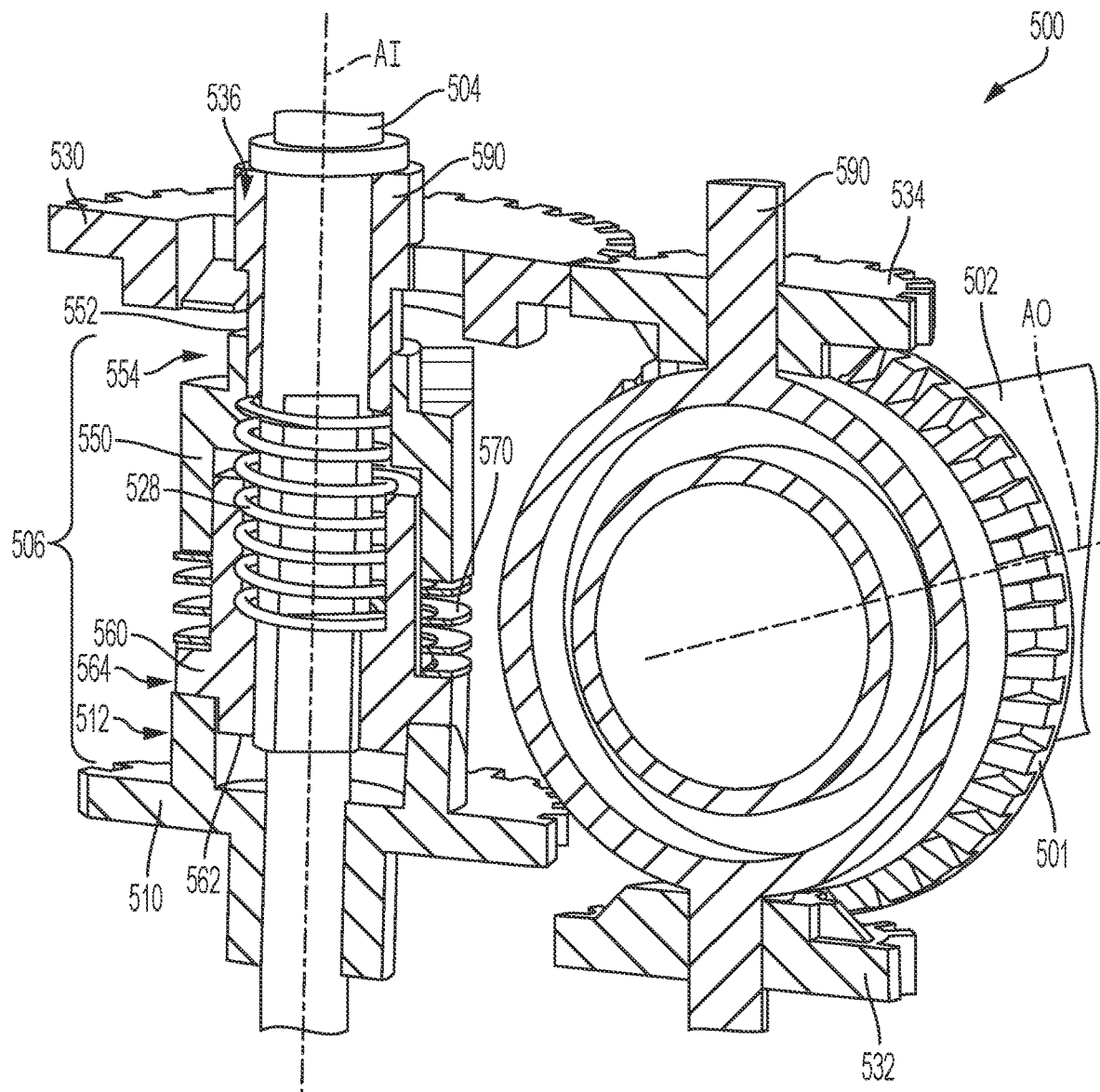
FIG. 8 is a perspective cross-sectional view of the rotary drive system of FIG. 7 with portions of the high-speed gear assembly removed for clarity, in accordance with at least one aspect of the present disclosure.
Figure 9:
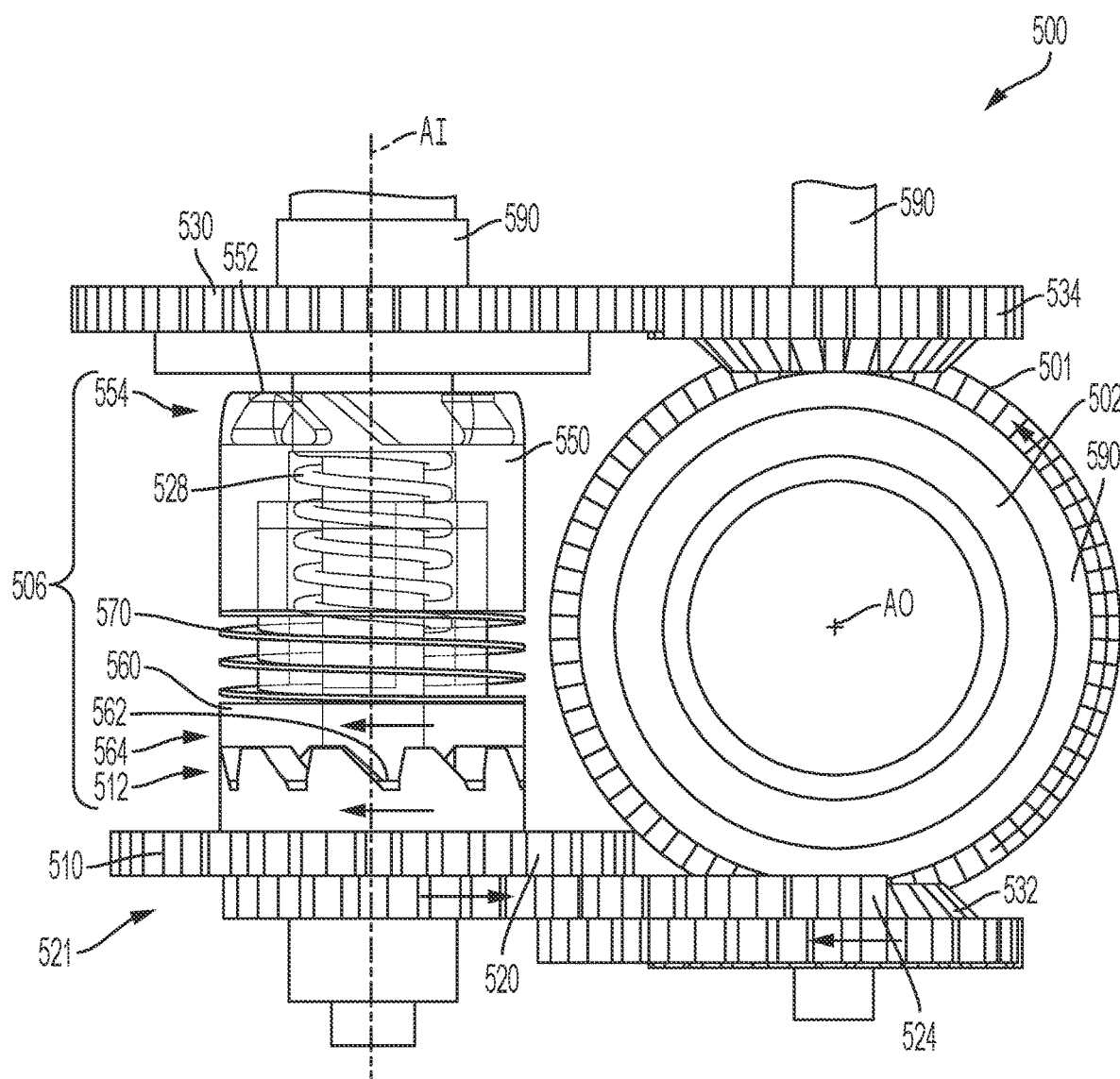
FIG. 9 is an elevation view of the rotary drive system of FIG. 7 in a high-speed operating state and with the transition nut shown as transparent to reveal component concealed therein, in accordance with at least one aspect of the present disclosure.

Referring primarily to FIGS. 8 and 9, the spring arrangement includes a biasing spring 528, which exerts a force on the transition nut 506 and pushes the transition nut 506 toward the high-speed gear train 521. The biasing spring 528 is a helical compression spring housed in an internal cavity between the frame 590 and the transition nut 506. For example, the biasing spring 528 is aligned longitudinally with the input axis AI. A first end of the biasing spring 528 abuts the second portion 560 of the transition nut 506, and a second end of the biasing spring 528 abuts the frame 590. The biasing spring 528 is positioned to bias the transition nut 506 toward the high-speed operating state. Alternative spring arrangements and geometries are contemplated.

In the depicted arrangement, the high-speed gear train 521 includes a grasping gear 510. An array of beveled teeth 512 on the grasping gear 510 extend toward the transition nut 506, as further described herein.

The high-speed gear train 521 and the high-torque gear 530 are configured to selectively drive an output gear 501. The high-speed gear train 521 includes a high-speed gear 520, along with additional gear(s) (e.g. gear 524). The gears 520 and 524 form the gear train 521, which is configured to increase the maximum output speed to the output gear 501 and, thus, the output shaft 502. The output shaft 502 is aligned longitudinally with the output axis AO. In other instances, the gear train 521 can include a different number and/or arrangement of gears, which can similarly reduce the maximum torque and increase the maximum speed that the gear train 521 can transmit to the output gear 501. For example, the gear train 521 can define a speed ratio that is greater than one and a torque ratio that is less than one. A first bevel gear 532 couples the gear train 521 and high-speed gear 520 thereof to the output gear 501. A second bevel gear 534 couples the high-torque gear 530 to the output gear 501.

The input shaft 504 drives rotation of the transition nut 506 about an input axis AI. The transition nut 506 transmits its rotation to the output gear 501 by one of the high-speed gear 520 or the high-torque gear 530. For example, the transition nut 506 includes a first portion 550 and a second portion 560 flexibly or non-rigidly spaced apart from the first portion 550 along the input axis AI by a spring 570. The spring 570 provides flexibility and bounce as the transition nut slides in/out of engagement with the gear teeth 512, for example. The first portion 550 includes a first end 552 adjacent to the high-torque gear 530. The second portion 560 includes a second end 562 adjacent to the gear train 521 and the grasping gear 510 thereof.

In the first portion 550, the transition nut 506 includes an array of sloping teeth 554 around its perimeter. The sloping teeth 554 extend to the first end 552. The sloping teeth 554 are helical ridges or external threads. For example, the sloping teeth 554 are defined by pairs of ramped or angled surfaces, which are angled relative to the axis of rotation of the transition nut 506, the input axis AI. For example, each sloping tooth 554 includes a bottom ramp, a top ramp substantially parallel to or equidistance from the bottom ramp along its length, and a top surface between the bottom ramp and the top ramp.

The sloping teeth 554 engage sloping receptacles 536 in the high-torque gear 530 when the transition nut 506 is in the high-torque operating state. The sloping receptacles 536 define a complementary geometry to the sloping teeth 554, such that each sloping receptacle 536 closely receives one of the sloping teeth 554. Moreover, the complementary sloping geometry functions as a screw—the sloping teeth 554 being external threads and the sloping receptacles 536 being internal threads—such that a "screwing" rotation of the sloping teeth 554 into the sloping receptacles 536 draws the transition nut 506 along the input axis AI and further into engagement with the high-torque gear 530. More specifically, upon engagement of the angled features 554, 536, the complementary geometry is configured to drive the transition nut 506 farther along the input shaft 504 and input axis AI toward the high-torque gear 530 such that the sloping teeth 554 are fully received in the sloping receptacles 536 and drawn into driving engagement with the high-torque gear 530. Moreover, when the rotary direction of the transition nut 506 is reversed, the complementary sloping geometry can again function as a screw such that an "unscrewing" rotation of the sloping teeth 554 relative to the sloping receptacles 536 pulls the transition nut 506 along the input axis AI away from the high-torque gear 530 and toward the high-speed gear 520.

In other instances, the high-torque gear 530 can include sloping teeth or external threads, and the first portion 550 of the transition nut 506 can including sloping receptacles or internal threads, for example.

The transition nut 506 includes an array of teeth 564 around the perimeter of the second portion 560. The teeth 564 extend to the second end 562. The teeth 564 define a substantially saw-toothed geometry and the top of each tooth 564 is narrower than the bottom. For example, each sloping tooth 564 includes a first ramped surface, a second ramped surface extending toward the first ramped surface, and a top surface between the first and second ramped surfaces. In such instances, the teeth are truncated triangular prisms, for example. Alternative teeth geometry are contemplated.

The teeth 564 engage corresponding teeth 512 in the grasping gear 510 when the transition nut 506 is in the high-speed operating state. For example, a ramped surface on each tooth 512 is configured to slide along a complementary ramped surface on a tooth 512 to move the teeth 564, 512 between an engaged and disengaged position. The biasing spring 528 is configured to bias the teeth 564 into engagement with the teeth 512. For example, in instances in which the teeth 564 and 512 are not precisely aligned when moving into engagement, the spring 570 can ease the transition between the different operating states. In various instances, the spring 528 may also ease the transition between operating states, such as when the angular direction is reversed by a motor to reverse the rotary direction of the drive screw and retract the firing member, for example, and the torque-based transition nut 506 disengages the high-torque gear 530 and moves into engagement with the high-speed gear 520, for example.

Figure 10:
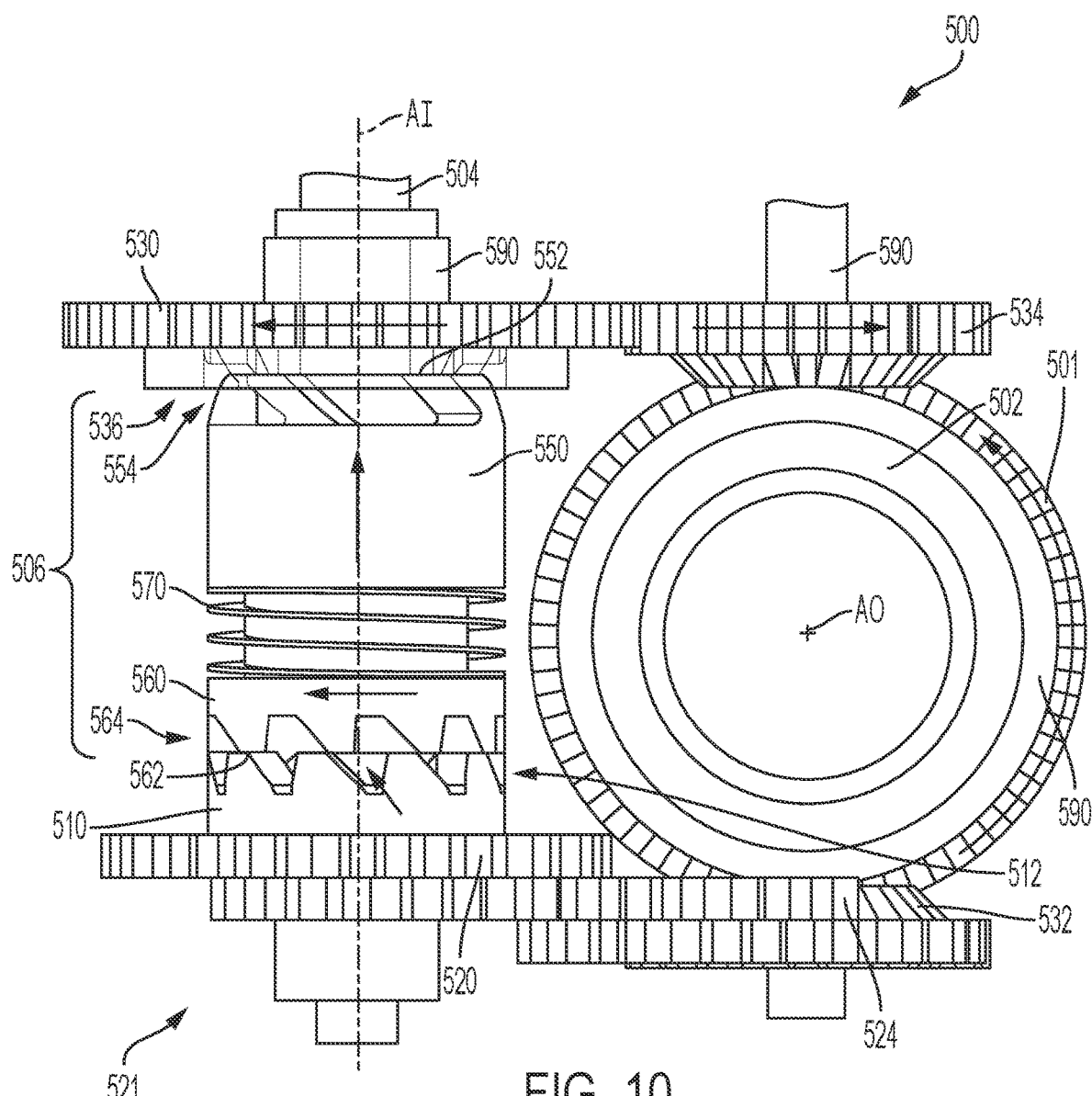
FIG. 10 is an elevation view of the rotary drive system of FIG. 7 in a transitional state and with portions of a high-torque gear shown as transparent to reveal an internal array of sloping recesses, in accordance with at least one aspect of the present disclosure.
Figure 11:
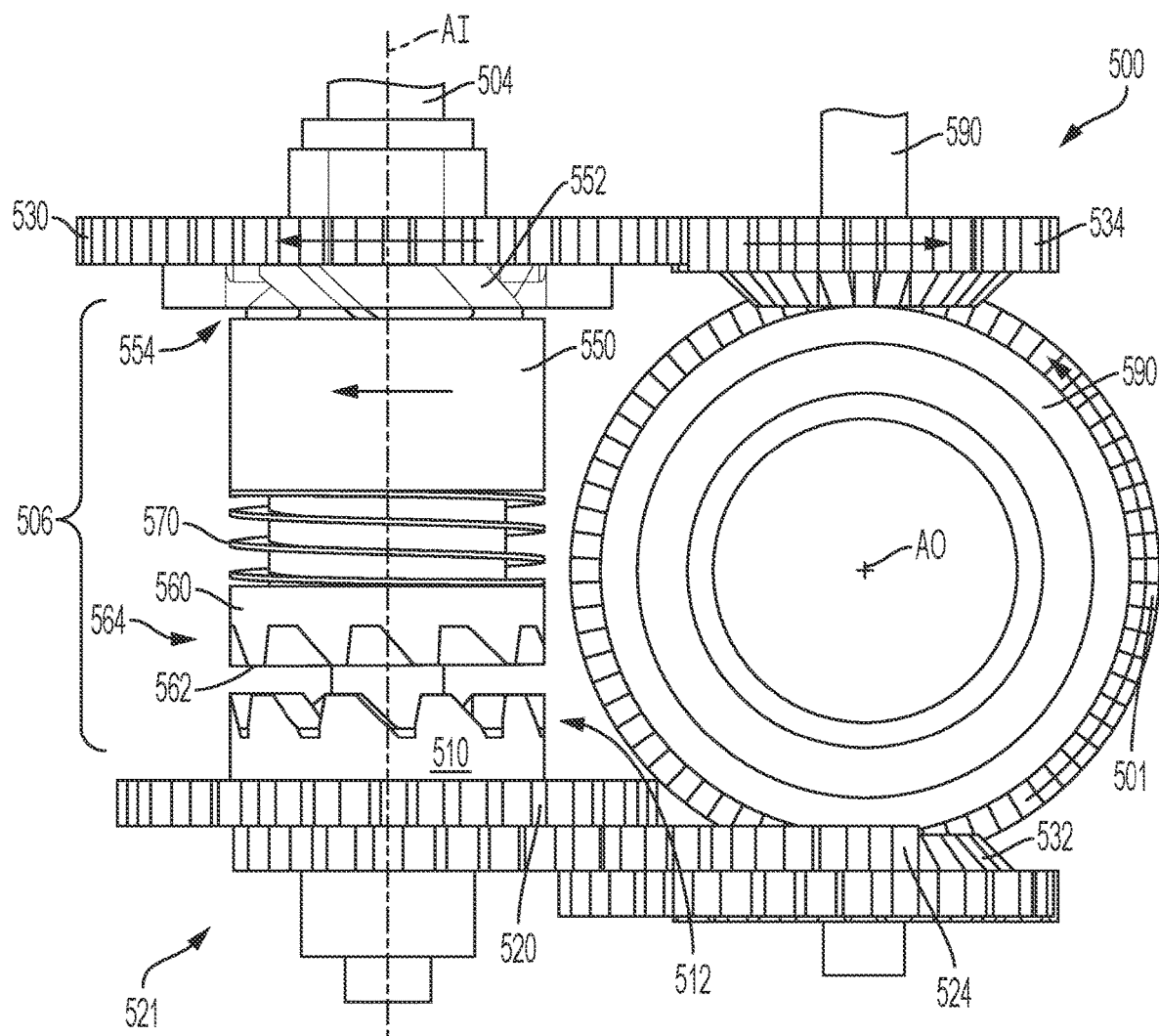
FIG. 11 is an elevation view of the rotary drive system of FIG. 7 in a high-torque operating state and with portions of the high-torque gear shown as transparent to reveal the internal array of sloping recesses, in accordance with at least one aspect of the present disclosure.

The transitioning operation of the rotary drive system 500 is depicted in FIGS. 9-11. FIG. 9 depicts a high-speed operating state of the rotary drive system 500. Though this operating state is referred to as a high-speed operating state, the reader will appreciate that the maximum speed depends on a number of factors, such as properties of the motor, for example. The high-speed operating state, however, can be designed and optimized to output a higher maximum speed to the output gear 501 than the high-torque operating state. In other words, the maximum speed can be a "high-speed" relative to the maximum speed in the high-torque operating state.

FIG. 11 depicts a high-torque operating state of the rotary drive system 500. The torque output to the output gear 501 during the high-torque operating state also depends on a number of factors including properties of the motor, for example. The high-torque operating state, however, can be designed and optimized to output a higher maximum torque to the output gear 501 than the high-speed operating state. In other words, the maximum torque can be a "high-torque" relative to the maximum torque in the high-speed operating state.

FIG. 10 depicts a transition between the high-speed operating state and the high-torque operating state.

Referring again to FIG. 9, the spring 528 has biased the transition nut 506 into engagement with the high-speed gear train 520. Specifically, the biasing spring 528 exerts a force upon the transition nut 506 along the input axis AI and in the direction of the high-speed gearing, i.e., toward the grasping gear 510 of the gear train 521. The array of teeth 564 on the second portion 560 meshingly engage the array of teeth 512 on the grasping gear 510.

In this arrangement, rotary motion of the input shaft 504 (provided by a motor in the tool driver, for example) is transmitted to the transition nut 506, which rotates the grasping gear 510 to effect rotation of the gear train 521. The gear train 521 is configured to increase the maximum speed such that the maximum speed delivered to the output gear 501 via the first bevel gear 532 is optimized for high-speed applications. For example, the high-speed output can be utilized for the closing of the jaws to grasp and manipulate tissue. Arrows showing exemplary rotary directions for the transition nut 506, the grasping gear 510, the gear train 521 gears, and the output gear 501 are included in FIG. 9.

Referring now to FIG. 10, when the torque applied to the transition nut 506 exceeds a threshold value, the torque at least partially overcomes the spring force of the spring arrangement. The array of teeth 564 on the second portion 560 of the transition nut 506 are configured to ride or slide along the complementary ramped surfaces of the array of teeth 512 on the grasping gear 510 as the transition nut 506 rotates and moves along the input axis AI toward the high-torque gearing, i.e. the high-torque gear 530. Compression of the biasing spring 528 when the torque reaches the threshold value shifts the transition nut 506 out of engagement with the grasping gear 510. Moreover, as the grasping gear 510 releases the transition nut 506 from meshing or driving engagement, the array of sloped teeth 554 on the first portion 550 of the transition nut 506 engage the sloped receptacles 536 in the high-torque gear 530. Upon engagement, the sloped receptacles 536 can "grip" or "grab" the transition nut 506 to draw the teeth 554 farther into the receptacles 536 into the arrangement shown in FIG. 11, in which the transition nut 506 is completely disengaged from the grasping gear 510 and fully engaged with the high-torque gearing.

In the high-torque operating state of FIG. 11, rotary motion of the input shaft 504 (provided by a motor in the tool driver, for example) is transmitted to the transition nut 506, which rotates the high-torque gear 530. The high-torque gear 530 is configured to optimize the torque delivered to the output gear 501 via the second bevel gear 534. Specifically, the torque is optimized for high-torque applications, such as clamping of tissue by an end effector. Arrows showing exemplary rotary directions for the transition nut 506, the high-torque gear 530, and the output gear 501 are included in FIG. 11.

At the end of the firing stroke, the drive arrangement is configured to reverse the firing member. For example, the drive arrangement can reverse the angular direction of the transition nut 506 to retract the firing member. The reversal of the transition nut 506 can correspond to an "unscrewing" rotation of the transition nut 506, such that the transition nut 506 is displaced along the input axis AI away from the high-torque gear 530. In such an arrangement, a return stroke of the firing member and associated reversal of the transition nut 506 and output gear 501 can automatically transition the drive arrangement to the high-speed operating state.

Owing to the geometry of the high-torque gear 530 and the second bevel gear 534, the high-torque operating state can increase the torque supplied to the output gear 501 by eight times the torque of the high-speed operating state. In other instances, the torque output can be doubled, or quadrupled, for example. Variations to the number, size, and arrangement of gears between the high-torque gear 530 and the output gear 501 can further increase the torque output.

Owing to the geometry of the gear train 521 and the first bevel gear 532, the high-speed operating state can increase the speed supplied to the output gear 501 by four times the speed in the high-torque operating state. In other instances, the torque output can be doubled or increased by eightfold, for example. For example, additional speed gears in the gear train 521 can further increase the speed output. Variations to the number, size, and arrangement of gears between the high-speed gear 520 and the output gear 501 can further increase the speed output.

In various instances, robotic tools rely on software incorporated into the operating system and the processor of the robotic surgical system to mitigate risks and avoid failures. Redundant systems and/or crosschecks may control certain robotic tools that perform high-severity tasks to mitigate the risks associated with those tasks. For example, clamping can be a high-severity task because insufficient clamping can result in an increased likelihood and/or greater incidences of staple malformation and, thus, insufficient tissue sealing, in certain instances. For example, robotic stapling tools that clamp and/or cut tissue can rely on redundant systems (e.g. mechanical and electrical lockouts) and various crosschecks to ensure the closure motions, clamping forces, and firing strokes meet predefined standards and/or thresholds. Various crosschecks may increase the costs and/or the complexity of the system, and may require additional maintenance and user-support over time. In certain instances, crosschecks for surgical tools and/or surgical functions that do not add unnecessary cost and complexity to the system may be beneficial.

Certain robotic tools utilize multiple motors for certain surgical functions. For example, a robotic stapling tool can utilize dual motors for advancing a closure member, performing the closure stroke, and/or clamping tissue. A crosscheck that relies on a dual-motor closure system to create crosscheck algorithms can mitigate risks and avoid failures related to high-severity clamping errors, for example.

For example, a robotic surgical system can include a closure system including a first pinion drivingly coupled to a first motor, a second pinion drivingly coupled to a second motor, and a closure gear selectively driven by the first pinion and the second pinion. The robotic surgical system can further include a control circuit configured to implement a motor crosscheck operation in which the control circuit is configured to receive a first parameter indicative of a first torque generated by the first motor, receive a second parameter indicative of a second torque generated by the second motor, compare the first parameter to the second parameter, and transmit a signal to a communication device, wherein the signal is based on the comparison and indicative of a status of the closure system.

In various instances, the control circuit of such a robotic surgical system can also be configured to determine when the closure system has achieved a steady state in the motor crosscheck operation, and to compare the first parameter to the second parameter after the closure system has achieved the steady state.

The motor crosscheck operation can proceed after a homing operation and/or after a clamping event.

Such a robotic surgical system may mitigate certain risks and avoid failures related to high-severity clamping errors. Moreover, such crosschecks can improve the operation of the surgical tool without necessitating redundant motor controls and/or requiring dedicated safety processing units, for example.

Figure 12:
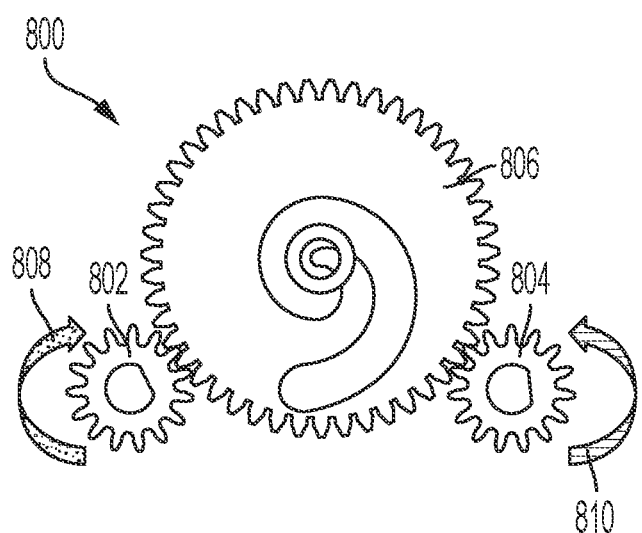
FIG. 12 is a schematic of a dual drive arrangement for a robotic surgical tool implementing a crosscheck procedure, in accordance with at least one aspect of the present disclosure.

FIG. 12 shows an example drive arrangement 800. The drive arrangement 800 is used to clamp the jaws of an end effector, such as the jaws 480 and 482 of the end effector 456 (FIG. 6), for example. In other instances, a robotic surgical system can utilize the drive arrangement for additional and alternative surgical functions, such as firing fasteners into tissue and/or severing tissue, for example. The drive arrangement 800 includes a first pinion 802 and a second pinion 804. A motor and corresponding rotary drive are configured to drive the pinions 802, 804. For example, each of the driving pinions 802 and 804 can be driven by one of the motors and one of the corresponding rotary drivers 260, 262, 264, 266, 268, and 270 in the tool driver 220 (FIG. 4) in certain aspect of the present disclosure.

The pinions 802 and 804 drive the closure gear 806, which effects the closure motion of the end effector. The torques on the pinions 802 and 804 and, in certain instances, the torque applied to the closure gear 806 can be monitored and compared during a crosscheck procedure to determine if the drive arrangement 800 is operating properly or is in a fault state, for example. The robotic surgical system can implement the crosscheck procedure at various times during the lifecycle and/or usage cycles of the robotic tool. For example, each time the robotic tool is mounted to the tool drive on the robotic arm, one or more crosscheck procedures can be implemented. Additionally or alternatively, in certain instances, the robotic surgical system can implement a crosscheck at the completion of a homing operating and/or each closure event (e.g. closure stroke). For example, when a robotic tool is mounted to a tool driver, the robotic system can undergo a homing operation, in which positions of the various components are determined and recorded to ascertain various limits of the system. Homing operations are further described in U.S. patent application Ser. No. 16/553,725, titled ARTICULATING INCLUDING ANTAGONISTIC CONTROLS FOR ARTICULATION AND CALIBRATION, filed Aug. 28, 2019, for example. In certain instances, a clinician can selectively implement a crosscheck and/or override a suggested crosscheck operation.

In one example, to conduct a crosscheck procedure for the robotic tool, the first driving pinion 802 is rotated in a first direction indicated by the arrow 808 (clockwise in the view in FIG. 12) and the second driving pinion 804 is rotated in a second direction indicated by the arrow 810 (counterclockwise in the view of FIG. 12). The first direction is opposite the second direction. Owing to the arrangement of the driving pinions 802 and 804 relative to the closure gear 806, when the driving pinions 802, 804 rotate in opposite or opposing directions, the closure gear 806 may rock, sway, or otherwise move within the backlash defined by the gear teeth. For example, the closure gear 806 may rattle when touched owing to the backlash permitted by the gear teeth.

Figure 13:
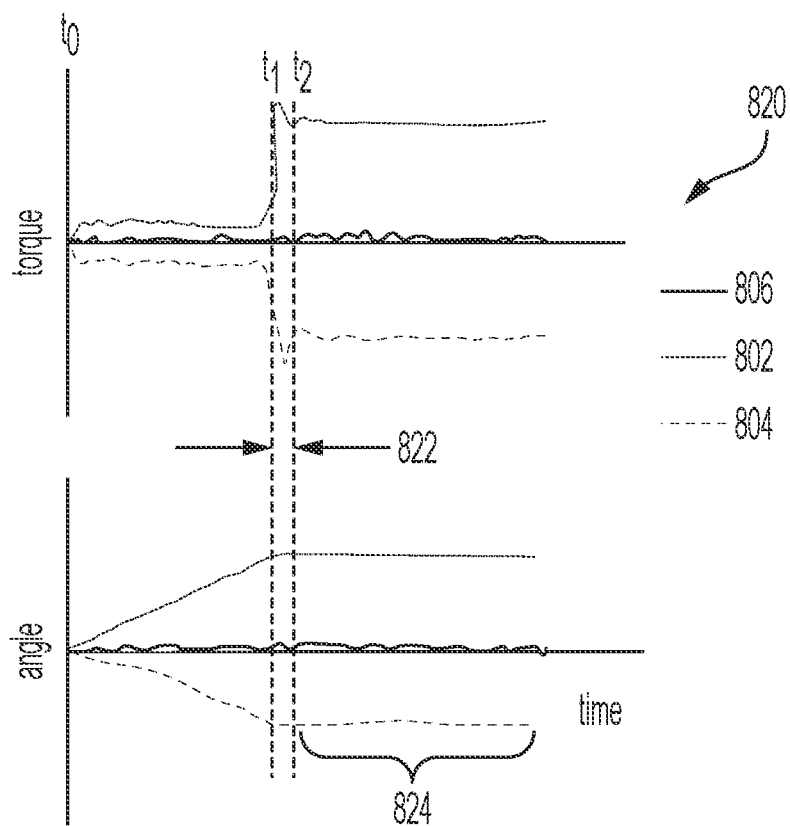
FIG. 13 is a graphical representation of angular displacement and torque over time for the crosscheck procedure of FIG. 12, in accordance with at least one aspect of the present disclosure.

A graphical representation 820 of torque and angular displacement over time for the drive arrangement 800 is shown in FIG. 13. From time t0 to t1, the closure gear 806 can shift or rattle within the backlash defined by the gear teeth. When the driving pinions 802, 804 run out of backlash, they import torque on each other at time t1 and continue to exert counter-exerted torques upon each other through a dynamic region 822 during which the absolute torque values fluctuate/vacillate. After the dynamic region 822, the drive arrangement 800 enters a steady-state region 824 at time t2 during which the torques measured by the driving pinions 802, 804 may substantially level out and define fewer fluctuations over time. One or more metrics can be utilized to determine and/or compute when the driving pinions 802 and 804 achieve steady-state status and enter the steady-state region.

The torque for each driving pinion 802 and 804 can be monitored during the crosscheck procedure. For example, a control circuit can monitor and compare the torques throughout the steady-state region 824. If the magnitudes of the opposing torques are close to each other—i.e. within some predefined threshold value—the control circuit can conclude that the torque values can be trusted. However, if the magnitudes of the opposing torques are not significantly close to each other—i.e. outside a predefined threshold difference—the robotic surgical system can enter an error or fault state. For example, the robotic surgical system can determine the robotic tool is in a fault state. The robotic surgical system can alert the user to the error/fault state and/or can implement one or more lockouts (absolute and/or discretionary) upon entering the error/fault state. In certain instances, the error/fault state may require a recalibration and/or re-inspection of the robotic tool.

Figure 14:
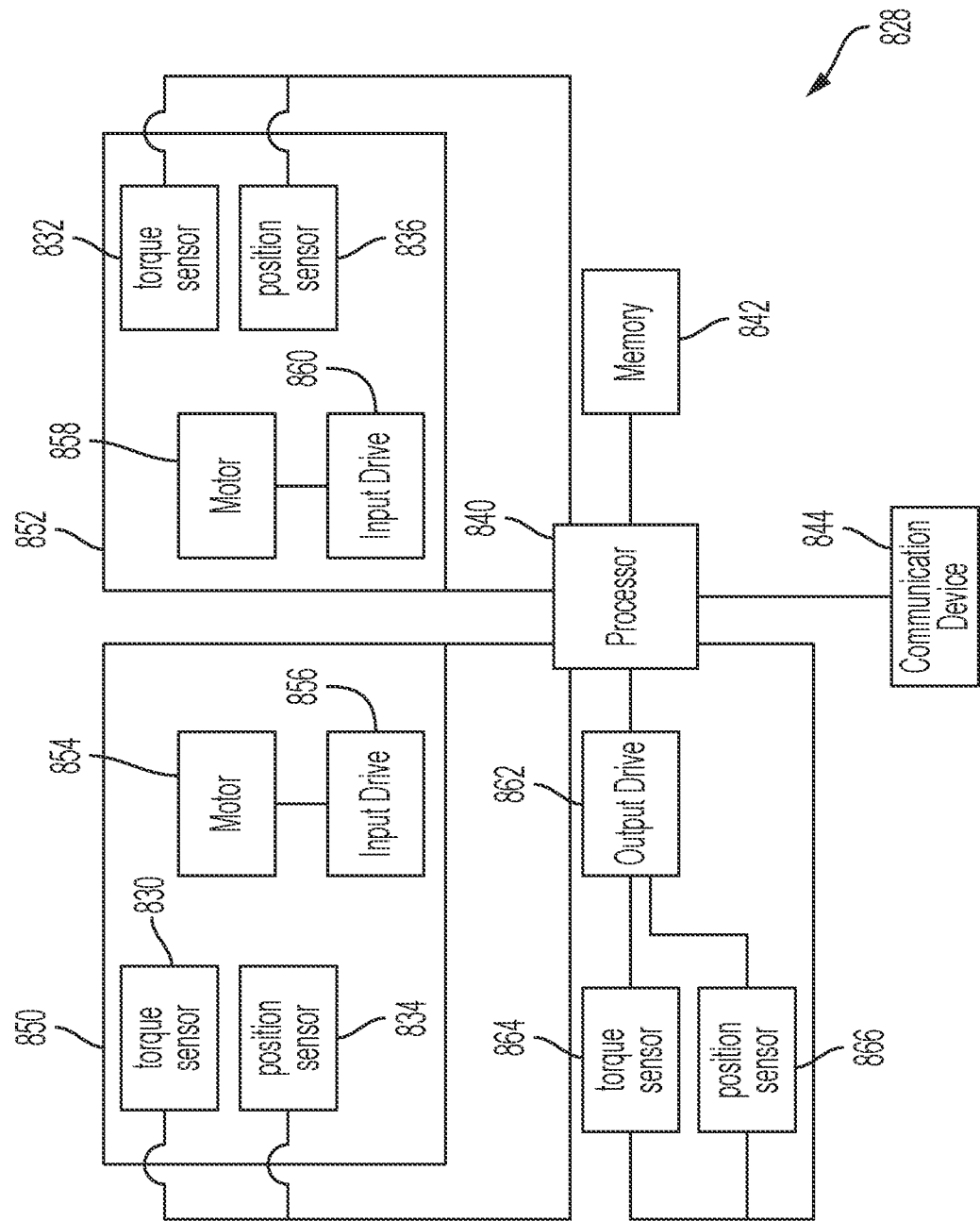
FIG. 14 is a schematic of a control circuit for use with the drive arrangement of FIG. 12, in accordance with at least one aspect of the present disclosure.

A control circuit 828 for a dual driving pinion arrangement, such as the drive arrangement 800 (FIG. 12), for example, is shown in FIG. 14. The control circuit 828 includes a processor 840 in signal communication with a memory 842 and with a communication device 844. A first drive system 850 and a second drive system 852 are in signal communication with the processor 840. The first drive system 850 includes a motor 854, an input drive 856 coupled to the motor 854, a torque sensor 830, and a rotary encoder/position sensor 834. The input drive 856 can correspond to the first pinion gear 802 (FIG. 12) in the drive arrangement 800, for example. The second drive system 852 includes a motor 858, an input drive 860 coupled to the motor 858, a torque sensor 832, and a rotary encoder/position sensor 836. The input drive 860 can correspond to the second pinion gear 804 (FIG. 12) in the drive arrangement 800, for example. In such instances, the torque sensors 830 and 832 determine the torque on the first driving pinion 802 and the second driving pinion 804, respectively. Moreover, the position sensors 834 and 836 determine the angular position of the first driving pinion 802 and the second driving pinion 804, respectively.

The control circuit 828 also includes an output drive 862, a torque sensor 864 and a rotary encoder/position sensor 866 therefor. The output drive 862 can correspond to the closure gear 806 (FIG. 12) in the drive arrangement 800, for example. In such instances, the torque sensor 864 determines the output torque applied to the closure gear 806, and the position sensor 866 determines the angular position of the closure gear 806.

During the crosscheck procedure, the torque sensors 830, 832 and the position sensors 834, 836 are configured to transmit signals to the processor 840 indicative of the torque and angular position of the input drives 856, 860. The torque sensor 864 and the position sensor 866 can also be in signal communication with the processor 840 and configured to transmit signals thereto indicative of the torque and the angular position of the output drive 862. The torques detected by the torque sensors 830, 832, and 864 and transmitted to the processor 840 are monitored over time and can be recorded in the memory 842.

In various instances, the processor 840 is configured to determine when the dual driving pinion system has achieved steady-state and, in the steady-state operating state, to compare the input torques detected by torque sensors 832 and 834. If the comparison between the absolute torques determined by the torque sensors 832 and 834 exceeds a threshold value, the control circuit 828 is configured to enter a fault state. Operations for the fault state are stored in the memory 842 and implemented by the processor 840 and include, for example, providing an output signal to the clinician or to another surgical system with a communication device 844 and/or implementing one or more lockouts to protect the integrity of the robotic tool and safety of the patient.

Figure 15:
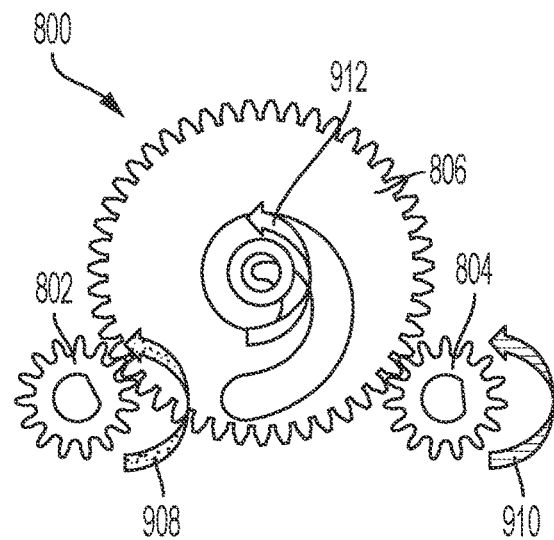
FIGS. 15 and 16 are schematics of the dual drive arrangement of FIG. 12 implementing a crosscheck procedure, in accordance with at least one aspect of the present disclosure.
Figure 16:
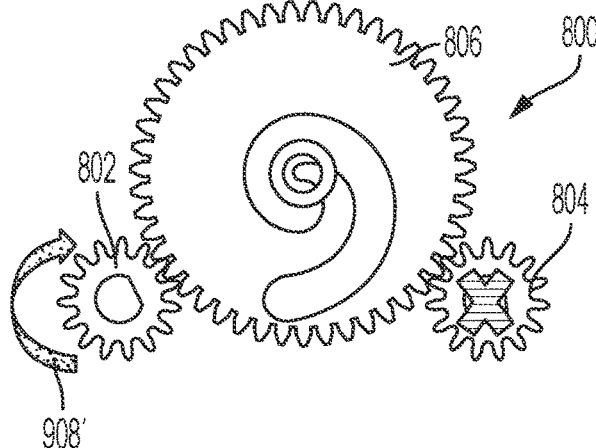
Figure 17:
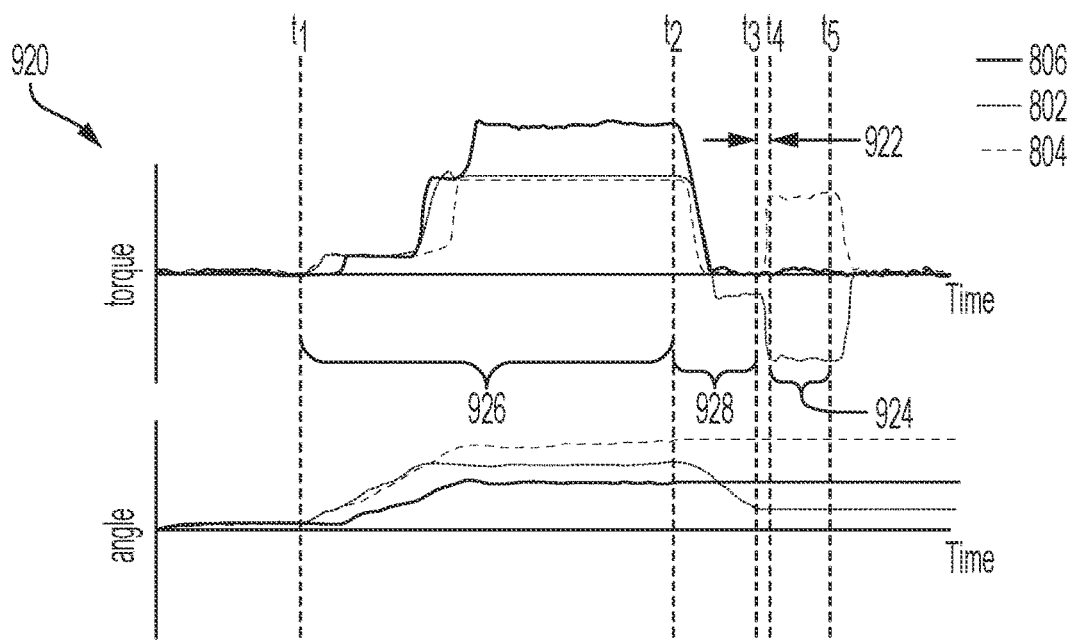
FIG. 17 is a graphical representation of angular displacement and torque over time for the crosscheck procedure of FIGS. 15 and 16, in accordance with at least one aspect of the present disclosure.

Another crosscheck operation for a robotic tool is shown in FIGS. 15-17. In various instances, the crosscheck operation of FIGS. 15-17 can be employed with the drive arrangement 800 and the control circuit 828. To conduct this crosscheck operation, the first driving pinion 802 is rotated in a first direction indicated by the arrow 908 (counterclockwise in the view in FIG. 15) and the second driving pinion 804 is also rotated in the first direction indicated by the arrow 910 (counterclockwise in the view of FIG. 15). Owing to the arrangement of the driving pinions 802 and 804 relative to the closure gear 806, the rotation of the driving pinions 802, 804 in the first direction is also configured to rotate the closure gear 806 in the first direction (counterclockwise in the view of FIG. 15) as well, as indicated by the arrow 912, for example. In such instances, the driving pinions 802 and 804 work together to rotate the closure gear until the closure gear completes the full closure stroke. The full closure stroke is typically completed when clamping tissue or during a "homing" operation, for example.

Referring primarily now to FIG. 16, the torque on the driving pinions 802 and 804 is then relieved upon reaching a bottomed-out state. Thereafter, one driving pinion can be configured to hold its position during a crosscheck operation, while the other pinion drives against it through the output gear 806. For example, the first pinion gear 802 can seek to rotate in a second direction indicated by the arrow 908' (clockwise in the view of FIG. 16), which is opposite to the first direction of the arrow 908 in FIG. 15, while the second pinion gear 804 resists rotation. In such instances, the first pinion gear 802 moves through the backlash region defined between the meshed gear teeth and, then, the pinion gears 802 and 804 have opposing torques, which can be monitored and compared during the crosscheck operation.

A graphical representation 920 of torque and angular displacement over time for the drive arrangement 800 and the crosscheck sequence depicted in FIGS. 15 and 16 is shown in FIG. 17. At time t1, the closure stroke is initiated during which the driving pinions 802 and 804 cooperatively drive the closure gear 806 through the closure region 926. In the closure region 926, the torque and the angular displacement of the pinions 802, 804 and the closure gear 806 increases. At time t2, the closure stroke is completed and the torque on the closure gear 806 is relieved.

The driving torques are relieved and at time t2 the first pinion 802 reverses direction (FIG. 16) and then moves through the backlash defined by the meshing gear teeth during the region 928. For the crosscheck operation, a dynamic region 922 is followed by a steady-state region 924, similar to the dynamic region 822 and the steady-state region 824 (FIG. 13), respectively, for example. In the crosscheck operation of FIG. 17, the torque on the first pinion gear 802 continues to a non-zero absolute torque. As the first pinion gear 802 generates a non-zero absolute torque, the second pinion 804 generates an opposing torque at time t3, which marks the beginning of the dynamic region 922. In the dynamic region 922, the absolute torque values of the first pinion 802 and the second pinion 804, which are in opposing directions, increase. Upon reaching the steady-state region 924 at time t4, the absolute torques on the driving pinions 802 and 804 maintain substantially constant values opposing each other. At time t5, the steady-state region 924 ends and the crosscheck procedure has been completed.

The opposing torques for each driving pinion 802 and 804 can be monitored during the crosscheck procedure of FIGS. 15-17. For example, the torques can be monitored and compared during the steady-state region 924. If the magnitudes of the opposing torques are close to each other—i.e., within some predefined threshold value—the control circuit can conclude that the torque values can be trusted. However, if the magnitudes of the opposing torques are not significantly close to each other, the robotic surgical system can enter an error or fault state. For example, the robotic surgical system can determine the robotic tool is in a fault state. The robotic surgical system can alert the user to the error/fault state and/or can implement one or more lockouts (absolute and/or discretionary). In certain instances, the fault state may require a recalibration and/or re-inspection of the robotic tool.

Additionally or alternatively, the crosscheck procedure can monitor the angular travel of the pinion gears 802, 804 from the end of the closure stroke at time t2 to the beginning of the steady-state region 924 at time t4. The angular travel is the difference between the first plateau indicating angular displacement for the first driving pinion 802 and the second plateau indicating angular displacement for the first driving pinion 802. In other words, the first driving pinion 802 rotates from a first position at the end of the closure stroke 926 to a second position at the beginning of the steady-state region 924, and the difference in angular position can be compared to the stored backlash value. The backlash value can be measured during manufacturing and stored in the memory of the robotic tool and/or robotic surgical system, for example. If the angular travel of the first driving pinion 802 does not match the stored backlash value, within some threshold, the processor can signal an error or fault state. Conversely, if the angular travel is sufficiently close to the stored backlash value, the processor can transmit a signal indicating the robotic tool has passed the check.

In various instances, the foregoing sequence can be repeated with the second pinion gear 804 switching rotary direction while the first pinion gear 802 seeks to maintain a constant angular position. The opposing torque values and the angular travel of the second driving pinion 804 during the "homing" operating can be monitored and compared, as further described herein with respect to the first driving pinion 802, for example.

Figures 18, 19:
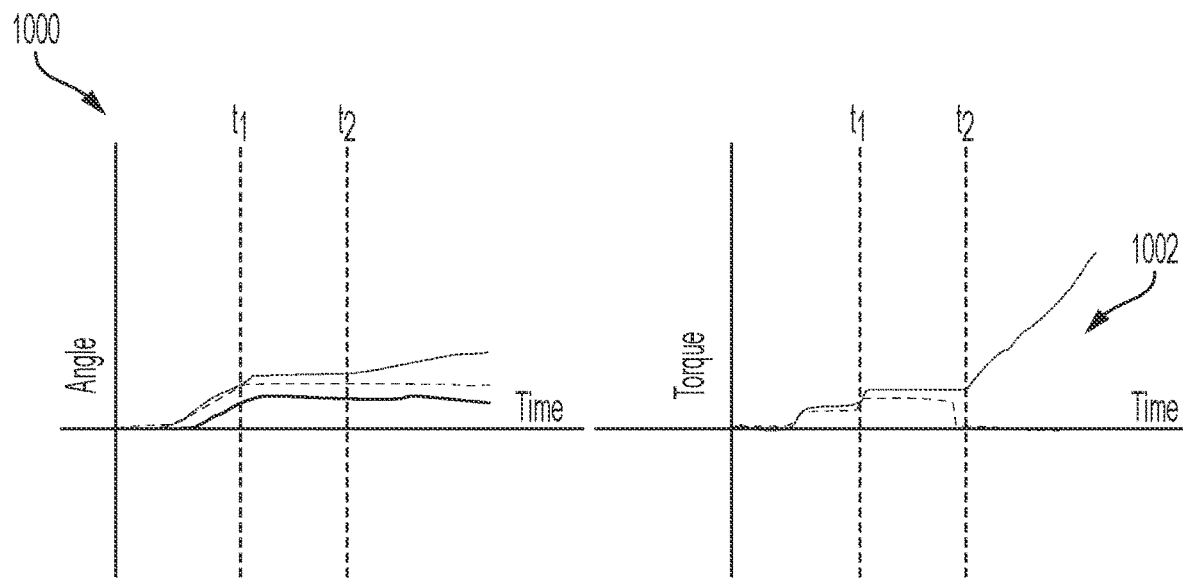
FIG. 18 is a graphical representation of angular displacement over time for a crosscheck procedure, in accordance with at least one aspect of the present disclosure.
FIG. 19 is a graphical representation of torque over time for the crosscheck procedure of FIG. 18, in accordance with at least one aspect of the present disclosure.
Figure 20:
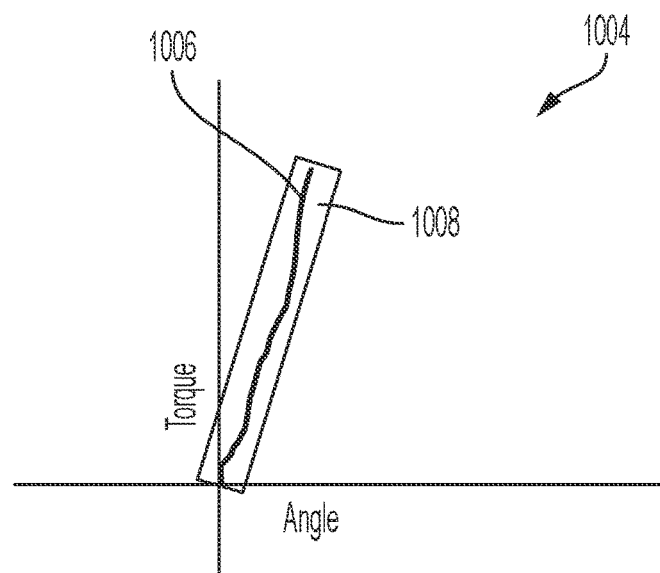
FIG. 20 is a graphical representation of the torque of FIG. 19 relative to the angular displacement of FIG. 18 for the crosscheck procedure of FIGS. 18 and 19, in accordance with at least one aspect of the present disclosure.

Another crosscheck operation for a surgical tool is shown in FIGS. 18-20. In various instances, the crosscheck operation of FIGS. 18-20 can be employed with the drive arrangement 800 and the control circuit 828. In FIG. 20, a stiffness of one of the driving pinions 802, 804 can be compared to a stored stiffness value to determine if the driving pinion 802, 804 passes the crosscheck. A stiffness 1006 plotted in a graphical representation in FIG. 20 reflects the angular position and torque measurements in FIGS. 18 and 19, respectively.

More specifically, the angular position of the driving pinions 802, 804 and the closure gear 806 (FIG. 15) over time is shown in the graphical representation 1000 in FIG. 18. The torque on the driving pinions 802, 804 over time is shown in the graphical representation 1002 in FIG. 19. Initially, as described herein with respect to FIG. 15, the driving pinions 802 and 804 work together to collectively rotate the closure gear 806 until the closure gear completes the full closure stroke at time t1. Thereafter, the closure gear 806 can be bottomed-out such that further rotation of the closure gear 806 is prevented after time t1. To conduct the crosscheck operation, one of the driving pinions 802, 804 can apply further torque to the bottomed-out closure gear 806 while the other driving pinion floats or hovers within the backlash regions of the gear teeth. In the example of FIGS. 18 and 19, the first pinion gear 802 continues to apply torque to the closure gear 806 at time t2, while the second pinion gear 804 is allowed to move or shift through the backlash.

In such an arrangement, the closure gear 806 cannot rotate any further; however, the stiffness 1006 (FIG. 20) of the first driving pinion 802 in applying torque to the closure gear 806 can be calculated based on the torque and position measurements after time t2, when the first driving pinion 802 continues to apply torque to the closure gear 806. A plot of the stiffness 1006 relative to a two-dimensional stiffness threshold 1008 in the graphical representation 1004 conveys the comparison conducted in the crosscheck operation. For example, if the stiffness 1006 falls outside the stiffness threshold 1008, the system can indicate an error or fault state.

In various instances, the stiffness threshold 1008 can be defined by a slope of the stiffness for torque over angular displacement plus and minus a value corresponding to a threshold amount, percentage, and/or standard deviation, for example.

In various instances, the foregoing sequence can be repeated with the second pinion gear 804 continuing to apply torque to the closure gear 806 while the first pinion gear 802 freewheels. The stiffness of the second pinion gear 804 can be compared to a threshold stiffness to determine an error or fault state of the second pinion gear 804.

In various instances, one or more of the various crosscheck procedures can be implemented after a homing operation and/or clamping event for a dual motor closure system. The crosscheck procedures can check the integrity of the system and motors thereof without requiring redundant motor controllers or dedicated safety processing units, for example. In such instances, the dual motor closure system can be crosschecked without adding additional cost and/or complexity. The reader will further appreciate that such a crosscheck procedure can be performed with respect to other dual motors systems for a robotic surgical tool in certain instances.

In certain instances, a robotic surgical tool having an articulation joint may define an articulation range of motion with hard stops or mechanical limits at the ends of the articulation range of motion. For example, an interference at the mechanical limit can prevent further motion beyond the mechanical limit and outside the articulation range of motion. Upon reaching the end of the articulation range of motion, the articulation joint can bump into the mechanical limit. Driving articulation of the robotic surgical tool against the mechanical limit(s) at the end of the articulation range of motion may damage the robotic surgical tool and/or the articulation system thereof over time in certain instances. Damage to the robotic surgical tool can be a function of the impact force, velocity and/or torque of the rotary drive inputs, for example.

In certain instances, to avoid bumping the mechanical limit, a control circuit can control the articulation system such that the articulation joint is limited to move within a narrower range of motion than the full articulation range of motion. For example, the mechanical limits of the articulation range of motion can be stored in the memory and/or obtained during a homing operation. The articulation system may effectively reduce the operating range of the articulation joint to less than the full articulation range of motion to maintain a safety zone or range of motion away from the mechanical limit(s). The safety zone can be configured to account for measurement error in the articulation joint during the homing operation and/or variations to the joint over time, for example. A safety zone reduces the available range of motion of the articulation joint and, thus, may unduly limit the articulation range of motion of the robotic surgical tool in certain instances.

Alternatively, it can be advantageous in certain instances to maximize the articulation range of motion and move the articulation joint within the full articulation range of motion and up to the mechanical limits while minimizing damage to the robotic surgical tool or articulation mechanism thereof. Such an articulation drive mechanism can be sufficiently robust to drive the articulation joint through its full range of motion up to the mechanical limit(s). For example, the articulation drive system may be configured to detect regions in the articulation range where the device is close to the mechanical limit and regions that are farther from the mechanical limit. Additionally, the articulation drive mechanism may operate the articulation joint differently in the regions closer to the mechanical limit to avoid damaging the articulation mechanism while still functioning fully and efficiently. For example, when the articulation joint angle is in a range of motion farther from the mechanical limit, the articulation joint may operate at a full speed and/or torque. When the articulation joint angle is in a range of motion closer to the mechanical limit, the articulation joint may operate at a limited speed and/or a limited torque. The limited speed and/or torque can allow the articulation joint to approach the mechanical limit and bump the limit softly or gently to avoid damaging the articulation mechanism. Stated differently, the articulation joint can softly bump the mechanical limit of the articulation joint and, thus, minimize wear and/or damage to the drive mechanism and/or to the articulation joint from the contact, for example.

In one aspect the present disclosure, a control circuit for use with a robotic surgical system can be configured to receive a parameter indicative of a rotary position of an articulation motor that is configured to drive an articulation joint of a robotic surgical tool. The articulation motor can be configured to move through a first range of positions and a second range of positions. The first range of positions and the second range of positions can be non-overlapping ranges. The control circuit can also be configured to implement a first operating state, and implement a second operating state when the parameter corresponds to a transition of the articulation motor from the first range of positions to the second range of positions. The second operating state can be different than the first operating state. The control circuit can be further configured to re-implement the first operating state when the parameter corresponds to a return of the articulation motor from the second range of positions into the first range of positions by a threshold anti-dither angle.

In certain instances, the foregoing articulation drive mechanism can provided a greater range of motion than articulation systems in which the articulation motion is confined to outside the safety zones defined in regions adjacent to the mechanical limits. Such an articulation drive mechanism can reduce incidences of crashing into the mechanical limit at significant speeds and/or torques, which avoids producing high impact loads that may damage the articulation system and/or robotic surgical tool, for example.

Figure 21:
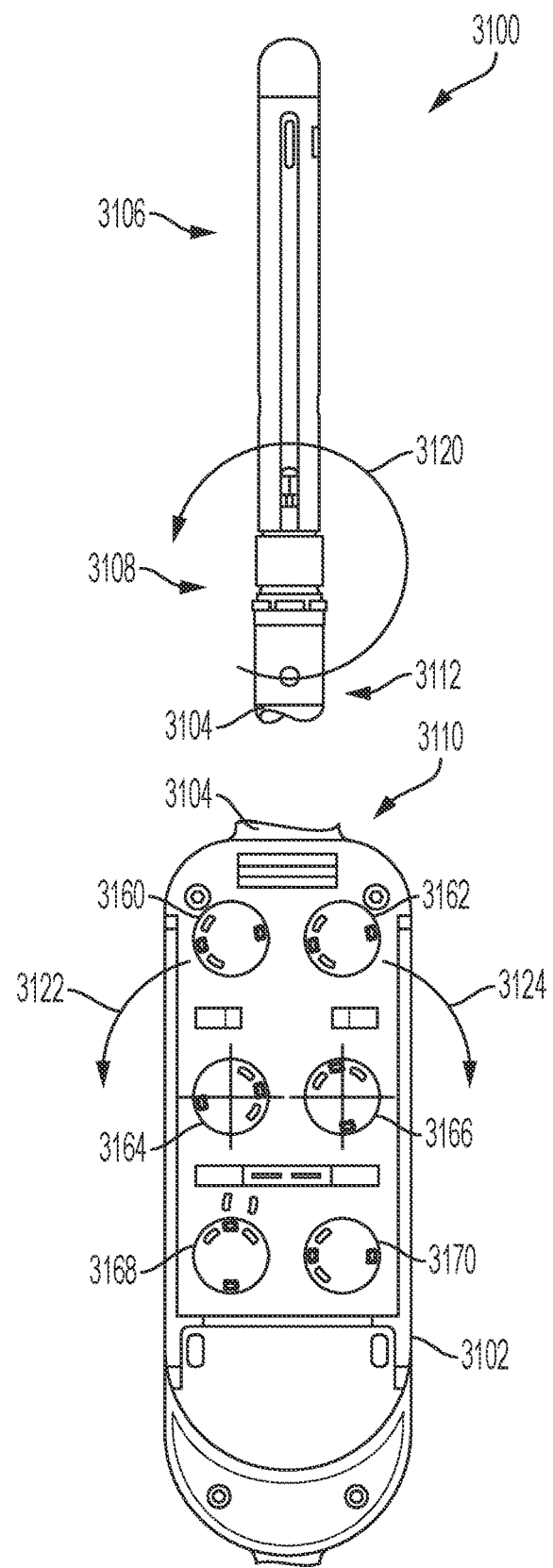
FIG. 21 is an elevation view of a robotic surgical tool including a drive housing, a surgical end effector, and an articulation joint between the drive housing and the surgical end effector, in accordance with at least one aspect of the present disclosure.

Referring to FIG. 21, a robotic surgical tool 3100 is shown. The robotic surgical tool 3100 can be controlled by the control circuit 3020 (FIG. 22) and can be used in conjunction with a robotic surgical system, such as the robotic surgical system 100 (FIG. 1) and with the robotic arm 200 (FIG. 2) and the tool drive 220 (FIGS. 2 and 3). The robotic surgical tool 3100 includes a tool base, or proximal housing, 3102 that is similar in many aspects to the tool base 352 (FIG. 5) and includes six rotary drives 3160, 3162, 3164, 3166, 3168, and 3170 similar to the rotary drives 360, 362, 364, 366, 368, and 370 of tool base 352 (FIG. 5), for example. As with the rotary drives of the tool base 352, the rotary drives of the tool base 3102 are configured to mate with six motor-driven rotary inputs or drivers on a tool carriage, such as the rotary drivers 260, 262, 264, 266, 268, and 270 on the tool carriage 224 (FIG. 4), for example. In various instances, each rotary drive 3160, 3162, 3164, 3166, 3168, and 3170 can be associated with a degree of freedom of the robotic surgical tool 3100.

A control circuit, for example the control circuit 3020 (FIG. 22), may be in communication with one or more torque sensors and/or one or more rotary encoders, such as torque sensors 3030, 3032 and position sensors 3034, 3036. The torque sensor(s) and/or rotary encoder(s) can be monitoring devices, which are configured to monitor operational parameters of the robotic surgical tool 3100. The torque sensors, for instance, may be configured to monitor torque, and the rotary encoders may be configured to monitor motion (rotational or linear). The torque sensors and the rotary encoders can be incorporated into the motors of some or all of the drivers 260, 262, 264, 266, 268, and 270 (FIG. 5). Additionally or alternatively, the torque sensors and/or the rotary encoders can be operatively coupled to one or more of the rotary input drives 3160, 3162, 3164, 3166, 3168, and 3170 on the tool base 3102. The torque sensors may be configured to measure the real-time torque loading on the motors, which corresponds to the torque loading by the drivers 260, 262, 264, 266, 268, and 270, and/or the drive inputs 3160, 3162, 3164, 3166, 3168, and 3170, in various instances. The rotary encoders may measure the rotational motion or output of the motors, which corresponds to the rotational motion of the drivers 260, 262, 264, 266, 268, and 270 and/or the drive inputs 3160, 3162, 3164, 3166, 3168, and 3170. Monitoring torque loading and rotational motion of the motors may help determine if the robotic surgical tool 3100 is operating in accordance with the commands provided by the control circuit.

Figure 22:
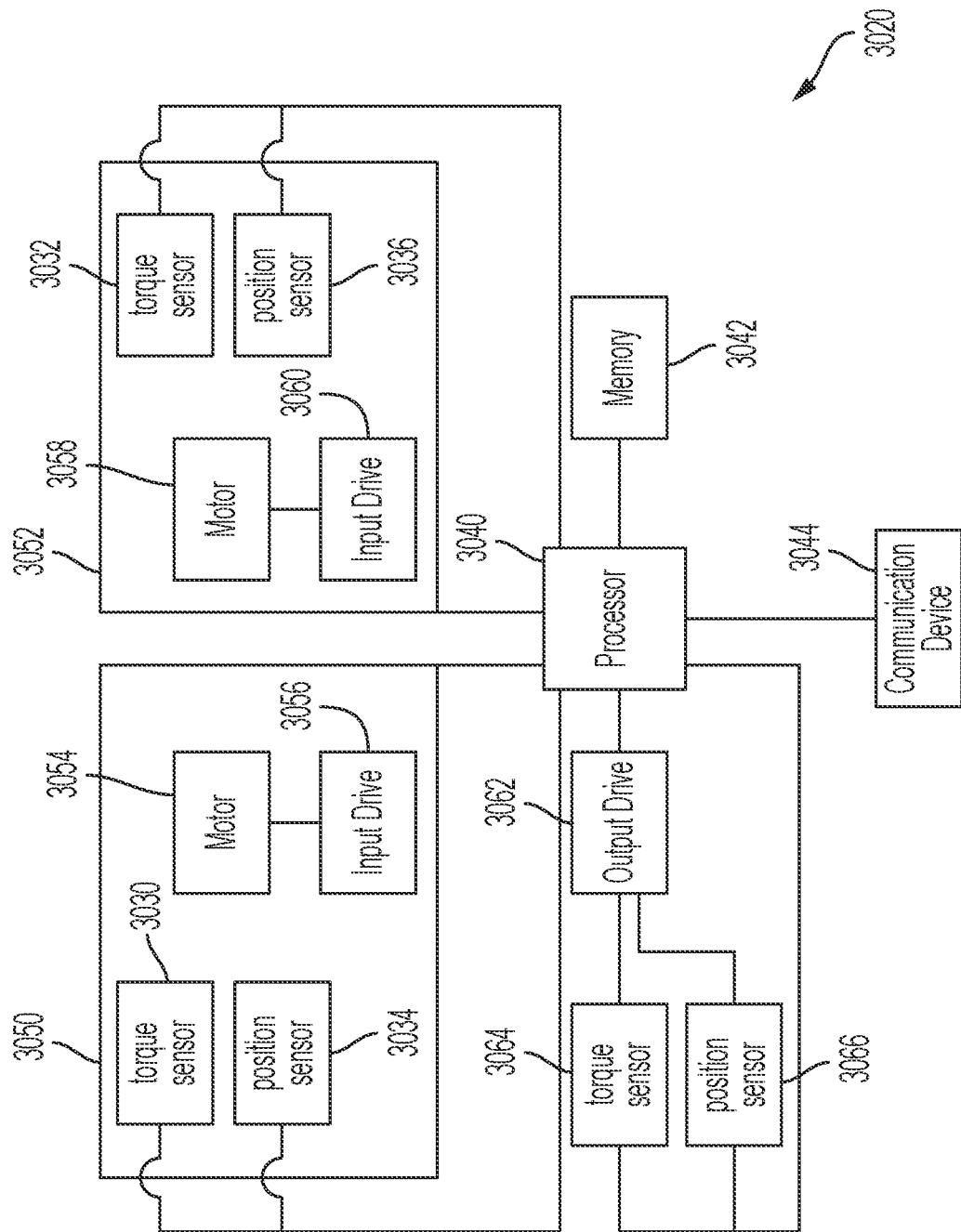
FIG. 22 is a schematic of a control circuit for use with two articulation input drives of FIG. 21, in accordance with at least one aspect of the present disclosure.

Referring to FIG. 22, a control circuit 3020 for controlling two motors that drive an articulation joint, such as the drivers 264 and 266 (FIG. 5), for example, is shown in FIG. 22. The control circuit 3020 includes a processor 3040 in signal communication with a memory 3042 and with a communication device 3044. A first drive system 3050 and a second drive system 3052 are in signal communication with the processor 3040. The first drive system 3050 includes a motor 3054, an input drive 3056 coupled to the motor 3054, a torque sensor 3030, and a rotary encoder/position sensor 3034. The input drive 3056 can correspond to the drive input 3164 and the motor 3054 can correspond to the driver 264, for example. In other aspects of the present disclosure, different drivers and drive inputs can correspond to the motor 3054 and input drive 3056.

The second drive system 3052 includes a motor 3058, an input drive 3060 coupled to the motor 3058, a torque sensor 3032, and a rotary encoder/position sensor 3036. The input drive 3060 can correspond to the drive input 3166 and the motor 3058 can correspond to the driver 266, for example. In other aspects, different drivers and drive inputs can correspond to the motor 3058 and input drive 3060. In such instances, the torque sensors 3030 and 3032 determine the torque on the motor 3054 and the motor 3058, respectively. The torque sensors 3030 and 3032 can determine the torque on the drivers 264 and 266, for example. Moreover, the position sensors 3034 and 3036 determine the angular position of the motor 3054 and the motor 3058, respectively. The position sensors 3034 and 3036 can determine the angular position on the drivers 264 and 266, for example.

The control circuit 3020 also includes an output drive 3062, a torque sensor 3064, and a rotary encoder/position sensor 3066. The output drive 3062 can correspond to an articulation joint 3108 (FIG. 21), for example. In such instances, the torque sensor 3064 determines the output torque applied to the articulation joint 3108, and the position sensor 3066 determines the angular position of the articulation joint 3108.

Referring primarily to FIG. 21, an elongate shaft 3104 extends distally from the tool base 3102; the elongate shaft 3104 includes a proximal end 3110 a distal end 3112. A distal end effector 3106 is coupled to the distal end 3112 of the elongate shaft 3104 at an articulation joint, or wrist joint, 3108. The articulation joint 3108 is similar to the articulation joint 458 (FIG. 6) in certain aspects of the present disclosure.

The articulation joint 3108 enables the end effector 3106 to articulate or pivot relative to the shaft 3104 and thereby position the end effector 3106 at desired orientations and locations relative to a surgical site. For example, rotation of the rotary drive 3164 and the rotary drive 3166 may cause the articulation joint 3108 to rotate. Specifically, rotation of the rotary drive 3164 in a direction 3122 and of the rotary drive 3166 in a direction 3124 may cause the articulation joint 3108 to rotate in a direction 3120. In other aspects of the present disclosure, different rotational directions and/or rotary drives can effect articulation of the articulation joint 3108.

Figure 23:
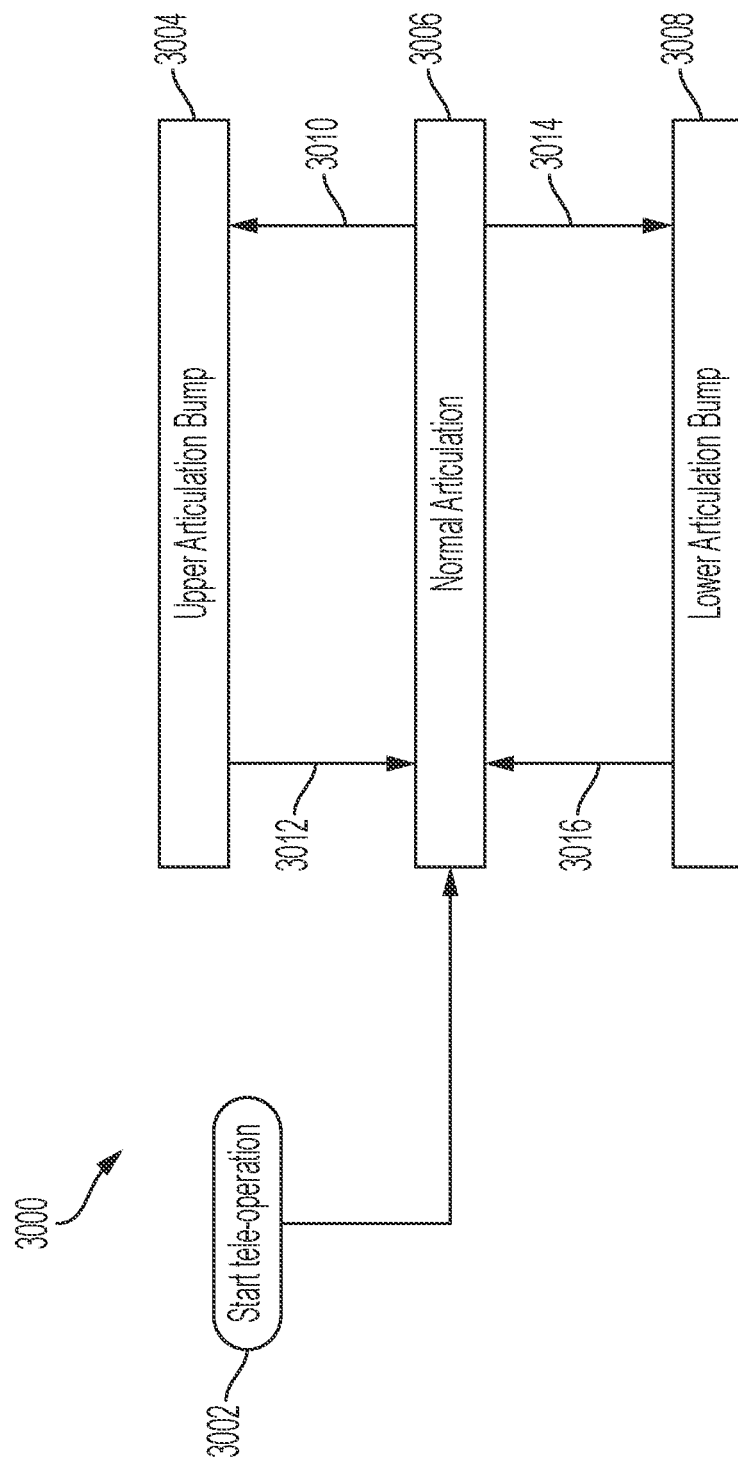
FIG. 23 is a control schematic for a soft bump articulation control process for a robotic surgical tool, in accordance with at least one aspect of the present disclosure.

Referring to FIG. 23, a soft bump articulation control process 3000 for a robotic surgical tool is shown. The soft bump articulation control process 3000 is configured to control the articulation motors coupled to the rotary drivers that drive the articulation system in the robotic surgical tool. For example, the soft bump articulation control process 3000 is configured to control the articulation of the articulation joint 3108 of the robotic surgical tool 3100 in various instances. The soft bump articulation control process 3000 is configured to allow the articulation mechanism to move through the full articulation range of motion. The full articulation range of motion reaches the mechanical joint limits with a soft bump at the mechanical joint limit, which is when the mechanical limit of the joint is reached. In such instances, the joint can slowly and softly hit the mechanical limit without damaging the robotic surgical tool 3100. This soft bump articulation control process 3000 allows the articulation joint 3108 to be driven to any location in its full articulation range of motion.

Prior to starting a teleoperation with a surgical robot and the robotic surgical tool 3100, the robotic surgical tool 3100 can be attached to the surgical robot and a homing operation for the robotic surgical tool can be performed. For example, when the robotic surgical tool is mounted to the tool driver, the robotic system can undergo a homing operation, in which positions of the various components are determined and recorded to ascertain various limits of the surgical system. For example, a start location of the rotary inputs attached to the rotary drivers of the robotic surgical tool may be determined by the homing process. The mechanical limits of a joint in a robotic surgical tool, such as the articulation joint 3108, for example, may also be determined during the homing process.

In other instances, a robotic surgical system may not perform a homing process and the mechanical limits and/or current joint locations may be stored in a memory and recalled from the memory upon attachment of the robotic surgical tool to the surgical robot.

If a mechanical limit is reached at a high speed and/or torque, the high impact load may damage the robotic surgical tool or its articulation drive system. A reduction in the range of articulation motion for the tool may be around 1%, 2%, 5%, 10%, or higher to ensure that measurement error of the joint's location does not result in contacting the mechanical limit of the joint at a high speed and/or torque.

FIG. 23 describes the soft bump articulation control process 3000 for two motors that drive an articulation joint and do not have a reduction from the maximum operating range. In certain instances, the soft bump articulation control process 3000 can be adapted to have only one motor and, in other instances, more than two motors driving an articulation motion.

Referring still to FIG. 23, at a step 3002 in the soft bump articulation control process 3000, the teleoperation begins and the control circuit 3020 starts a normal articulation control mode 3006 (or first operating state). During the normal articulation control mode 3006, the motors that control the articulation joint, such as the motors driving the rotary drivers 264, 266 (FIG. 4) which are mated to the rotary drives 3164, 3166, for example, are operated under normal or standard speeds and torques. Additionally, under the normal articulation control mode 3006, the motors that drive the articulation joint are driven at the desired input inverse kinematics and operated under normal speeds and torques. The two input motor angles can be monitored. Stated differently, parameters indicative of a rotary position of each articulation motors can be monitored during the first operating state. Additionally, a parameter indicative of the position of the articulation joint can be monitored during the first operating state.

If either motor angle exceeds a threshold rotation angle, then the control circuit 3020 transitions from the normal articulation control mode 3006 to an upper articulation bump control mode 3004 (or second operating state) or a lower articulation bump control mode 3008 (or third operating state), as further described herein. Stated differently, the control circuit 3020 operates the articulation motors in a first operating state, e.g. normal articulation control mode 3006, in a range of positions and transitions to a second operating state, e.g. the upper articulation bump control mode 3004 or the lower articulation bump control mode 3008, in a different range of positions.

The control circuit 3020 transitions from the normal articulation control mode 3006 to the upper articulation bump control mode 3004 following a path 3010 when the angle of a first articulation motor exceeds an upper articulation bump threshold angle. Stated differently, the control circuit 3020 operates a first articulation motor and a second articulation motor in a first operating state, e.g. normal articulation control mode 3006, when the rotary position of the first articulation motor is in a first range of positions. The control circuit 3020 operates the first and the second articulation motors in a second operating state, e.g. upper articulation bump control mode 3004, when the rotary position of the first articulation motor is in a second range of positions. In certain instances, the first range of positions and the second range of positions are non-overlapping. In certain instances, the first range of positions and the second range of positions are contiguous. The control circuit 3020 transitions the first and second articulation motors from the first operating state to the second operating state when the rotary position of the first articulation motor moves from the first range of positions to the second range of positions. In certain instances, the first and second articulation motors could be the motors driving the rotary drives 3164 and 3166 or vice versa.

In certain instances, an upper articulation bump threshold angle may be a motor rotation angle that corresponds to 1%, 2%, 5%, 10%, or any articulation angle within 15% of the upper mechanical limit of the articulation joint. Additionally, or alternatively, the upper articulation bump threshold could be any motor rotation angle that ensures that the upper mechanical limit is not reached in the normal articulation control mode 3006.

During the upper articulation bump control mode 3004, the two input motor angles and the articulation joint angle can be monitored. Stated differently, parameters indicative of the positions of the input motors and articulation joint can be monitored during the second operating state. If the articulation joint angle is increasing in the upper articulation bump control mode 3004 (i.e. moving toward the mechanical upper limit), then the articulation motors can be driven at the desired inverse kinematics and operated under limited speeds and/or limited torques. The motor torques and/or motor speeds can be limited to less than the standard torque and/or speed permitted during the normal articulation control mode 3006, which can allow the articulation joint 3108 to reach its mechanical upper limit without causing a high impact load on the articulation system or robotic surgical tool 3100. Stated differently, when the first articulation motor and the second articulation motors are in the second operating state and the rotary position of the first articulation motor is moving away from the first range of positions, then the maximum allowable speed and maximum allowable torque for the first and second articulation motors are lower than in first operating state.

In various instances, if the articulation joint angle is decreasing in the upper articulation bump control mode 3004 (i.e. moving away from the mechanical upper limit), then the two articulation motors are driven at the desired inverse kinematics and may be operated under normal speeds and torques. Stated differently, when the first and second articulation motors are in the second operating state and the rotary position of the first articulation motor is moving toward the first range of positions, then the maximum allowable speed and maximum allowable torque for the first and second articulation motors may be the same as in the first operating state, for example. Once the first articulation motor angle decreases past the upper articulation bump threshold angle and an additional anti-dither angle, the control circuit 3020 transitions from the upper articulation bump control mode 3004 back to the normal articulation control mode 3006 following a path 3012. Stated differently, the control circuit 3020 re-implements the first operating state from the second operating state for the first and second articulation motors when the rotary position of the first articulation motor returns to the first range of positions from the second range of positions by a threshold anti-dither angle. The additional anti-dither angle is a small angle that allows for a smooth transition between the upper articulation bump control mode 3004 and the normal articulation control mode 3006. In certain instances, the anti-dither angle is an angle that is less than ten degrees and may be one or two degrees, for example. In certain instances, the anti-dither angle is zero.

The control circuit 3020 transitions from the normal articulation control mode 3006 to the lower articulation bump control mode 3008 following a path 3014 when the angle of the second articulation motor exceeds a lower articulation bump threshold angle. Stated differently, the control circuit 3020 operates the first and second articulation motors in a first operating state, e.g. normal articulation control mode 3006, when the rotary position of the second articulation motor is in a third range of positions. The control circuit 3020 operates the first and second articulation motors in a third operating state, e.g. lower articulation bump control mode 3008, when the rotary position of the second articulation motor is in a fourth range of positions. In certain instances, the third range of positions and the fourth range of positions are non-overlapping. In certain instances, the third range of positions and the fourth range of positions are contiguous. The control circuit 3020 transitions the first and second articulation motors from the first operating state to the third operating state when the rotary position of the second articulation motor moves from the third range of positions to the fourth range of positions. In certain instances, the first and second articulation motors could be the motors driving the rotary drives 3164 and 3166 or vice versa.

In certain instances, the lower articulation bump threshold angle may be a motor rotation angle that corresponds to 1%, 2%, 5%, 10%, or any articulation angle within 15% of the lower mechanical limit of the articulation joint. Additionally, or alternatively, the lower articulation bump threshold could be any motor rotation angle that ensures that the lower mechanical limit in the normal articulation operating mode 3006.

During the lower articulation bump control mode 3008, the two input motor angles and articulation joint angle can be monitored. Stated differently, parameters indicative of the positions of the input motors and the articulation joint can be monitored during the third operating state. If the articulation joint angle is decreasing in the lower articulation bump control mode 3008 (i.e. moving toward the mechanical lower limit), then the articulation motors are driven at the desired inverse kinematics and operated under limited speeds and/or limited torques. The articulation input motor torques and speeds are limited to allow the articulation joint to reach the mechanical lower limit of the articulation joint without causing high impact loads. Stated differently, when the first and second articulation motors are in the third operating state and the rotary position of the second articulation motor is moving away from the third range of positions, then the maximum allowable speed and maximum allowable torque for the first and second articulation motors are lower than in first operating state.

In various instances, if the articulation joint angle is increasing in the lower articulation bump control mode 3008 (i.e. moving away from the mechanical lower limit), then the two articulation motors are driven at the desired inverse kinematics and operated under normal speeds and torques. Stated differently, when the first and second articulation motors are in the third operating state and the rotary position of the second articulation motor is moving toward the third range of positions, then the maximum allowable speed and maximum allowable torque for the first and second articulation motors may be the same as in the first operating state, for example. Once the second articulation motor angle increases past the lower articulation bump threshold angle and an additional anti-dither angle, the control circuit 3020 transitions from lower articulation bump control mode 3008 back to normal articulation control mode 3006 following path 3016. Stated differently, the control circuit 3020 re-implements the first operating state from the third operating state for the first and second articulation motors when the rotary position of the second articulation motor returns to the third range of positions from the fourth range of positions by a threshold anti-dither angle.

The additional anti-dither angle is a small angle that allows for a smooth transition between the lower articulation bump control mode 3008 and the normal articulation control mode 3006. In certain instances, the anti-dither angle is an angle that is less than ten degrees and may be one or two degrees, for example. In certain instances, the anti-dither angle can be zero.

The control circuit 3020 can be implemented as a non-transitory computer readable medium storing computer readable instructions. Accordingly, the non-transitory computer-readable medium includes any type of tangible machine-readable medium suitable for storing or transmitting electronic instructions or information in a form readable by a machine (e.g., a computer), which can implement the transitions between operating states and/or modes 3004, 3006, and/or 3008.

In various instances, the soft bump articulation control process 3000 can be used to control other joints on a robotic surgical tool in which the joint is configured to bumps a mechanical joint limit during its range of motion.

Figures 24, 25:
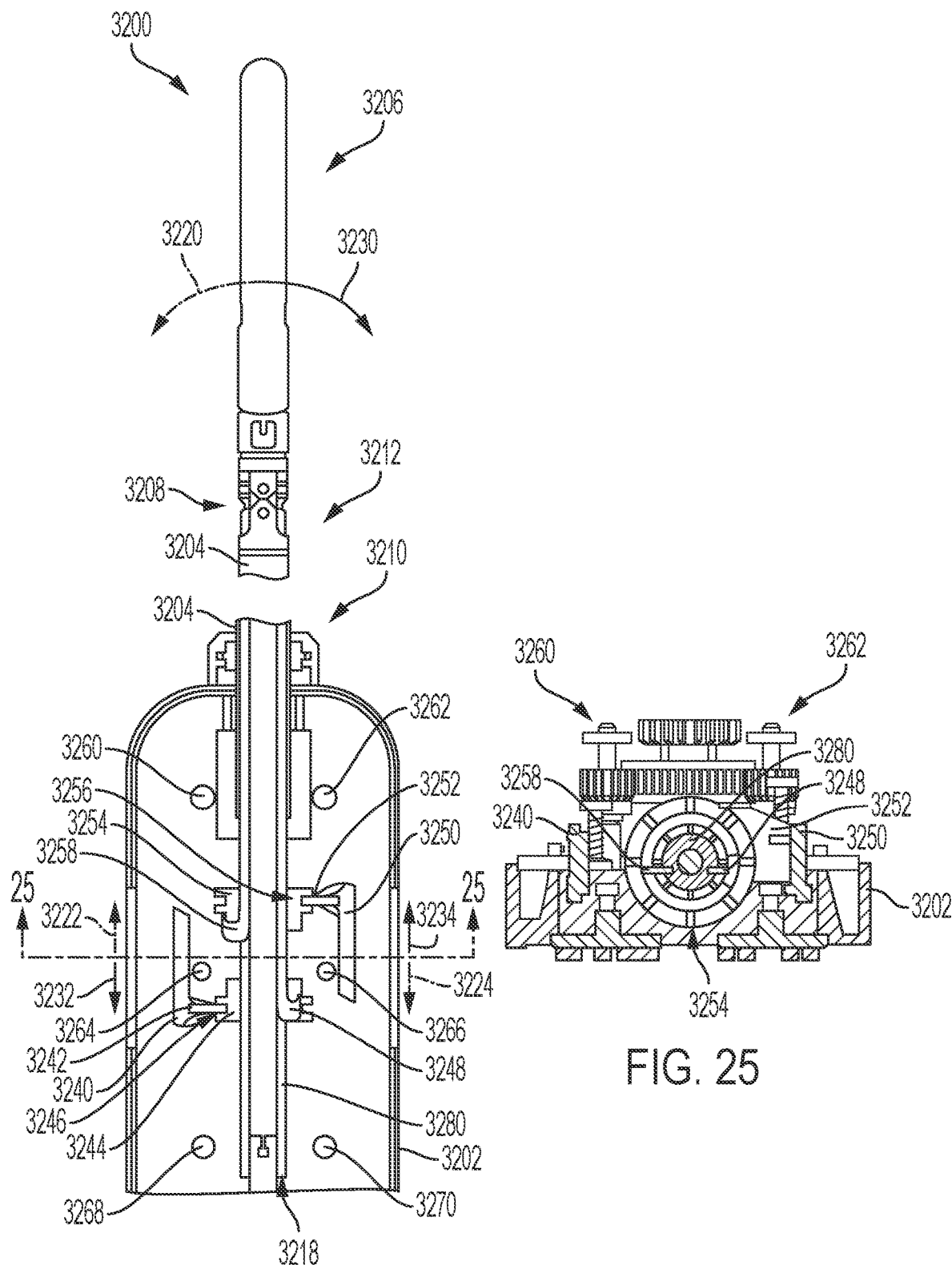
FIG. 24 is an elevation view of a portion of a robotic surgical tool including a drive housing, a surgical end effector, and an articulation joint between the drive housing and the surgical end effector, with certain features removed from the robotic surgical tool for clarity and to expose an interior of the drive housing, in accordance with at least one aspect of the present disclosure.
FIG. 25 is a cross-sectional view of the drive housing of FIG. 24 taken along the plane indicated in FIG. 24, in accordance with at least one aspect of the present disclosure.

Referring now to FIG. 24, a portion of a robotic surgical tool 3200 is shown. The robotic surgical tool 3200 is similar in many aspects to the robotic surgical tool 3100. The robotic surgical tool 3200 includes a tool base, or proximal housing, 3202, which is similar in many aspects to the tool base 3102 and includes six rotary drives 3260, 3262, 3264, 3266, 3268, and 3270. Certain portions of the proximal housing 3202 are removed from the robotic surgical tool 3200 in FIG. 24 to expose an interior portion of the proximal housing 3202 including the six rotary drives 3260, 3262, 3264, 3266, 3268, and 3270 and components of the articulation system housed therein.

An elongate shaft 3204 extends distally from the tool base 3202; the elongate shaft 3204 includes a proximal end 3210 and a distal end 3212. A distal end effector 3206 is coupled to the distal end 3212 of the elongate shaft 3204 at an articulation joint, or wrist joint, 3208. The articulation joint 3208 is similar to the articulation joint 3108 in many aspects of the present disclosure. The articulation joint 3208 enables the end effector 3206 to articulate or pivot relative to the elongate shaft 3204 and thereby position the end effector 3206 at desired orientations and locations relative to a surgical site.

Referring still to FIG. 24, the rotary drive 3264 drives a first drive rack 3240. Rotational movement of the rotary drive 3264 corresponds to linear movement of the first drive rack 3240 in either a direction 3222 or a direction 3232 depending on the rotational direction of the rotary drive 3264. The first drive rack 3240 includes a first fork 3242 matable with a first articulation yoke 3244. More specifically, the first fork 3242 is configured to be received within an annular slot 3246 defined in the first articulation yoke 3244. Engagement between the first fork 3242 and the annular slot 3246 allows the first drive rack 3240 to drive the first articulation yoke 3244 linearly along an internal shaft 3280 in either the direction 3222 or the direction 3232. The internal shaft 3280 extends from within the tool base 3202 at a location 3218 through the elongated shaft 3204 to the articulation joint 3208.

The first articulation yoke 3244 is coupled to a first articulation band 3248, which extends distally to the articulation joint 3208. As illustrated, the first articulation band 3248 is arranged within a corresponding slot defined in the internal shaft 3280, such that the internal shaft 3280 guides the first articulation band 3248 as it extends distally to the articulation joint 3208. Axial movement of the first articulation yoke 3244 along a longitudinal axis parallel to the internal shaft 3280 correspondingly moves the first articulation band 3248, which corresponds to articulation of the articulation joint 3208. In certain instances, movement of the first articulation yoke 3244 in the direction 3232 may cause the articulation joint 3208 to articulate and move the end effector 3206 in a direction 3230, for example. In certain instances, movement of the first articulation yoke 3244 in the direction 3222 may cause the articulation joint 3208 to articulate and move the end effector 3206 in a direction 3220, for example.

Referring still to FIG. 24, the rotary drive 3266 drives a second drive rack 3250. Rotational movement of the rotary drive 3266 corresponds to linear movement of the second drive rack 3250 in either a direction 3224 or a direction 3234 depending on the rotational direction of the rotary drive 3266. The second drive rack 3250 includes a second fork 3252 matable with a second articulation yoke 3254. More specifically, the second fork 3252 is configured to be received within an annular slot 3256 defined in the second articulation yoke 3254. Moreover, engagement between the second fork 3252 and the annular slot 3246 allows the second drive rack 3250 to drive the second articulation yoke 3254 linearly along the internal shaft 3280 in either the direction 3224 or the direction 3234.

The second articulation yoke 3254 may be coupled to a second articulation band 3258, which extends distally to the articulation joint 3208. As illustrated, the second articulation band 3258 is arranged within a corresponding slot defined in the internal shaft 3280, such that the internal shaft 3280 guides the second articulation band 3258 as it extends distally to the articulation joint 3208. Axial movement of the second articulation yoke 3254 along a longitudinal axis parallel to the internal shaft 3280 correspondingly moves the second articulation band 3258, which causes the articulation joint 3208 to articulate. In certain instances, movement of the second articulation yoke 3254 in the direction 3234 may cause the articulation joint 3208 to articulate and move the end effector 3206 in the direction 3230, for example. In certain instances, movement of the second articulation yoke 3254 in the direction 3224 may cause the articulation joint 3208 to articulate and move the end effector 3206 in the direction 3220, for example.

Axial movement of the first and second articulation yokes 3244, 3254 can cooperatively actuate the first and second articulation bands 3248, 3258 and, thereby, articulate the end effector 3206 as further described herein. Movement of the first articulation yoke 3244 in the direction 3232 and movement of the second articulation yoke 3254 in the direction 3234 corresponds to articulation of the end effector 3206 in the direction 3230. Said another way, movement of the first articulation yoke 3244 and the second articulation yoke 3254 away from each other corresponds to articulation of the end effector 3206 in the direction 3230. Additionally, movement of the first articulation yoke 3244 in the direction 3222 and movement of the second articulation yoke 3254 in the direction 3224 corresponds to articulation of the end effector 3206 in the direction 3220. Stated differently, movement of the first articulation yoke 3244 and the second articulation yoke 3254 toward each other corresponds to articulation of the end effector 3206 in the direction 3220. In at least one aspect of the present disclosure, the first and second articulation yokes 3244, 3254 protagonistically operate such that one of the articulation yokes 3244, 3254 pulls one of the articulation bands 3248, 3258 proximally while the other articulation yokes 3244, 3254 pushes the other articulation band 3248, 3258 distally.

In other aspects, the first and second articulation yokes 3244, 3254 may be operated independently without the other being operated (affected). In certain instances, the first and second articulation yokes 3244, 3254 may operate antagonistically where one reduces the force effect of another. In an antagonistic operation, one of the articulation yokes 3244, 3254 pulls (or pushes) the articulation bands 3248, 3258 associated therewith proximally (or distally) with a first force while the other one of the articulation yokes 3244, 3254 pulls (or pushes) the articulation bands 3248, 3258 associated therewith proximally (or distally) with a second force. When the first force is larger than the second force, the first force can overcome the second force, as well as the internal losses of the device (i.e., friction) and loads imparted on the end effector 3206 via the external environment, such that that the articulation yoke 3244, 3254 providing the first force moves proximally (or distally) while the articulation yoke 3244, 3254 providing the second force moves distally (or proximally).

Still referring primarily to FIG. 24, the internal shaft 3280 extends distally within the elongated shaft 3204 and is connected to the articulation joint 3208. The articulation bands 3248, 3258 extend distally towards the articulation joint 3208 within corresponding slots defined within the internal shaft 3280. The corresponding slots may be provided on opposite sides of the internal shaft 3280, or may be defined elsewhere about the internal shaft 3280 in other instances.

FIG. 25 is a cross-sectional view of the proximal housing 3202 taken across the plane indicated in FIG. 24. The articulation bands 3248, 3258 sit inside slots on either side of the internal shaft 3280. The internal shaft 3280 extends through the second articulation yoke 3254. The second articulation band 3258 attaches to the second articulation yoke 3254. The first articulation band 3248 extends along the slot in the internal shaft 3280 and through the second articulation yoke 3254. The second drive rack 3250 attaches to the second articulation yoke 3254 at the second fork 3252.

In various instances, the sliding of the articulation yokes 3244, 3254 along the internal shaft 3280 can generate friction and corresponding internal losses. To effect the articulation motion, the articulation yokes 3244, 3254 must overcome the frictional losses and move along the internal shaft 3280. Articulation systems including articulation yokes configured to slide along an internal support chassis, like those shown in FIGS. 24 and 25 are further described in U.S. patent application Ser. No. 16/553,725, titled ARTICULATING INCLUDING ANTAGONISTIC CONTROLS FOR ARTICULATION AND CALIBRATION, filed Aug. 28, 2019, which is incorporated by reference herein in its entirety.

Internal moving parts that translate along each other to articulate an end effector generate friction. For example, the articulation yokes 3244, 3254 that move along the internal shaft 3280 of the robotic surgical tool 3200 shown in FIG. 24 generate friction during an articulation motion. In certain instances, the articulation of the end effector can cause significant frictional forces between the internal translating parts during normal loading conditions. Such frictional forces require the drive mechanism to supply more input torque to overcome the friction. In various instances, the high friction can cause a brake-like effect, which requires additional input torque for various subsystems that interact with the translating parts in order to overcome the friction. In various instances, it can be advantages to reduce the friction on the moving parts of a robotic surgical tool during an articulation motion.

An articulation drive system that mechanically reduces the friction between certain translating parts may be advantageous in certain instances. Such an articulation drive system can be sufficiently robust to articulate the end effector without requiring additional torque input due to frictional losses along the translating surfaces. For example, the incorporation of rolling elements (e.g. roto-linear ball bearings) between certain translating parts can reduce the frictional forces and losses therebetween.

In one aspect the present disclosure, a robotic surgical tool can comprise a housing, an end effector, and an elongate shaft extending distally from the housing to the end effector. The robotic surgical tool can further comprise an articulation joint configured to articulate the end effector relative to the elongate shaft during an articulation motion, an internal shaft extending distally from the housing through the elongate shaft, and an articulation drive system. The articulation drive system can comprise an articulation yoke coupled to the internal shaft, an articulation band coupled to the articulation yoke and extending distally along the internal shaft to the articulation joint, and rolling elements intermediate the internal shaft and the articulation yoke. The articulation yoke can be configured to roll along the rolling elements during the articulation motion.

In certain instances, the foregoing arrangement can reduce frictional losses between certain translating parts of the articulation drive system. Moreover, the reduced friction can improve load handling and requires less input torque. There may also be less induced friction on adjacent subsystems in certain instances.

Referring to FIGS. 26 and 27, portions of a robotic surgical tool 3300 are shown. The robotic surgical tool 3300 is similar in many aspects to the robotic surgical tool 3200. For example, the robotic surgical tool 3300 includes an internal shaft 3380, an articulation joint 3308, a surgical end effector 3306, and an articulation system including articulation yokes 3344, 3354. The articulation yokes 3344, 3354 are similar in many aspects to the articulation yokes 3244, 3254 (FIG. 24). Unlike the robotic surgical tool 3200, the robotic surgical tool 3300 also includes rolling element pads 3382 around the internal shaft 3380 between the articulation yokes 3344, 3354 and the internal shaft 3380. The rolling element pads 3382 include roto-linear elements (e.g. balls within a continuous looped track), which can reduce the friction caused from movement of the articulation yokes 3344, 3354 along the internal shaft 3380.

The internal shaft 3380 extends distally and is coupled to an articulation joint, or wrist joint, 3308 at the distal end of the internal shaft 3380. In various instances, a tool shaft can surround the internal shaft 3380 and also surround the components of the articulation system extending between the proximal housing to the end effector 3306. The internal shaft 3380 can be a chassis or support for the tool shaft and other components extending between the proximal housing and the end effector. For example, the internal shaft 3380 can support a firing member.

The articulation joint 3308 is similar in many aspects to the articulation joint 3208. The articulation joint 3308 enables the end effector 3306 to articulate or pivot relative to the internal shaft 3380 and thereby position the end effector 3306 at desired orientations and locations relative to a surgical site.

Referring still to FIGS. 26 and 27, a first drive rack 3340 attaches to the first articulation yoke 3344 with a first fork 3242 matable to the first articulation yoke 3344. More specifically, the first fork 3342 is configured to be received within an annular slot 3346 defined in the first articulation yoke 3344. Moreover, engagement between the first fork 3342 and the annular slot 3346 allows the first drive rack 3340 to drive the first articulation yoke 3344 linearly along the internal shaft 3380 in a direction 3322 or a direction 3332. Movement of the first articulation yoke 3344 in the direction 3322 or the direction 3332 along the internal shaft 3380 corresponds to articulation of the end effector 3306 in the direction 3320 or the direction 3330. The articulation yoke stop 3374 prevents the first articulation yoke 3344 from moving too far proximally, i.e. too far in the direction 3332, on the internal shaft 3380.

A second drive rack 3350 attaches to the second articulation yoke 3354 with a second fork 3352 matable to the second articulation yoke 3354. More specifically, the second fork 3352 is configured to be received within an annular slot 3356 defined in the second articulation yoke 3354. Moreover, engagement between the second fork 3352 and the annular slot 3356 allows the second drive rack 3350 to drive the second articulation yoke 3354 linearly along the internal shaft 3380 in a direction 3324 or a direction 3334. Movement of the second articulation yoke 3354 in the direction 3324 or the direction 3334 along the internal shaft 3380 corresponds to articulation of the end effector 3306 in the direction 3320 or the direction 3330.

Accordingly, axial movement of the first and second articulation yokes 3344, 3354, cooperatively actuate the first and second articulation bands 3348, 3358 and, thereby, articulate the end effector 3306, as further described herein. Movement of the first articulation yoke 3344 in the direction 3332 and movement of the second articulation yoke 3354 in the direction 3334 corresponds to articulation of the end effector 3306 in the direction 3330. Said another way, movement of the first articulation yoke 3344 and the second articulation yoke 3354 away from each other corresponds to articulation of the end effector 3306 in the direction 3330. Additionally, movement of the first articulation yoke 3244 in the direction 3222 and movement of the second articulation yoke 3254 in the direction 3224 corresponds to articulation of the end effector 3206 in the direction 3220. Said another way, movement of the first articulation yoke 3244 and the second articulation yoke 3254 toward each other corresponds to articulation of the end effector 3206 in the direction 3220.

The articulation yokes 3344, 3354 are configured to slide along multiple rolling element pads 3382 that are set into the internal shaft 3380. In certain instances, the rolling element pads 3382 may be press-fit into recesses or cavities in the internal shaft 3380. In various instances, there may be two, four, or eight rolling element pads 3382 set around the circumference of the internal shaft 3380. The internal shaft 3380 includes four rolling element pads 3382 around the circumference thereof. The reader will appreciate that there may be other suitable numbers of rolling element pads 3382 around the circumference of the internal shaft 3380, and the rolling element pads 3382 can be positioned to cover the region along which the articulation yokes 3344,3354 move along the internal shaft 3380.

Figure 28:
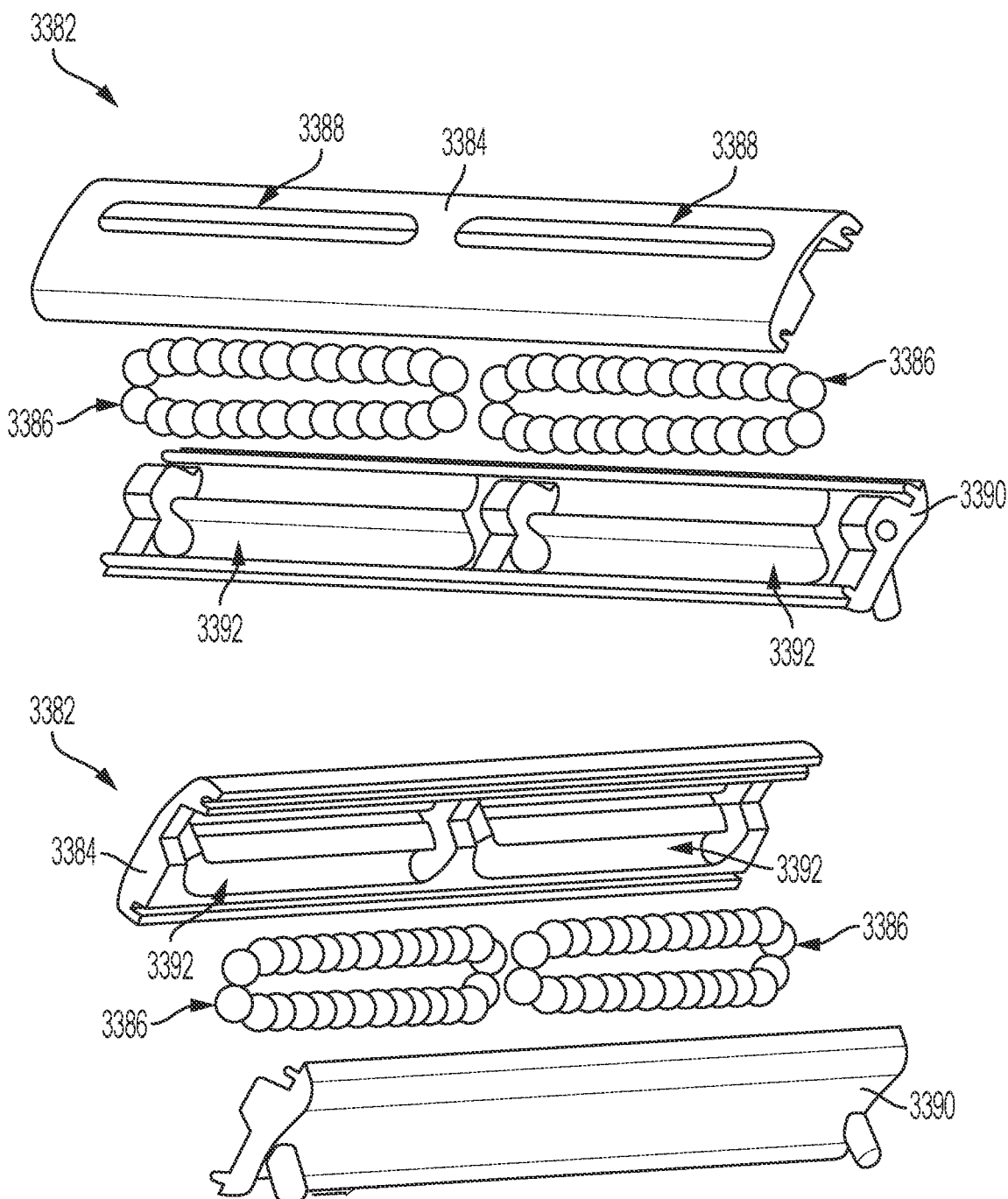
FIG. 28 is an exploded, perspective view of rolling element pads for an articulation system of a robotic surgical tool, in accordance with at least one aspect of the present disclosure.

Referring now to FIG. 28, an exploded view of a rolling element pad 3382 is shown. Each rolling element pad 3382 includes a rolling element retainer 3384, rolling elements, or balls, 3386, and a rolling element base 3390. The rolling elements 3386 in each rolling element pad 3382 are divided into two sets of rolling elements 3386 that sit in separate and independent continuous loop tracks 3392. The continuous loop tracks 3392 are defined between the rolling element retainer 3384 and the rolling element base 3390. The rolling elements 3386 can roll around their continuous loop track 3392, which allows the rolling elements 3386 to move and roll as the articulation yokes 3344, 3354 move relative to the internal shaft 3380. In such instances, the rolling element pads 3382 comprise roto-linear bearings for the articulation yokes 3344, 3354. The slits or windows 3388 in the rolling element retainer 3384 allow the rolling elements 3386 to interact with objects outside of the rolling element retainer 3384, such as the articulation yokes 3344, 3354, for example. The rolling elements 3386 stick out past the slits 3388 so that the articulation yokes 3344, 3354 are supported by and sit on the rolling elements 3386 and do not slide directly on the rolling element retainer 3384.

Referring primarily to FIG. 28, the rolling elements 3386 of each rolling element pad 3382 are held in the continuous loop track 3392 (FIG. 28) by the rolling element retainer 3384. The articulation yokes 3344, 3354 (FIGS. 26 and 27) slide on the rolling elements 3386 during the linear movement of the articulation yokes 3344, 3354 along the internal shaft 3380. The articulation yokes 3344, 3354 do not slide directly on the rolling element retainer 3384, but slide on the rolling elements 3386 that radially protrude beyond the retainer 3384. The rolling elements 3386 roll along the continuous loop track 3392 during the movement of the articulation yokes 3344, 3354.

In FIG. 28, there are two continuous loop tracks 3392 per rolling element pad 3382 and each articulation yoke 3344, 3354 sits on rolling elements 3386 of a different continuous loop track 3392. In such instances, the rolling elements 3386 associated with each articulation yoke 3344, 3354 (FIGS. 26 and 27) can travel in the same direction as the corresponding articulation yoke 3344, 3354. As described herein, the articulation yokes 3344, 3354 can move axially relative to each other (toward each other/together and away from each other/apart) and, thus, the rolling elements 3386 in the continuous loop tracks 3392 of the same rolling element pad 3382 can simultaneously or concurrently roll in different directions.

The rolling of the rolling elements 3386 is configured to reduce the friction caused by the movement of the articulation yokes 3344, 3354. Such a reduction in friction can allow for better handling of the articulation joint 3308 and require less input torque to articulate the end effector 3306 relative to the elongate shaft of the robotic surgical tool 3300. Moreover, there can be less induced friction on adjacent subsystems, such as the closure and shaft rolling subsystems of the robotic surgical tool, for example.

In various instances, it may be difficult for a clinician to visualize the orientation of a robotic surgical tool during a surgical procedure. For example, it may be difficult to visualize the orientation of the tool with respect to a constrained anatomy in which only an end effector, or portion thereof, is visible in the camera view.

In certain instances, an augmented rendering of the robotic surgical tool can be shown to the user to demonstrate the tool's orientation. The augmented rendering may show joints of the robotic surgical tool that are out of view/off camera. It is desirable to convey such information to the clinician without being overly distracting to the clinician. For example, the orientation may be depicted on the display at a transitional state between completion of a homing operation and the beginning of the teleoperation. The augmented rending of the robotic surgical tool can then be minimized or otherwise moved to a remote and/or unobtrusive location on the display screen so as to not distract the clinician.

In certain instances, an end effector overlay feature for a surgical imaging system can inform the clinician of the function and orientation of the robotic surgical tool without distracting the clinician from the surgical operation. The position of the robotic surgical tool in relation to the camera is already calculated by the robotic surgical system for tool mapping purposes in various instances.

Surgical camera views of a robotic surgical tool 3530 during a surgical procedure are shown in a series of views in FIGS. 30A-D, in which the orientation of the robotic surgical tool 3530 is conveyed to a clinician in the camera view 3500 with an end effector overlay feature. In various instances, such a feature can take advantage of the state between completion of the homing operation and the beginning of teleoperation of the robotic surgical tool 3530 to overlay, demonstrate, and minimize the augmented rendering of the distal end effector for the clinician's benefit and convenience.

Figure 30A:
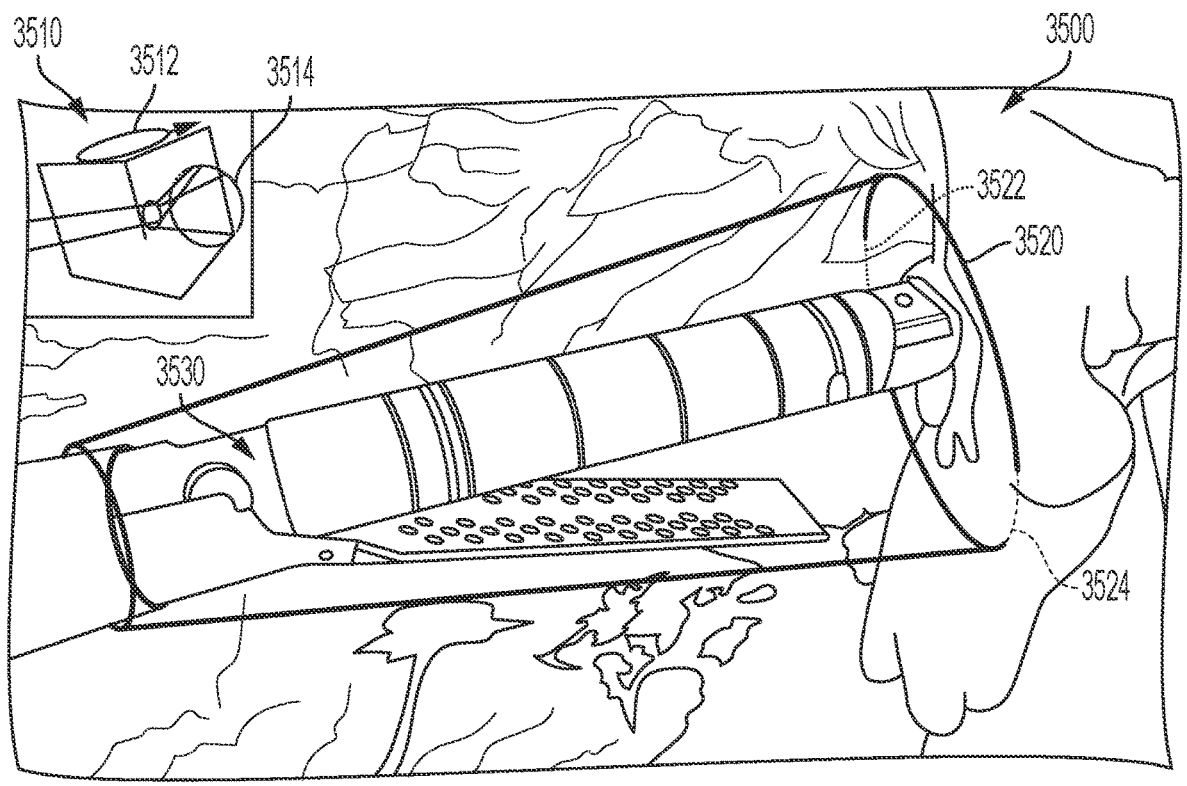

In various instances, the control system, such as the control tower 130 (FIG. 1) for example, can complete a homing operation and then wait for a clinician to manually extend the robotic surgical tool 3530 into the surgical field. The control system can track the orientation and position of the robotic surgical tool 3530 relative to the camera and monitor the camera view 3500. The control system can wait for a minimum amount of the end effector of the robotic surgical tool 3530 to appear within view, as shown in FIG. 30A, in various instances. The control system can then overlay an augmented rendering 3520 of the end effector on top of the actual end effector image on the display screen. Though the augmented rendering 3520 may be over the end effector on the display screen, the augmented rendering can be transparent and/or a skeleton/phantom depiction such that the end effector can also be seen by the clinician.

Figure 29:
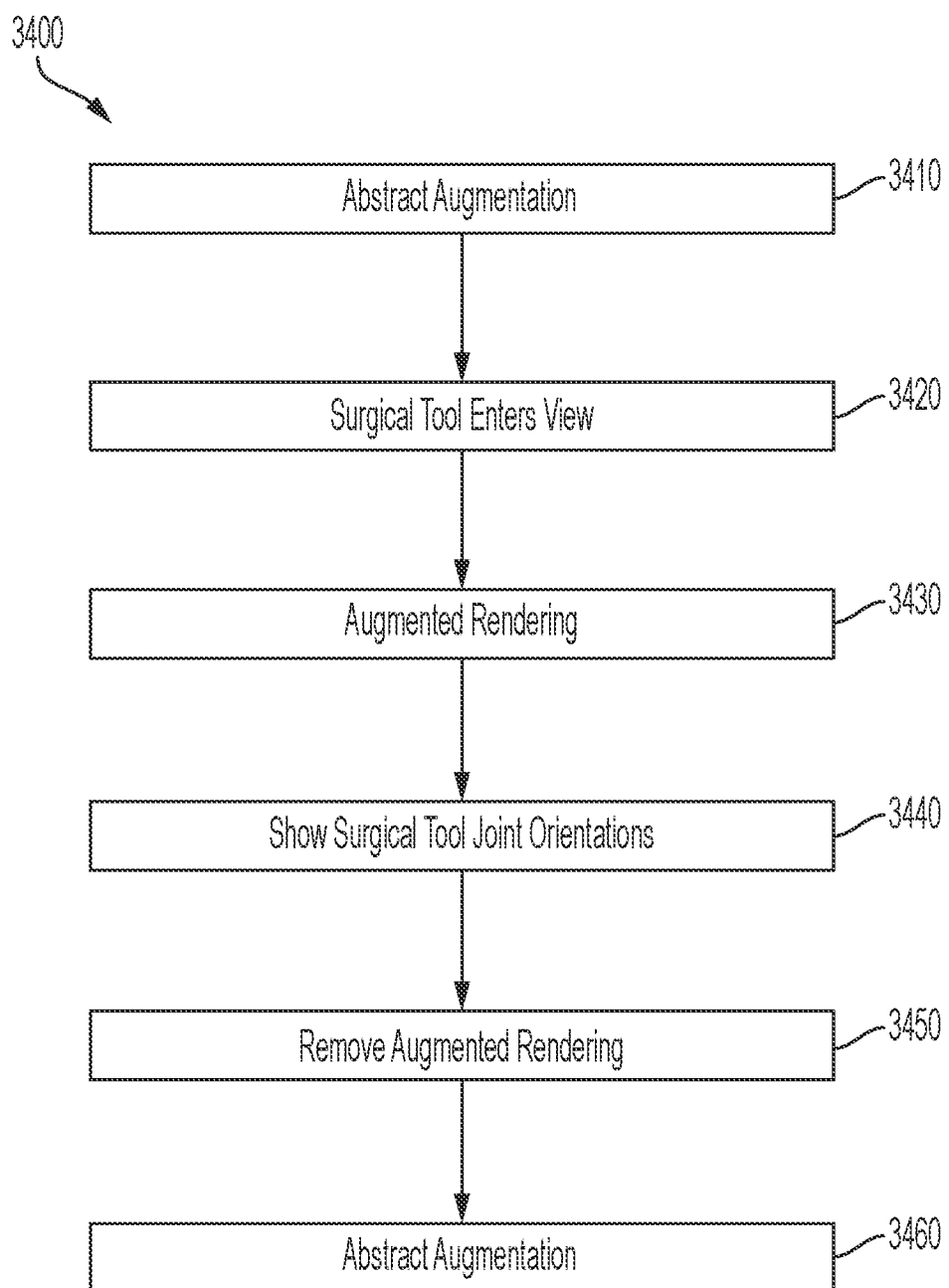
FIG. 29 is a flowchart describing the method of displaying an overlay feature on a visual display for a surgical imaging system, in accordance with at least one aspect of the present disclosure.

FIG. 29 is a flowchart 3400 showing the process of displaying the augmented rendering 3520 on the camera view 3500. In step 3410, the camera view has the abstract augmentation 3510 of the surgical tool 3530 in an unobtrusive location of the camera view 3500 and the surgical tool 3530 is not yet in the camera view 3500. At step 3420, the surgical tool 3530 enters the camera view 3500. Step 3430 commences when enough of the surgical tool enters the camera view 3500. At step 3430, an augmented rendering 3520 is overlaid on the camera view 3500. Next, at step 3440, the surgical tool 3530 joint orientations are shown to the clinician. At step 3450, the augmented rendering 3520 is removed by panning and scaling the augmented rendering 3520 toward the abstract augmentation 3510. At step 3460, the augmented rendering 3430 has reached the abstract augmentation 3510 and disappeared from the primary and/or central portion of the display screen.

The augmented rendering 3520 is a conical schematic reflecting the conical orientation of the jaws of the robotic surgical tool 3530. In other instances, the augmented rendering can be a different three-dimensional shape, such as a sphere or a prism. The shape of the augmented rendering 3520 can correspond to a general shape of the robotic surgical tool 3530 in various instances. The reader will appreciate that alternative robotic surgical tools, e.g. electrosurgery devices, scalpels, clip appliers, clamps, and/or ultrasonic tools, can employ the end effector overlay feature described herein.

In various instances, the augmented rendering 3520 can show the surgical tool 3530 joint orientations (Step 3440 of FIG. 29). In one example the joint orientations are shown by leaving the augmented rendering 3520 over the surgical tool 3530 for a period of time. Once the period of time has expired, the augmented rendering 3520 can be reduced in scale and moved off the actual robotic surgical tool 3530 to a less clinically-obtrusive location. For example, the augmented rendering 3520 can be moved to a side bar or a corner of the camera view 3500. When the robotic surgical tool 3530 moves during teleoperation, the augmented rendering 3520 can then moves accordingly, which can aid in visualization of the robotic surgical tool.

The augmented rendering 3520 can show the orientation and functionality of the robotic surgical tool 3530 by rotating the joints of the robotic surgical tool 3530 on the augmented rendering 3520. For example, the augmented rendering 3520 includes marks 3522, 3524 at the distal end thereof. The marks 3522, 3524 can be configured to rotate about the longitudinal axis, i.e. a roll axis, to shown the roll functionality of the robotic surgical tool 3530. In certain instances, the marks 3522, 3524 can be conveyed to a clinician as a variation in the line type of the augmented rendering 3520, as shown in FIG. 30A, and/or as a different color, for example. The marks 3522, 3524 can also be implemented by other signals, which allow the function (e.g. rotation about the longitudinal axis) to be conveyed to the clinician in a simplified and easy-to-identify manner. The marks 3522, 3524 can also be conveyed with a break in the line depicting the augmented rendering 3520.

An abstract augmentation 3510 of the robotic surgical tool 3530 is shown in an unobtrusive location of the camera view 3500. In FIGS. 30A-D, the unobtrusive location is the top left corner of the camera view 3500. Alternative locations are also possible, such as on a side bar or at any of the corners of the camera view 3500, for example. The abstract augmentation 3510 shows a rendering of the robotic surgical tool 3530 that shows the orientation of the entire robotic surgical tool 3530 including joints that are not in the camera view 3500. These orientations may be challenging for a clinician to appreciate in a typical view, in which most of the elongated shaft of the robotic surgical tool 3530 are not shown in the camera view. For example, the articulation joint place markers 3512 and roll place markers 3514 are shown in the abstract augmentation 3510 of FIGS. 30A-30D. The rendering on the abstract augmentation 3510 can move as the robotic surgical tool 3530 moves, which provides the clinician with feedback and information about the overall orientation of the joints of the robotic surgical tool 3530.

Figure 30B:
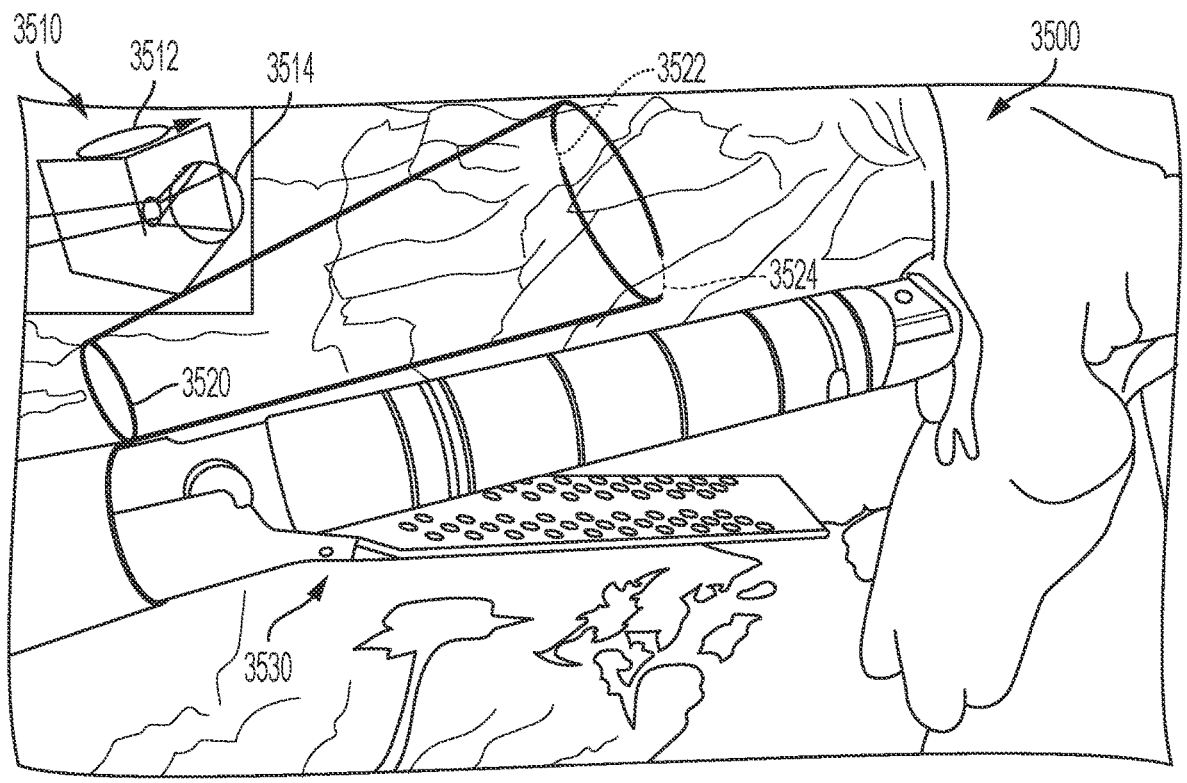
Figure 30C:
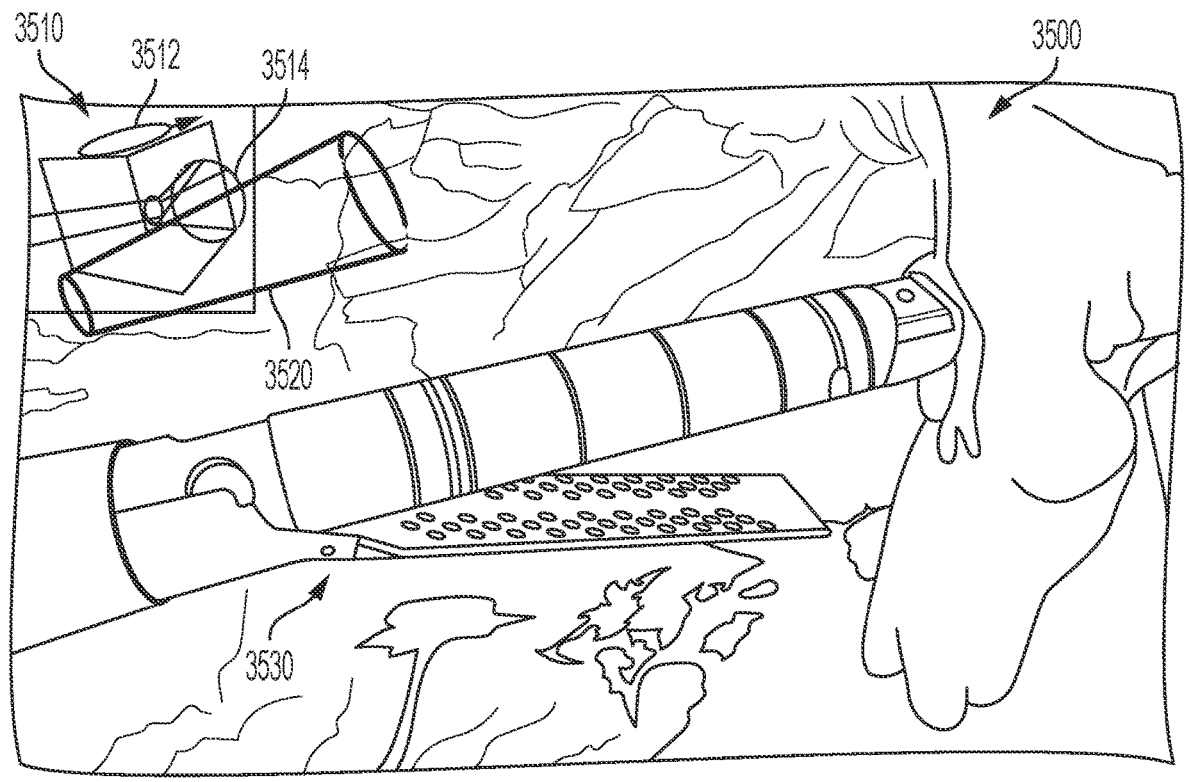
Figure 30D:
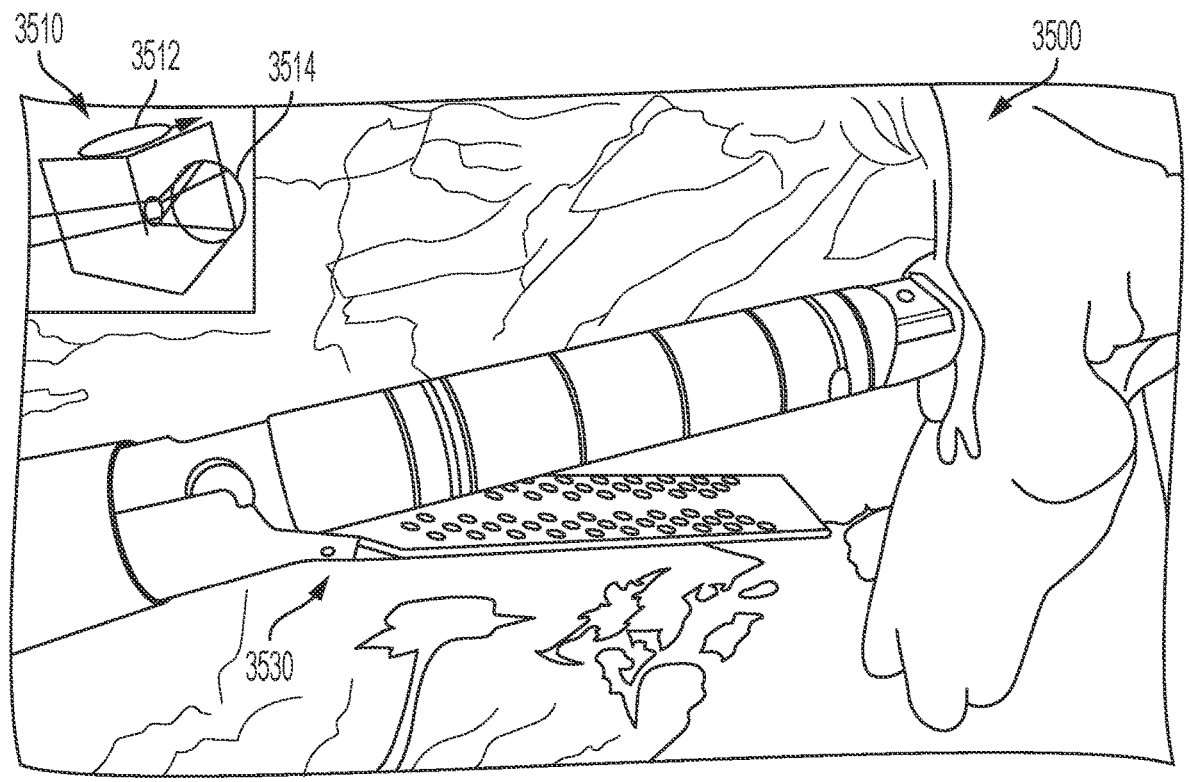

FIGS. 30A-30D show four stages of animation of the augmented rendering 3520 going from full overlay in FIG. 30A to the abstract augmentation 3510 in FIG. 30D. FIG. 30A shows the augmented rendering 3520 in a fully overlaid state. FIGS. 30B and 30C are transitional frames of the augmented rendering 3520 panning and scaling toward the abstract augmentation 3510. FIG. 30D shows a post-overlay scene with just the abstract augmentation 3510 in the top-left corner. The transition between the full overlay stage (FIG. 30A) and pure abstract augmentation 3510 stage (FIG. 30D) can be smooth in implementation. The augmented rendering 3520 pans and scales to become part of the abstract augmentation 3510.

In various instances, the rotation about a longitudinal axis is shown by roll place markers 3514 and the rotation about the articulation joint is shown by articulation place markers 3512, for example. The roll place markers 3514 and/or the articulation place markers 3512 can include marks, which can correspond to the marks on the augmented rendering 3520. For example, the marks can include the same signal and/or color to convey the correspondence to the clinician.

The augmented rendering 3520 can be configured to show the orientation of the surgical tool 3530 (Step 3440 of FIG. 29) by remaining on the robotic surgical tool 3530 for a period of time. Once the period of time is over, the augmented rendering 3520 can move off the robotic surgical tool 3530 to the abstract augmentation 3510, in certain aspects of the present disclosure. For example, the augmented rendering 3520 can pan and scale to the abstract augmentation 3510 located in the unobtrusive location.

In certain instances, the augmented rendering 3520 can show the orientation of the surgical tool 3530 (Step 3440 of FIG. 29) by remaining overlaid on the robotic surgical tool 3530 until the robotic surgical tool 3530 enters a teleoperation mode and a minimum amount of roll and/or articulation is implemented. In such instances, the augmented rendering 3520 moves with the robotic surgical tool 3530, which allows the clinician to observe the motion of the augmented rendering 3520. Once a minimum amount of travel or movement has been observed, the augmented rendering 3520 can pan and scale to the abstract augmentation 3510 located in the unobtrusive location.

In still other instances, the augmented rendering 3520 can be configured to show the orientation of the surgical tool 3530 (Step 3440 of FIG. 29) by having the augmented rendering 3520 automatically oscillate the joints of the robotic surgical tool 3530. This process could be used to catch the clinician's attention. For example, the roll joint and/or the articulation joints can initially be slightly oscillated to alert the clinician to their locations. After such an oscillation, the augmented rendering 3520 can return to matching the orientation of the robotic surgical tool, and then pan and scale to the abstract augmentation 3510 located in the unobtrusive location.

It is noted that there could be other methods to perform step 3440 of FIG. 29 with the augmented rendering 3520 and abstract augmentation 3510. Any method that uses the augmented rendering 3520 and abstract augmentation 3510 to show the surgical tool 3530 joint orientations could be used.

A robotic surgical system 2100 is shown in FIG. 31. Various aspects of the robotic surgical system 2100 are further described in U.S. Pat. No. 10,470,830, titled SYSTEM AND METHODS FOR INSTRUMENT BASED INSERTION ARCHITECTURES, issued Nov. 12, 2019, for example. U.S. Pat. No. 10,470,830, titled SYSTEM AND METHODS FOR INSTRUMENT BASED INSERTION ARCHITECTURES, issued Nov. 12, 2019, is incorporated by reference herein in its entirety.

The robotic surgical system 2100 includes a base 2101 coupled to one or more robotic arms, e.g., the robotic arms 2102 in FIG. 31. The base 2101 is communicatively coupled to a command console or user console, which is further described in U.S. Pat. No. 10,470,830, titled SYSTEM AND METHODS FOR INSTRUMENT BASED INSERTION ARCHITECTURES, issued Nov. 12, 2019, for example. In various instances, the command console for the robotic surgical system 2100 is similar in many aspects to the user console 110 (FIG. 1). The base 2101 can be positioned such that the robotic arm 2102 has access to perform a surgical procedure on a patient, while a user, such as a clinician or surgeon, for example, can control the robotic surgical system 2100 from the comfort of the command console. In some instances, the base 2101 can be coupled to a surgical operating table or a bed for supporting the patient. In other instances, the robotic arms can be supported by a freestanding robot having a base and/or column, for example, as further described in U.S. patent application Ser. No. 16/553,725, titled ARTICULATING INCLUDING ANTAGONISTIC CONTROLS FOR ARTICULATION AND CALIBRATION, filed Aug. 28, 2019, for example.

In some instances, the base 2101 may include subsystems such as control electronics, pneumatics, power sources, optical sources, and the like. The robotic arm 2102 includes multiple arm segments 2110 coupled at joints 2111, which provides multiple degrees of freedom, e.g., seven degrees of freedom corresponding to seven arm segments, for the robotic arm 2102. The base 2101 may contain a source of power 2112, pneumatic pressure 2113, and control and sensor electronics 2114—including components such as a central processing unit, data bus, control circuitry, and memory—and related actuators such as motors to move the robotic arm 2102. The electronics 2114 in the base 2101 may also process and transmit control signals communicated from the command console. The base 2101 also includes wheels 2115 to transport the robotic surgical system 100.

In some aspects of the present disclosure, the robotic arm 2102 includes set up joints that use a combination of brakes and counter-balances to maintain a position of the robotic arm 2102. The counter-balances may include gas springs or coil springs. The brakes, which are fail-safe brakes in certain instances, may include mechanical and/or electrical components. Further, the robotic arms 2102 can be gravity-assisted passive support type robotic arms.

Each robotic arm 2102 may be coupled to a tool driver 2117, which is also referred to herein as an instrument device manipulator (IDM), using a changer interface 2116. The tool driver 2117 can serve as a tool holder. In some instances, the tool driver 2117 can be removable, such that the tool driver 2117 can be replaced with a different type of tool driver. For example, the tool drivers 220 (FIG. 2-4) for the robotic surgical system 100 (FIG. 1) can be interchangeable with the tool driver 2117 (FIG. 31) in certain instances. For example, a first type of tool driver that manipulates an endoscope can be replaced with a second type of tool driver that manipulates a laparoscope. The changer interface 2116 includes connectors to transfer pneumatic pressure, electrical power, electrical signals, and optical signals from the robotic arm 2102 to the tool driver 2117. The changer interface 2116 can be a set screw or base plate connector. The tool driver 2117 manipulates surgical tools, such as the surgical tool 2118, for example, using techniques including direct drive, harmonic drive, geared drives, belts and pulleys, magnetic drives, and the like. The changer interface 2116 is interchangeable based on the type of tool driver 2117 and can be customized for a certain type of surgical procedure. The robotic arm 2102 can include joint level torque sensing and a wrist at a distal end, in various instances.

The surgical tool 2118 can be a laparoscopic, endoscopic and/or endoluminal tool, for example, that is capable of performing a procedure on a patient at a surgical site. In some aspects of the present disclosure, the surgical tool 2118 includes a laparoscopic tool, which can be inserted into an incision of a patient. The laparoscopic tool can comprise a rigid, semi-rigid, or flexible shaft. When designed for laparoscopy, the distal end of the shaft can be connected to an end effector that may comprise, for example, a wrist, a grasper, a scissors, a stapler, or other surgical device. Exemplary end effectors for cutting and fastening tissue are further described herein.

In certain aspects of the present disclosure, the surgical tool 2118 comprises an endoscopic surgical tool that is inserted into the anatomy of a patient to capture images of the anatomy (e.g., body tissue). The endoscopic tool, or endoscope, can include a tubular and flexible shaft. The endoscope includes one or more imaging devices (e.g., cameras or sensors) that capture images at the surgical site. The imaging devices may include one or more optical components such as an optical fiber, fiber array, or lens. The optical components move along with the tip of the surgical tool 2118 such that movement of the tip of the surgical tool 2118 results in changes to the images captured by the imaging devices. Exemplary imaging devices and visualization systems are further described herein.

In other instances, the surgical tool 2118 comprises an endoluminal tool, which can be inserted through a natural orifice of a patient, such as a bronchoscope or urethroscope. The endoluminal tool can also include a tubular and flexible shaft. When designed for endoluminal surgery, the distal end of the shaft can be connected to an end effector that may comprise, for example, a wrist, a grasper, scissors, or other surgical device.

The robotic arms 2102 of the robotic surgical system 2100 can manipulate the surgical tool 2118 using elongate movement members. The elongate movement members may include pull-wires, also referred to as pull or push wires, cables, fibers, or flexible shafts. For example, the robotic arms 2102 are configured to actuate multiple pull-wires coupled to the instrument 2118 to deflect, articulate, and/or rotate the tip of the surgical tool 2118. The pull-wires may include both metallic and non-metallic materials such as stainless steel, Kevlar, tungsten, carbon fiber, and the like. In some aspects of the present disclosure, the surgical tool 2118 may exhibit nonlinear behavior in response to forces applied by the elongate movement members. The nonlinear behavior may be based on stiffness and compressibility of the tool 2118, as well as variability in slack or stiffness between different elongate movement members.

Referring still to FIG. 31, the robotic surgical system 2100 also includes a controller 2120, which can be a computer processor, for example. The controller 2120 includes a calibration module 2125, image registration module 2130, and a calibration store 2135. The calibration module 2125 can characterize the nonlinear behavior of the tool using a model with piecewise linear responses along with parameters such as slopes, hysteresis, and dead zone values. The robotic surgical system 2100 can more accurately control the surgical tool 2118 by determining accurate values of the parameters. In some instances, some or all functionality of the controller 2120 is performed outside the robotic surgical system 2100. For example, certain functionalities can be performed on another computer system or server communicatively coupled to the robotic surgical system 2100.

Another surgical robot 2200 is shown in FIG. 32. Various aspects of the surgical robot 2200 are further described in U.S. Pat. No. 10,470,830, titled SYSTEM AND METHODS FOR INSTRUMENT BASED INSERTION ARCHITECTURES, issued Nov. 12, 2019, for example.

The surgical robot 2200 can be incorporated into the robotic surgical system 2100 of FIG. 31 in certain aspects of the present disclosure. The surgical robot 2200 includes one or more robotic arms 2202 each having a tool driver 2217 and a surgical tool 2218 attached thereto. In FIG. 32, the robotic arms 2202 are attached to adjustable rails 2250 coupled to a patient platform 2260 in the form of a bed. In the surgical robot 2200, three robotic arms 2202 are attached to the adjustable rail 2250 on a first side of the patient platform 2260, while two robotic arms 2202 are attached to the adjustable rail 2250 on a second side of the patient platform 2260, thereby providing a system with bilateral arms. The surgical robot 2200 can also include a controller like the controller 2120 (FIG. 31), for example, and can be communicatively coupled to a command console, such that a surgeon's inputs at the command console can be implemented by the surgical robot 2200 via the controller.

FIG. 33 illustrates a perspective view of a tool driver 2300, which is also referred to herein as an IDM. Various aspects of the tool driver 2300 are further described in U.S. Pat. No. 10,470,830, titled SYSTEM AND METHODS FOR INSTRUMENT BASED INSERTION ARCHITECTURES, issued Nov. 12, 2019, for example.

The tool driver 2300 can be used with the robotic surgical system 2100 and with the surgical robot 2200, for example. The tool driver 2300 is configured to attach a surgical tool to a robotic arm in a manner that allows the surgical tool to be continuously rotated, or "rolled", about a longitudinal axis of the surgical tool. The tool driver 2300 includes a base 2302 and a surgical tool holder assembly 2304 coupled to the base 2302. The surgical tool holder assembly 2304 service as tool holder for holding a surgical tool, such as the surgical tool 2118 (FIG. 31) or the surgical tool 2218 (FIG. 32).

The surgical tool holder assembly 2304 further includes an outer housing 2306, a surgical tool holder 2308, an attachment interface 2310, a passage 2312, and a plurality of torque couplers 2314 that have splines 2318. The passage 2312 comprises a through-bore that extends from one face of the tool driver 2300 to an opposing face of the tool driver 2300 along the axis 2316. The tool driver 2300 can be used with a variety of surgical tools, which may include a handle, or housing, and an elongated body, or shaft, and which may be for a laparoscope, an endoscope, or other types of surgical tools. An exemplary surgical tool 2400 is shown in FIG. 34, for example.

The base 2302 removably or fixedly mounts the tool driver 2300 to a robotic surgical arm of a robotic surgical system. In FIG. 33, the base 2302 is fixedly attached to the outer housing 2306 of the surgical tool holder assembly 2304. In alternative instances, the base 2302 is structured to include a platform, which is adapted to rotatably receive the surgical tool holder 2308 on the face opposite from the attachment interface 2310. The platform may include a passage aligned with the passage 2312 to receive the elongated body of the surgical tool and, in some instances, an additional elongated body of a second surgical tool mounted coaxially with the first surgical tool. One or more motors can be housed in the base 2302. For example, the surgical tool holder 2308 can include multiple motors, which are configured to drive, i.e. rotate torque drivers 2314 with a torque and rotary velocity, which can be controlled by the controller, for example.

The surgical tool holder assembly 2304 is configured to secure a surgical tool to the tool driver 2300 and rotate the surgical tool relative to the base 2302. Mechanical and electrical connections are provided from the surgical arm to the base 2302 and then to the surgical tool holder assembly 2304 to rotate the surgical tool holder 2308 relative to the outer housing 2306 and to manipulate and/or deliver power and/or signals from the surgical arm to the surgical tool holder 2308 and ultimately to the surgical tool. Signals may include signals for pneumatic pressure, electrical power, electrical signals, and/or optical signals.

The attachment interface 2310 is a face of the surgical tool holder 2308 that attaches to the surgical tool. The attachment interface 2310 includes a first portion of an attachment mechanism that reciprocally mates with a second portion of the attachment mechanism located on the surgical tool. The attachment interface 2310 is further described in U.S. Pat. No. 10,470,830, titled SYSTEM AND METHODS FOR INSTRUMENT BASED INSERTION ARCHITECTURES, issued Nov. 12, 2019, for example.

Various tools can attach to the tool driver 2300, including tools used for laparoscopic, endoscopic and endoluminal surgery. Tools can include tool-based insertion architectures that reduce the reliance on robotic arms for insertion. In other words, insertion of a surgical tool (e.g., towards a surgical site) can be facilitated by the design and architecture of the surgical tool. For example, in some instances, wherein a tool comprises an elongated shaft and a handle, the architecture of the tool enables the elongated shaft to translate longitudinally relative to the handle along an axis of insertion. Various advantages of tool-based insertion architectures are further described in U.S. Pat. No. 10,470,830, titled SYSTEM AND METHODS FOR INSTRUMENT BASED INSERTION ARCHITECTURES, issued Nov. 12, 2019, which is incorporated by reference herein its entirety.

A surgical tool 2400 having a tool-based insertion architecture is shown in FIG. 34. Various aspects of the surgical tool 2400 are further described in U.S. Pat. No. 10,470,830, titled SYSTEM AND METHODS FOR INSTRUMENT BASED INSERTION ARCHITECTURES, issued Nov. 12, 2019, for example.

The surgical tool 2400 enables a translation of the surgical tool 2400 (e.g., translation of its shaft 2402 and end effector 2412 relative to a tool driver and/or distal end of the robotic arm) along an insertion axis. In such instances, the surgical tool 2400 can be moved along the insertion axis without reliance—or with less reliance—on movement of a robotic arm. The surgical tool 2400 includes an elongated shaft 2402, an end effector 2412 connected to the shaft 2402, and a handle 2420, which may also be referred to as an instrument housing or base, coupled to the shaft 2402. The elongated shaft 2402 comprises a tubular member having a proximal portion 2404 and a distal portion 2406. The elongated shaft 2402 includes one or more channels or grooves along its outer surface. The grooves are configured to receive one or more wires or cables 2430 therethrough. The cables 2430 run along an outer surface of the elongated shaft 2402. In other aspects of the present disclosure, certain cables 2430 can run through the shaft 2402 and may not be exposed. Manipulation of the cables 2430 (e.g., via the tool driver 2300) results in actuation of the end effector 2412, for example.

The end effector 2412 comprises laparoscopic, endoscopic, or endoluminal components, for example, and can be designed to provide an effect to a surgical site. For example, the end effector 2412 can comprise a wrist, grasper, tines, forceps, scissors, clamp, knife, and/or fasteners. Exemplary surgical end effectors are further described herein. The cables 2430 that extend along the grooves on the outer surface of the shaft 2402 can actuate the end effector 2412. The cables 2430 extend from a proximal portion 2404 of the shaft 2402, through the handle 2420, and toward a distal portion 2406 of the shaft 2402, where they actuate the end effector 2412.

The instrument handle 2420 includes an attachment interface 2422 having one or more mechanical inputs 2424, e.g., receptacles, pulleys or spools, that are designed to be reciprocally mated with one or more torque couplers 2314 (FIG. 33) on the attachment interface 2310 of the tool driver 2300. The attachment interface 2422 is capable of attaching to the tool driver 2300 via a front-mount, back-mount and/or top mount. When physically connected, latched, and/or coupled together, the mated mechanical inputs 2424 of the instrument handle 2420 may share axes of rotation with the torque couplers 2314 of the tool driver 2300, thereby allowing the transfer of torque from the motors in the tool driver 2300 to the instrument handle 2420. In some instances, the torque couplers 2314 may comprise splines that are designed to mate with receptacles on the mechanical inputs. Cables 2430 that actuate the end effector 2412 engage the receptacles, pulleys, or spools of the handle 2420, such that the transfer of torque from the tool driver 2300 to the instrument handle 2420 results in actuation of the end effector 2412.

The surgical tool 2400 can include a first actuation mechanism 2450 (FIG. 35) that controls actuation of the end effector 2412. The tool 2400 can also include a second actuation mechanism that enables the shaft 2402 to translate relative to the handle 2420 along an axis of insertion A. In various instances, the first actuation mechanism 2450 can be decoupled from the second actuation mechanism, such that actuation of the end effector 2412 is not affected by the translation of the shaft 2402, and vice versa.

In various instances, an actuation mechanism can include one or more pulleys mounted on a rotary axis to change relative cable length and, in other instances, mounting a pulley on a lever, gear or track-based system to adjust its location. Additionally or alternatively, ball spline rotary shafts that travel down a length of a tool can also be used to transmit forces in a mechanically-remote way. Various actuation mechanisms are further described in U.S. Pat. No. 10,470,830, titled SYSTEM AND METHODS FOR INSTRUMENT BASED INSERTION ARCHITECTURES, issued Nov. 12, 2019, for example.

Referring to FIG. 35, the first actuation mechanism 2450 can provide N+1 wrist motion, wherein N is the number of degrees of freedom provided by N+1 cables. The first actuation mechanism 2450 for actuating the end effector 2412 comprises at least one cable segment 2430 that extends through at least one set of pulleys. In the actuation mechanism of FIG. 35, a first cable, or first cable segment, extends through pulley members 2450a, 2450b, 2450c, while a second cable, or second cable segment, extends through pulley members 2450d, 2450e, 2450f. The cables 2430 are grounded at or near the proximal end 2404 (FIG. 34) of the shaft 2402, then extends through the set of pulleys 2450a, 2450b, 2450c, 2450d, 2450e, 2450f located within the housing 2420, before terminating at or near the end effector 2412. Cable total path length is kept constant by grounding each cable 2430 at or near the proximal end 2404 of the shaft 2402, and relative length changes are made by moving one or more pulleys (e.g., pulley members 2450b and 2450e) relative to each other as indicated by the arrows in FIG. 35, thereby enabling actuation of the end effector 2412. In some instances, the pulleys can be moved via linear or rotary motion of corresponding mechanical inputs 2424. The first actuation mechanism 2450 can permit free movement of the instrument shaft 2402 relative to the actuation pulleys 2450a, 2450b, 2450c, 2450d, 2450e, 2450f thereby allowing an additional cable to be included to permit insertion and retraction of the instrument shaft 1202 at the same time as end effector 1212 actuation.

Robotic surgical tools having tool-based insertion architecture, such as the surgical tool 2400 shown in FIG. 34, for example, may be subjected to high loads during certain surgical actuations or surgical functions. For example, a surgical tool that is used to clamp, cut, staple and/or fasten tissue may be subjected to high clamping and firing loads when clamping certain types of tissue and/or when firing fasteners. In certain instances, the clamping and firing loads on a surgical tool can exceed 300 lbf, for example. The tool-based insertion architecture in the housing of such a surgical tool should be configured to withstand such loads. In certain instances, a lead screw may be used to translate the tool housing along the elongate shaft, which may withstand the high clamping and firing loads. However, a lead screw arrangement may be bulky and/or costly in certain instances.

Alternatively, a translation mechanism that is lightweight, nimble, and/or less expensive than a lead screw may be advantageous in certain instances. Such a translation mechanism can be sufficiently robust to withstand significant forces during use, such as the high forces transmitted during clamping and/or firing, for example. For example, a pulley and cable arrangement can be used in combination with one or more pivoting locks, which are configured to resist the high clamping and/or firing forces.

In one aspect of the present disclosure, a surgical tool can include a surgical end effector comprising opposing jaws, an elongate shaft extending distally to the surgical end effector, and a housing defining a passage therethrough, wherein the elongate shaft extends through the passage. The surgical tool can also include an actuation mechanism configured to selectively move the housing along the elongate shaft relative to the surgical end effector, wherein the actuation mechanism comprises a pulley, a cable engaged with the pulley and a lock arrangement configured to releasably lock the housing relative to the elongate shaft. The lock arrangement can include a washer positioned around the elongate shaft, wherein the cable is engaged with the washer, and wherein the washer is configured to pivot relative to the elongate shaft between a locked orientation and an unlocked orientation. Moreover, an actuation of the pulley can apply a tension to the cable to pivot the washer to the unlocked orientation.

In various instances, such a lock arrangement can also include a second washer positioned around the elongate shaft, wherein an opposite end of the cable is engaged with the second washer, and wherein the second washer is configured to pivot relative to the elongate shaft between a locked orientation and an unlocked orientation.

In certain instances, the foregoing arrangement can securely ground translation of the surgical tool housing along the elongate shaft of the surgical tool without requiring a high mechanical advantage linear motion, such as the linear motion achieved with a lead screw, for example. Moreover, the actuation mechanism for effecting the tool-based translation can be nimble and lightweight, for example.

Referring now to FIG. 36, a surgical tool 2500 is shown. The surgical tool 2500 includes a housing 2520, which is also referred to herein as a handle or tool base, an elongate shaft 2530 slidably positioned through a portion of the housing 2520, and a distal end effector 2512. The housing 2520 can be similar to the housing 2420 (FIG. 34) in many aspects. For example, the housing 2520 can include an attachment interface having one or more mechanical inputs, such as receptacles, pulleys, and/or spools, that are designed to reciprocally mate with one or more torque couplers 2314 (FIG. 33) on the attachment interface 2310 of the tool driver 2300 and to receive actuation motion(s) from a robotic system. One or more actuation mechanisms, such as the actuation mechanism 2550, for example, can be positioned in the housing 2520 and configured to effect one or more surgical actuations, such as articulation, clamping, and/or firing of the end effector 2512.

Translation of the end effector 2512 can be achieved with the actuation mechanism 2570, which includes a pulley arrangement 2572 and a lock arrangement 2584. The pulley arrangement 2572 includes a pulley wheel 2574, a capstan 2576, and a cable 2578 extending from a first end 2580 to a second end 2582. The cable 2578 terminates at the first end 2580 and at the second end 2582. The first end 2580 and the second end 2582 are mounted to features in the housing 2520, which are further described herein. The cable 2578 in FIG. 36 is not a continuous loop. Rather, the cable 2578 comprises a piece of cable with ends 2580, 2582 that are configured to move relative to each other in certain instances to change the length of the cable loop. An actuation of the pulley arrangement 2572 is configured to apply tension to the cable 2578 to exert a pulling force on the housing 2520 along the length of the elongate shaft 2530. For example, rotation of the capstan 2576, applies tension to the cable 2578. When the actuation mechanism 2570 is unlocked, as further described herein, the pulling force on the cable 2578 is configured to pull the housing 2520 along the length of the elongate shaft 2530, such that the end effector 2512 is displaced along the longitudinal axis A of the surgical tool 2500.

The elongate shaft 2530 is grounded at its proximal end 2532 to a component 2502 of the surgical robot, such as a distal end of a robotic arm, which is similar in many aspects to the robotic arm 2102 (FIG. 31) and the robotic arm 2202 (FIG. 32), for example. Similarly, the distal end 2534 of the elongate shaft 2530 is grounded to a distal portion of the surgical tool 2500. More specifically, the distal end 2534 is fixed to a bracket 2514 mounted to the end effector 2512. The housing 2520 is configured to move along the elongate shaft 2530 between the component 2502 and the bracket 2514.

The actuation mechanism 2570 also includes the lock arrangement 2584 in combination with the pulley arrangement 2572. The lock arrangement 2584 is depicted schematically in FIG. 36. The lock arrangement 2584 is configured to releasably lock the housing 2520 to the elongate shaft 2530 such that forces applied to the elongate shaft 2530 during certain surgical actuations and/or functions (e g clamping and/or firing) do not effect longitudinal displacement of the housing 2520 relative to the elongate shaft 2530 and do not move the end effector 2512 along the insertion axis A.

Generally, the end effector 2512 would not be advanced or retracted along the insertion axis, or longitudinal axis of the elongate shaft 2530, during a clamping and/or firing actuation. More specifically, while tissue is being clamped, cut, and/or stapled, for example, the longitudinal position of the end effector 2512 is often fixed, which may avoid damaging and/or traumatizing the tissue in certain instances. To this end, the lock arrangement 2584 can be configured to lock the longitudinal position of the housing 2520 on the elongate shaft 2530 during a clamping and/or firing actuation. When in the locked configuration, any forces transmitted between the housing 2520 and the shaft 2530 can be resisted by the lock arrangement 2584 in order to hold the end effector 2512 stationary relative to the tissue being clamped, transected, and/or stapled, for example.

Referring now to FIG. 37, a surgical tool 2600 is shown. Portions of the surgical tool 2600 are removed from FIG. 37 for clarity. For example, portions of a housing 2620 are removed from FIG. 37. The surgical tool 2600 can be similar in many aspects to the surgical tool 2500. For example, the surgical tool 2600 includes a housing 2620, which is also referred to herein as a handle or tool base, an elongate shaft 2630 slidably positioned through the housing 2620, and a distal end effector 2612. The housing 2620 can be similar to the housing 2420 (FIG. 34) in many aspects. For example, the housing 2620 can include an attachment interface having one or more mechanical inputs, such as receptacles, pulleys, and/or spools, that are designed to reciprocally mate with one or more torque couplers 2314 (FIG. 33) on the attachment interface 2310 of the tool driver 2300, which are configured to receive actuation motion from the robotic system. One or more actuation mechanisms in the housing 2620 can be configured to effect one or more surgical actuations, such as articulation, clamping, and/or firing of the end effector 2612, for example. The housing 2620 can be built around the elongate shaft 2630, for example.

The elongate shaft 2630 extends from the surgical robot to the end effector 2612. For example, a proximal end 2632 of the elongate shaft 2630 is mounted to a robotic arm 2602 of a robotic surgical system, and a distal end 2634 of the elongate shaft 2630 is mounted to a distal flange 2614 of the end effector 2612. The housing 2620 is slidably positioned around the elongate shaft 2630 between the proximal end 2632 and the distal end 2634.

The surgical tool 2600 includes an actuation mechanism 2670 including a pulley arrangement 2672 and a lock arrangement 2684. The pulley arrangement 2672 is similar in many aspects to the pulley arrangement 2572 (FIG. 36) and includes a pulley 2674 mounted to the robotic arm 2602, a capstan 2676 mounted to the flange 2614, and a cable 2678 engaged with the pulley 2674 and the capstan 2676 and extending therebetween. The cable 2678 is mounted to the housing 2620 via the lock arrangement 2684. Moreover, the pulley arrangement 2672 and, more specifically, the cable 2678 thereof, is configured to move the lock arrangement 2684 between the unlocked configuration and the locked configuration.

The lock arrangement 2684 is configured to releasably lock the housing 2620 relative to the elongate shaft 2630. The lock arrangement 2684 includes a first lock 2686 and a second lock 2688. The locks 2686, 2688 are washer-shaped and have a central bore or through-hole, which is configured to receive the elongate shaft 2630 therethrough. In other words, the first lock 2686 and the second lock 2688 are positioned around the elongate shaft 2630 within the housing 2620. A first end 2636 of the cable 2678 is engaged with the first lock 2686 and a second end 2638 of the cable 2678 is engaged with the second lock 2688. The locks 2686, 2688 are configured to pivot relative to the elongate shaft 2630 as they move between a locked orientation and an unlocked orientation. More specifically, an actuation of the pulley arrangement 2672, e.g. rotation of the capstan 2767, is configured to apply a tension to the cable 2678 to pull the ends 2636, 2638 and pivot the locks 2686, 2688 to the unlocked configuration.

In the locked configuration, the first lock 2686 and the second lock 2688 are oriented at an oblique angle relative to a longitudinal axis defined by the elongate shaft 2630. More specifically, an axis extending through the central bore in each lock 2686, 2688 is obliquely-oriented relative to the longitudinal axis of the elongate shaft 2630. In the unlocked configuration, the first lock 2686 and the second lock 2688 are configured to pivot toward a parallel orientation, in which the locks 2686, 2688 are parallel, or nearly parallel with each other. As the locks 2686, 2688 pivot toward the unlocked configuration, the axes extending through the central bore in each lock 2686, 2688 are configured to move into axial alignment with the longitudinal axis of the elongate shaft 2630. The first lock 2686 and the second lock 2688 can be referred to as screen door locks or, collectively, as opposing screen door locks, in certain instances.

The lock arrangement 2684 includes a spring 2690 positioned between the first lock 2686 and the second lock 2688. The spring 2690 biases a portion of the first lock 2686 away from a portion of the second lock 2688, such that the locks 2686, 2688 pivot into an angled orientation relative to the elongate shaft 2630. In various instances, the tension applied by the actuation of the pulley arrangement 2672 is configured to overcome the biasing force of the spring 2690 to move the first lock 2686 and the second lock 2688 from their locked configurations to their unlocked configurations and, thus, to unlock the actuation mechanism 2670 and the lock arrangement 2684 thereof. In such an arrangement, the tension in the cable 2678 first overcomes the lock arrangement 2684 and then pulls on the elongate shaft 2630 to achieve a displacement along the insertion axis A.

Referring still to FIG. 37, the housing 2620 includes a body portion 2622 having an internal cavity 2626, which receives at least a portion of the locks 2686, 2688 and a portion of the elongate shaft 2630. The body portion 2622 includes an internal wall 2624 that defines a portion of the internal cavity. The actuation of the pulley arrangement 2672 is configured to push a portion of the first lock 2686 against the internal wall 2624 to draw or pull the housing 2620 along the elongate shaft 2630. In various instances, when the tension in the cable 2678 is relieved, the spring 2690 is configured to return the locks 2686, 2688 to their locked configurations, in which clamping and firing loads directed to the elongate shaft 2630 are resisted by the lock arrangement 2684.

In various instances, the lock arrangement 2684 can be incorporated into the surgical tool 2500 (FIG. 36). For example, the lock arrangement 2584 (FIG. 36) can include the lock arrangement 2684 or components thereof.

Referring now to a flow chart in FIG. 38, a transection operation 2800 is depicted. Various surgical tools comprising end effectors for transecting tissue are described herein and these various surgical tools and/or robotic surgical systems therefor can utilize the transection operation 2800 to cut tissue and/or fire fasteners. The reader will understand that various control circuits can be utilized to implement the transection operation 2800, including a control circuit, controller, computer processor located in the controller 2120 (FIG. 31) and/or in the control tower 130 (FIG. 1), for example.

An example control circuit 2728 for implementing the transection operation 2800 (FIG. 38) is shown in FIG. 39, for example. The control circuit 2728 includes a processor 2740 in signal communication with a memory 2742, a communication device 2744, a drive system 2752, and inputs 2780, 2782. The processor 2740 includes a clock, or timer, 2741, which is configured to time various stages or sub-stages in the transection operation 2800 (FIG. 38), as further described herein.

The memory 2742 stores program instructions, which are configured to implement various surgical operations, including a clamping operation 2840 and the transection operation 2800 (FIG. 38) or various stages thereof. The memory 2742 also stores various threshold parameters related to transitioning between the stages in the transection operation 2800, such as bailout threshold parameters, for example. Additional parameters stored in the memory 2742 are further described herein.

The communication device 2744 is configured to convey information from the processor 2740 to external devices, such as a graphical user interface (GUI) 2790, for example. Various outputs to the GUI 2790 are further described herein.

The drive system 2752 includes a motor 2758, an input drive 2760 coupled to the motor 2758, a torque sensor 2732, a rotary encoder/position sensor 2736, and a velocity sensor 2738. The drive system 2752 corresponds to a rotary drive in a tool holder or tool drive, as further described herein. The drive system 2752 is configured to provide rotary input to the surgical tool to effect a surgical function. More specifically, the drive system 2752 corresponds to a firing drive system, which is configured to effect a firing motion of the surgical tool. In various instances, the input drive 2760 can correspond to one of the torque couplers 2314 in FIG. 33. For example, output from the motor 2758 can be transferred to a torque coupler 2314 and, ultimately, to a surgical tool to effect the surgical function. More specifically, one of the torque couplers 2314 is configured to transfer output motions from the firing motor 2758 to the surgical tool to effect a firing stroke. The torque sensor 2732 can detect the torque from the firing motor 2758 and/or input drive 2760 coupled thereto, for example, the position sensor 2736 can detect the rotary position of the input drive 2760, for example, and the velocity sensor 2738 can detect the rotary velocity of the input drive 2760, for example.

The control circuit 2728 also includes inputs 2780, 2782, which are configured to convey signals to the processor 2740 indicative of inputs from the surgeon and/or clinician positioned at the command console. In various instances, the input 2780 can correspond to the active/inactive status of a transection input, such as a transection pedal at the command console, for example, and the input 2782 can correspond to the active/inactive status of a clamping input, such as a clamping pedal at the command console, for example.

Referring again to FIG. 38, the transection operation 2800 includes bailout detection, graphical user interface (GUI) prompts and/or alerts, stall detection, and various safety faults, as further described herein. The transection operation 2800 can utilize velocity, torque, and/or position sensors to transition between states and progress through the transition operation 2800. Various sensors in the robot and/or surgical tool can be configured to detect the velocity, torque, and/or position of the input components (e.g. input actuators and/or pedals), rotary drive members (e.g. motors and/or rotary drives in the tool drive and/or the tool base), and of output components (e.g. the firing member and/or cutting edge).

In various instances, the transection operation 2800 may follow a clamping step or clamping operation 2840. During a normal, uninterrupted transection, the transection operation 2800 can proceed from the clamping operation 2840, to an Outset State 2802, to a Pre-Lockout Region State 2804, to a Lockout Region State 2808, to a Transection State 2816, to a Transection-Completed State 2818, to a Retraction State 2830, and finally to a Transection-Ended state 2834. However, the control circuit is configured to monitor various parameters during the transection operation 2800 and certain parameters at certain stages may trigger a variation from the normal, uninterrupted transection operation 2800. For example, torque and/or velocity of the firing member can cause the operation 2800 to detour from the above-summarized flow between the Outset State 2802 and the Transection-Ended state 2834. Additional states in the operation 2800 can include a Pre-Lockout Pause State 2806, a Lockout Pause State 2810, a Lockout-Detected State 2812, a Lockout-Damaged State 2814, a Transection-Canceled State 2820, a Transection Pause State 2822, a Damaged State 2824, a Transection-Stalled State 2826, a Stall Limit State 2828, a Retraction-Stalled State 2832, a Bailout-Attempt State 2836, and/or a Non-Recoverable State 2838, for example.

In various instances, the transection operation 2800 relates to a clinician's activation of the transection input (e.g. a pedal) to transection or cut the tissue clamped between the end effector jaws. Cutting the tissue generally relies on extending a knife or cutting edge distally through clamped tissue. In various aspects of the present disclosure, the transection of tissue is accompanied with nearly simultaneous stapling of tissue. For example, the cutting edge can sever tissue directly following the stapling of the tissue.

In various instances, when a surgical tool is mounted to a robotic arm, the surgical robot can initially implement a homing operation, in which the angular position of the torque couplers and/or rotary inputs are measured and recorded in the memory of the control circuit (e.g. memory 2742) at the various limits or "bumps" in the range of motion of the surgical tool. Homing operations are further described herein and in U.S. patent application Ser. No. 16/553,725, titled ARTICULATING INCLUDING ANTAGONISTIC CONTROLS FOR ARTICULATION AND CALIBRATION, filed Aug. 28, 2019, for example.

After homing and clamping, the transection operation 2800 can commence with entry into the Outset State 2802. Upon entering the Outset State 2802, the control circuit (e.g. the control circuit 2728) can check Condition A, which corresponds to the disablement value (DV) of future firings by the surgical system and/or surgical tool. Condition A is satisfied when the DV stored in the memory (e.g. the memory 2742) is false/negative, which indicates that future firings of the surgical system and/or surgical tool have not been disabled. If Condition A is satisfied, the transection operation 2800 proceeds from the Outset State 2802 to the Pre-Lockout Region State 2804. Alternatively, if the DV is true/positive such that Condition A is not satisfied, future firings have been disabled and the operation 2800 does not proceed from the Outset State 2802. In various instances, if the DV is true/positive, the control circuit can convey the disablement state to a user via the GUI (e.g. the GUI 2790), for example. In various instances, the GUI may be updated throughout the operation 2800. For example, a firing member and/or cutting edge extension function can send updated signals to the GUI throughout the operation 2800 regarding the position and/or status of the cutting edge (e.g. before a lockout region, in the lockout region, in a transection region, at a terminal transection position, and so on).

Upon entry to the Pre-Lockout Region State 2804, a firing motor angle (FMA) from a position sensor (e.g. the position sensor 2736), a firing motor velocity (FMV) from a velocity sensor (e.g. the velocity sensor 2738), and a firing motor torque (FMT) from a torque sensor (e.g. the torque sensor 2732) are set or targeted by the control circuit (e.g. the control circuit 2728). The target FMA corresponds to a terminal transection angle (TTA) at which the firing member has reached a terminal or distal-most position within the end effector. The target FMV corresponds to a pre-lockout region velocity stored in the memory (e.g. the memory 2742). The motor associated with the firing actuation (e.g. the firing motor 2758) is configured to deliver the target FMT. In the Pre-Lockout Region State 2804, the target FMT corresponds to a pre-lockout region operating torque stored in the memory (e.g. the memory 2742). In the Pre-Lockout Region State 2804, if the FMA from the position sensor (e.g. the position sensor 2736) exceeds a threshold non-opening angle associated with a firing member position that prevents unclamping or opening of the jaws, then a non-opening code (NOC) is set to positive/true. The threshold non-opening angle can be recorded during the homing operation, for example, and stored in the memory (e.g. the memory 2742). The NOC corresponds to an inability to open the jaws. In various instances, the NOC can remain positive/true until the operation 2800 proceeds to the Transection-Ended State 2834.

In the Pre-Lockout Region State 2804, the control circuit (e.g. the control circuit 2728) can check for Conditions B and C. Condition B corresponds to the FMA from the position sensor (e.g. the position sensor 2736) being equal to or greater than a minimum cartridge lockout angle, which is stored in the memory (e.g. memory 2742).

In such instances, the FMA can indicate that the firing member has been extended into the lockout region. If Condition B is satisfied during the Pre-Lockout Region State 2804, then the operation 2800 proceeds to the Lockout Region State 2808, which is further described herein.

Condition C corresponds to the inactive status of a transection pedal (e.g. the input 2780). If Condition C is satisfied during the Pre-Lockout Region State 2804, i.e. the transection pedal becomes inactive, then the operation 2800 proceeds to a Pre-Lockout Pause State 2806, which is further described herein.

During the normal, uninterrupted transection, the firing member can be advanced from the pre-lockout region into the lockout region (e.g. satisfying Condition B) without incidence. As a result, the operation 2800 proceeds to Lockout Region State 2808 during which the firing member can traverse the cartridge lockout, for example. The lockout region can correspond to the region in the staple cartridge in which an empty, spent, and/or missing cartridge lockout is positioned. In various instances, the cartridge lockout comprises a mechanical feature in a proximal portion of the end effector and/or cartridge which prevents the cutting edge on the firing member from being advanced distally into tissue when the cartridge (or absence thereof) would not adequately fasten the to-be-transected tissue.

Upon entry to the Lockout Region State 2808, the FMA, FMV, and FMT are set or targeted by the control circuit (e.g. the control circuit 2728). The target FMA can again correspond to the terminal transection angle (TTA). The target FMV corresponds to a lockout region velocity stored in the memory (e.g. memory 2742), which may be different from the pre-lockout region velocity. Moreover, the target FMT corresponds to a lockout region operating torque also stored in the memory (e.g. memory 2742). In the Lockout Region State 2808, if the FMA from a position sensor (e.g. the position sensor 2736) exceeds the threshold non-opening angle associated with a position that prevents unclamping or opening of the jaws, then the NOC (associated with an inability to open the jaws) is set to positive/true.

In the Lockout Region State 2808, the control circuit (e.g. the control circuit 2728) can check for Conditions G, H, I, and J. Condition G corresponds to the FMA from the position sensor (e.g. the position sensor 2736) being equal to or greater than a maximum cartridge lockout angle, which can be determined during a homing operation, for example, and stored in the memory (e.g. memory 2742). In such instances, the firing motor angle can indicate that the firing member has been extended past the lockout region. If Condition G is satisfied during the Lockout Region State 2808, then the operation 2800 proceeds to the Transection State 2816, which is further described herein.

Condition H corresponds to (A) the FMT from the torque sensor (e.g. the torque sensor 2732) being equal to or greater than the lockout region operating torque and (B) the FMV from a velocity sensor (e.g. the velocity sensor 2738) being equal to or less than the lockout region velocity for a period of time exceeding a lockout threshold time stored in the memory (e.g. memory 2742). For example, a high torque from the motor and applied to the firing member may result in minimal or no displacement of the firing member when the lockout is obstructing the firing path in order to prevent transection of unstapled tissue, for example. Condition H indicates that a cartridge lockout has occurred. If Condition H is satisfied during the Lockout Region State 2808, then the operation 2800 proceeds to the Lockout-Detected State 2812, which is further described herein.

Condition I corresponds to the FMT from the torque sensor (e.g. the torque sensor 2732) being equal to or greater than a damaged-lockout threshold torque, which is stored in the memory (e.g. the memory 2742) and can indicate that the cartridge lockout has been damaged. In various instances, the damaged-lockout threshold torque can be greater than the lockout region operating torque. If Condition I is satisfied during the Lockout Region State 2808, then the operation 2800 proceeds to the Lockout-Damaged State 2814.

Condition J corresponds to the inactive status of the transection pedal (e.g. the input 2780). If Condition J is satisfied during the Lockout Region State 2808, i.e. the transection pedal becomes inactive, then the transection operation 2800 proceeds to the Lockout Pause State 2810, which is further described herein.

During the normal, uninterrupted transection, the firing member can be advanced from the lockout region into a transection region (satisfying condition G) without incidence. As a result, the operation 2800 proceeds to the Transection State 2816. Upon entry to the Transection State 2816, a transection count stored in the memory of the control circuit (e.g. the memory 2742 of the control circuit 2728) is incremented up by one. Moreover, the FMA, FMV, and FMT for the Transection State 2816 are set or targeted. The target FMA can again correspond to the terminal transection angle (TTA) and the target FMV can correspond to a transection region velocity stored in the memory (e.g. the memory 2742). In various instances, the transection region velocity can be different than the pre-lockout region velocity and/or the lockout region velocity. The target FMT corresponds to a transection operating torque stored in the memory (e.g. the memory 2742).

In the Transection State 2816, the control circuit (e.g. the control circuit 2728) can check for Conditions N, 0, P, Q and R. Condition N corresponds to the inactive status of the transection pedal (e.g. the input 2780). If Condition N is satisfied during the Transection State 2816, i.e. the transection pedal becomes inactive, then the operation 2800 proceeds to a Transection Pause State 2822, which is further described herein.

Condition O corresponds to the FMT from the torque sensor (e.g. the torque sensor 2732) being equal to or greater than a maximum transection torque, which is stored in the memory (e.g. the memory 2742) and indicates that the firing member (e.g. knife/cutting edge) has been subjected to high torques during the Transection State 2816 and may be damaged. If Condition O is satisfied during the Transection State 2816, the operation 2800 proceeds to the Damaged State 2824, which is further described herein.

Condition P corresponds to both (A) the FMT from the torque sensor (e.g. the torque sensor 2732) being equal to or greater than the transection operating torque and (B) the FMV from a velocity sensor (e.g. the velocity sensor 2738) being equal to or below a stall threshold velocity with both (A) and (B) being true for a time period exceeding a stall threshold time (STT) stored in the memory (e.g. the memory 2742). Condition P can indicate that the firing member, or knife, has stalled during the Transection State 2816. Condition Q corresponds to the number of firing member stalls being equal to or less than a maximum number of firing member stalls, which is stored in the memory (e.g. the memory 2742). If Conditions P and Q are satisfied, the operation 2800 proceeds to the Transection-Stalled State 2826, which is further described herein. If Condition P is satisfied, but Condition Q is not satisfied, the operation 2800 proceeds to a Stall Limit State 2828, which is further described herein and indicates that the surgical device has exceeded the stall limit.

Condition R corresponds to the FMA from the position sensor (e.g. the position sensor 2736) achieving the terminal transection angle (TTA), which indicates the firing member has traveled to the end of the transection or cutline, for example. If Condition R is satisfied, the operation 2800 proceeds to the Transection-Completed State 2818.

During the normal, uninterrupted transection, the firing member can be advanced to the end of the transection region (satisfying condition R) without incidence. As a result, the operation 2800 proceeds to the Transection-Completed State 2818. Upon entry to the Transection-Completed State 2818, the control circuit (e.g. the control circuit 2728) is configured to issue GUI feedback to the GUI (e.g. the GUI 2790) indicating the transection or firing stroke is complete, thus, ready to transition to the Retraction State 2830.

During the normal, uninterrupted transection, the firing member proceeds from the Transection-Completed State 2818 to the Retraction State 2830 without incidence. Upon entry to the Retraction State 2830, a FMA, FMV, FMT are set or targeted by the control circuit (e.g. the control circuit 2728). The target FMA can correspond to an after-homing firing angle, which is stored in the memory (e.g. the memory 2742), and the target FMV can correspond to a retraction velocity, which is also stored in the memory (e.g. the memory 2742). The target FMT can correspond to a retraction operating torque stored in the memory (e.g. the memory 2742). In the retraction state 2830, the control circuit (e.g. the control circuit 2728) can check for Conditions Y and Z.

Condition Y corresponds to both (A) the FMT from the torque sensor (e.g. the torque sensor 2732) being equal to or greater than the retraction operating torque and (B) the FMV from a velocity sensor (e.g. the velocity sensor 2738) being equal to or less than the retraction velocity with both (A) and (B) being true for a time period equal to or greater than the stall threshold time (STT) stored in the memory (e.g. the memory 2742). Condition Y indicates that the firing member has stalled during retraction. If Condition Y is satisfied during the retraction state 2830, the operation 2800 proceeds to the Retraction-Stalled State 2832.

Condition Z corresponds to the FMA from the position sensor (e.g. the position sensor 2736) achieving the after-homing firing angle. Condition Z can indicate that the firing member has returned to its after-homing, pre-firing-stroke angle. If Condition Z is satisfied during the Retraction State 2830, the operation 2800 proceeds to the Transection-Ended State 2834.

Upon entry to the Transection-Ended State 2834, the NOC (associated with the inability to open the jaws) stored in the memory (e.g. the memory 2742) is set to negative/false, which indicates that the firing member has been sufficiently retracted to permit opening or unclamping of the jaws. The operation 2800 then proceeds to the Clamping Operation 2840.

In various instances, the operation 2800 can detour from the Pre-Lockout Region State 2804 to the Pre-Lockout Pause State 2806. From the Pre-Lockout Pause State 2806, the operation 2800 may return to the Pre-Lockout Pause State 2806, or may proceed to the Transection-Cancelled State 2020, or the Bailout Attempt State 2036. Upon entry to the Pre-Lockout Pause State 2806, the control circuit (e.g. the control circuit 2728) is configured to store the FMA from the position sensor (e.g. the position sensor 2736), which corresponds to the pre-lockout pause angle. The control circuit is configured to target the pre-lockout pause angle during the Pre-Lockout Pause State 2806. For example, the pre-lockout pause angle can be held or maintained during the Pre-Lockout Pause State 2806.

In the Pre-Lockout Pause State 2806, the control circuit (e.g. the control circuit 2728) can check for Conditions D, E, and F. Condition D corresponds to the active status of the transection pedal (e.g. the input 2780). If Condition D is satisfied during the Pre-Lockout Pause State 2806, i.e. the transection pedal becomes active, then the operation 2800 returns to the Pre-Lockout Region State 2804, which is further described herein.

Condition E corresponds to the active status of the clamping pedal (e.g. the input 2782). If Condition E is satisfied during the Pre-Lockout Pause State 2806, i.e. the clamping pedal becomes active, then the operation 2800 proceeds to the Transection-Canceled State 2820, which is further described herein.

Condition F corresponds to both (A) the FMT from a torque sensor (e.g. the torque sensor 2732) being equal to or greater than a bailout detection torque and (B) the FMV from a velocity sensor (e.g. the velocity sensor 2738) being equal to or less than a bailout detection velocity with both (A) and (B) being true for a time period equal to or greater than a bailout detection time stored in the memory (e.g. the memory 2742). Condition F can indicate a surgeon or clinician is attempting and/or effecting a bailout step while the firing member moves through the pre-lockout region. For example, during a surgical procedure, the surgeon or clinician can manually manipulate the firing member via a bailout lever or actuator on the housing of the surgical tool, which may involve decoupling the firing member from the firing motor and retracting the firing member manually, for example. If Condition F is satisfied during the Pre-Lockout Pause State 2806, then the transection operation 2800 proceeds to the Bailout-Attempt State 2836, which is further described herein.

In various instances, the operation 2800 can detour from the Lockout Region State 2808 to the Lockout Pause State 2810. From the Lockout Pause State 2810, the operation 2800 may return to the Lockout Region State 2808, or may proceed to the Transection-Canceled State 2020 or the Bailout Attempt State 2036. Upon entry to the Lockout Pause State 2810, the control circuit (e.g. the control circuit 2728) is configured to store the FMA, which corresponds to the lockout pause angle. The control circuit is configured to target the lockout pause angle during the Lockout Pause State 2810. For example, the FMA can be held or maintained during the Lockout Pause State 2810.

In the Lockout Pause State 2810, the control circuit (e.g. the control circuit 2728) can check for Conditions K, L, and M. Condition K corresponds to the active status of the transection pedal (e.g. the input 2780). If Condition K is satisfied during the Lockout Pause State 2810, i.e. the transection pedal becomes active, then the operation 2800 returns to the Lockout Region State 2808, which is further described herein.

Condition L corresponds to the active status of the clamping pedal (e.g. the input 2782). If Condition L is satisfied during the Lockout Pause State 2810, i.e. the clamping pedal becomes active, then the operation 2800 proceeds to the Transection-Canceled State 2820, which is further described herein.

Condition M corresponds to both (A) the FMT from the torque sensor (e.g. the torque sensor 2732) being equal to or greater than the bailout detection torque and (B) the FMV from a velocity sensor (e.g. the velocity sensor 2738) being equal to or less than the bailout detection velocity with both (A) and (B) being true for a time period equal to or greater than the bailout detection time. The bailout detection torque, bailout detection velocity, and bailout detection time are the same threshold values in the Pre-Lockout Pause State 2806. For example, Condition M can be the same as Condition F. In other instances, different bailout threshold values can apply during the Pre-Lockout Pause State 2806 and the Lockout Pause State 2810. Condition M can indicate a surgeon or clinician is attempting and/or effecting a bailout step while the firing member moves through the lockout region. For example, during a surgical procedure, the surgeon or clinician can manually manipulate the firing member, which may involve decoupling the firing member from the firing motor and retracting the firing member manually, for example. If Condition M is satisfied during the Lockout Pause State 2810, then the transection operation 2800 proceeds to the Bailout-Attempt State 2836, which is further described herein.

In various instances, the operation 2800 can detour from the Lockout Region State 2808 to the Lockout-Detected State 2812 and, then, to the Retraction State 2830. Upon entry to the Lockout-Detected State 2812, the control circuit (e.g. the control circuit 2728) is configured to convey determination of the lockout and the locked-out state to a clinician via the GUI (e.g. the GUI 2790), for example. For example, the control circuit can issue an error message informing the clinician that a cartridge is missing and/or that the installed cartridge is empty/spent. From the Lockout-Detected State 2812, the operation 2800 can proceed to the Retraction State 2830, which is further described herein.

In various instances, the operation 2800 can detour from the Lockout Region State 2808 to the Lockout-Damaged State 2814 and, then, to the Retraction State 2830. Upon entry to the Lockout-Damaged State 2814, the control circuit (e.g. the control circuit 2728) is configured to convey a message to the clinician indicating that damage has been detected and the surgical tool is likely damaged or otherwise inoperable. For example, the control circuit can issue an error message via the GUI (e.g. the GUI 2790). Moreover, the control circuit can update the DV to true/positive, which indicates that future firings of the surgical system and/or surgical tool have been disabled. As further described herein, when the DV is true/positive, Condition A is not satisfied and a subsequent operation 2800 would not proceed from the Outset State 2802. From the Lockout-Damaged State 2814, the operation 2800 can proceed to the Retraction State 2830, with is further described herein.

In various instances, the operation 2800 can detour from various states to the Transection-Canceled State 2820 and, then, to the Retraction State 2830. For example, the transection operation 2800 can be canceled and, thus, detour to the Transection-Canceled State 2820 directly from the Pre-Lockout Pause State 2806 (Condition E), the Lockout Pause State 2810 (Condition L), the Transection Pause State 2822 (Condition T), or the Transection-Stalled State 2826 (Condition V). For example, actuation of the clamping operation (e.g. activation of the clamping pedal or other input) can cancel the operation 2800 and the operation can proceed directly to the Transection-Canceled State 2820. Upon entry to the Transection-Canceled State 2820, the control circuit (e.g. the control circuit 2728) is configured to convey a message to the clinician indicating that the transection operation 2800 has been canceled. For example, the control circuit can issue an error message via the GUI (e.g. the GUI 2790). From the Transection-Canceled State 2820, the operation 2800 can proceed to the Retraction State 2830, with is further described herein.

In various instances, the operation 2800 can detour from the Transection State 2816 to the Transection Pause State 2822. For example, deactivation of the clamping pedal or other input during the Transection State 2816 can pause the transection operation 2800. Upon entry to the Transection Pause State 2822, the control circuit (e.g. the control circuit 2728) is configured to store the FMA, which corresponds to the transection pause angle. The control circuit is configured to target the transection pause angle during the Transection Pause State 2822. For example, the transection pause angle can be held or maintained during the Transection Pause State 2822.

In the Transection Pause State 2822, the control circuit (e.g. the control circuit 2728) can check for Conditions S, T, and U. Condition S corresponds to the active status of the transection pedal (e.g. the input 2780). If Condition S is satisfied during the Transection Pause State 2822, i.e. the transection pedal becomes active, then the operation 2800 returns to the Transection State 2816, which is further described herein.

Condition T corresponds to the active status of the clamping pedal (e.g. the input 2782). If Condition T is satisfied during the Transection Pause State 2822, i.e. the clamping pedal becomes active, then the operation 2800 proceeds to the Transection-Canceled State 2820, which is further described herein.

Condition U corresponds to both (A) the FMT from the torque sensor (e.g. the torque sensor 2732) being equal to or greater than the bailout detection torque and (B) the FMV from a velocity sensor (e.g. the velocity sensor 2738) being equal to or less than the bailout detection velocity with both (A) and (B) being true for a time period equal to or greater than the bailout detection time. The bailout detection torque, bailout detection velocity, and bailout detection time are the same threshold values in the Pre-Lockout Pause State 2806 and Lockout Pause State 2810. In other instances, different bailout threshold values can apply during the Pre-Lockout Pause State 2806, the Lockout Pause State 2810, and/or the Transection Pause State 2822. For example, Condition U can be the same as Condition F and/or Condition M. In other instances, different bailout threshold values can apply during the Transection Pause State 2822. Condition U can indicate a surgeon or clinician is attempting and/or effecting a bailout step during a tissue transection step. For example, during a surgical procedure, the surgeon or clinician can manually manipulate the firing member, which may involve decoupling the firing member from the firing motor and retracting the firing member manually, for example. If Condition U is satisfied during the Transection Pause State 2822, then the transection operation 2800 proceeds to the Bailout-Attempt State 2836, which is further described herein.

In various instances, the operation 2800 can detour from the Transection State 2816 to the Damaged State 2824 and, then, to the Retraction State 2830. Detection of a high torque on the firing motor and/or firing member during the Transection State (e.g. Condition O), which is associated with damage to the surgical device, can trigger the detour to the Damaged State 2824. Upon entry to the Damaged State 2824, the control circuit (e.g. the control circuit 2728) is configured to convey a message to the clinician indicating that damage has been suspected and the surgical tool is likely damaged or otherwise inoperable. For example, the control circuit can issue an error message via the GUI (e.g. the GUI 2790). Moreover, the control circuit can update the DV stored in the memory (e.g. the memory 2742) to true/positive, which indicates that future firings of the surgical system and/or surgical tool have been disabled. As further described herein, when the DV is true/positive, Condition A is not satisfied and a subsequent operation 2800 would not proceed from the Outset State 2802. From the Damaged State 2824, the operation 2800 can proceed to the Retraction State 2830, which is further described herein.

In various instances, the operation 2800 can detour from the Transection State 2816 to the Transection-Stalled State 2826. For example, if certain monitored parameters (e.g. FMV and FMT) indicate that the firing member has stalled during the Transection State and the total number of firing member stalls is less than a maximum threshold, the operation 2800 can enter the Transection-Stalled State 2826.

Upon entry to the Transection-Stalled State 2826, a transection-stall count stored in the memory of the control circuit (e.g. the memory 2742 of the control circuit 2728) is incremented up by one. As further described herein, the transection-stall count is compared to a threshold maximum number of firing member stalls stored in the memory for Condition Q in the Transection State 2816. Moreover, the control circuit is configured to convey or communicate the stall and, in certain instances, the transection-stall count, to the clinician. For example, the control circuit can issue GUI feedback via the GUI (e.g. the GUI 2790) indicating the operation 2800 has stalled and, thus, entered the Transection-Stalled State 2826.

Upon entry to the Transection-Stalled State 2826, the control circuit (e.g. the control circuit 2728) is also configured to store the FMA from the position sensor (e.g. the position sensor 2736), which corresponds to the stall angle, and set a timer and/or set a time parameter of an internal clock (e.g. the clock 2741) to the current time, i.e. the time the Transection-Stalled State 2826 was initiated. Moreover, the FMA, MFV and FMT are set or targeted by the control circuit. The target FMA angle can correspond to a back-off angle, and the target FMV can again correspond to the transection region velocity, which is the same target FMV as during the Transection State 2816, in various instances. The target FMT corresponds to the transection operating torque, which is the same target FMT as during the Transection State 2816, in various instances.

In the Transection-Stalled State 2826, the control circuit (e.g. the control circuit 2728) can check for Conditions V, W, and X. Condition V corresponds to the active status of the clamp pedal (e.g. the input 2782). If Condition V is satisfied during the Transection-Stalled State 2826, i.e. the clamp pedal becomes active, then the operation 2800 proceeds to the Transection-Canceled State 2820, which is further described herein.

Condition W corresponds to both (A) the current time minus the recorded time parameter being equal to or greater than a transection back-off time and (B) the transection pedal status (e.g. status of the input 2780) changing from inactive to active. Condition W corresponds to the duration of the stall being less than a threshold time period stored in the memory (e.g. the memory 2742) and the transection pedal returning to an active status. In such instances, Condition W is satisfied, and the operation returns to the Transection State 2816.

Condition X corresponds to both (A) the FMT from the torque sensor (e.g. the torque sensor 2732) begin equal to or greater than the bailout detection torque and (B) the FMV from a velocity sensor (e.g. the velocity sensor 2738) being equal to or less than the bailout detection velocity with both (A) and (B) being true for a time period equal to or greater than the bailout detection time. The bailout detection torque, bailout detection velocity, and bailout detection time are the same threshold values in the Pre-Lockout Pause State 2806, Lockout Pause State 2810, Transection Pause State 2822, and/or the Transection-Stalled State 2826. For example, Condition X can be the same as Condition F, Condition M, and/or Condition U. In other instances, different bailout threshold values can apply during the Transection-Stalled State 2826.

Condition X can indicate a surgeon or clinician is attempting and/or effecting a bailout step while the firing member moves through the lockout region. For example, during a surgical procedure, the surgeon or clinician can manually manipulate the firing member, which may involve decoupling the firing member from the firing motor and retracting the firing member manually, for example. If Condition X is satisfied during the Transection Stalled State 2826, then the transection operation 2800 proceeds to the Bailout-Attempt State 2836, which is further described herein.

In various instances, the operation 2800 can detour from the Transection State 2816 to the Stall Limit State 2828 and then to the Transection-Canceled State 2820. For example, the operation 2800 can proceed to the Stall Limit State 2828 if the various parameters for entering the Transection-Stalled State 2826 are satisfied; however, the surgical tool has exceeded the threshold maximum number of firing member stalls. In other words, the surgical tool has already stalled more times than is reasonable and/or expected. Upon entry to the Stall Limit State 2828, the control circuit (e.g. the control circuit 2728) is configured to convey the determination regarding the stall limit to a clinician via the GUI (e.g. the GUI 2790), for example. In various instances, the control circuit can issue an error message to the GUI informing the clinician that the stall limit has been reached and/or the Stall Limit State 2828 has commenced. From the Stall Limit State 2828, the operation 2800 can proceed to the Retraction State 2830, which is further described herein.

In various instances, the operation can detour from the Retraction State 2830 to the Retraction-Stalled State 2832. For example, the firing member may become stuck or otherwise inoperable by the motor (e.g. the firing motor 2758) during the Retraction State 2830. Upon entry to the Retraction-Stalled State 2832, the control circuit (e.g. the control circuit 2728) can issue a message and/or convey the state of the surgical tool to a clinician or user. For example, the control circuit can convey signals to the GUI (e.g. the GUI 2790), which indicate one or more troubleshooting steps for the clinician. The troubleshooting steps can be configured to remedy a mechanically bound-up surgical tool and/or firing system thereof. The control circuit can also update the DV stored in the memory (e.g. the memory 2742) to true/positive, which indicates that future firings of the surgical system and/or surgical tool have been disabled. As further described herein, when the DV is true/positive, Condition A is not satisfied and a subsequent operation 2800 would not proceed from the Outset State 2802. From the Retraction-Stalled State 2832, the operation 2800 can proceed to the Non-Recoverable State 2838, with is further described herein.

In various instances, the operation 2800 can enter the Bailout-Attempt State 2836 from the Pre-Lockout Pause State 2806, the Lockout Pause State 2810, the Transection Pause State 2822, and/or the Transection-Stalled State 2826. The Bailout-Attempt State 2836 can corresponds to a higher FMT from the torque sensor (e.g. the torque sensor 2732) and lower FMV from a velocity sensor (e.g. the velocity sensor 2738) than during typical advancement and retraction of the firing member, as further described herein. Upon entry to the Bailout-Attempt State 2836, the control circuit (e.g. the control circuit 2728) provides feedback to the clinician regarding how to bailout the surgical device. For example, the control circuit can issue signals to the GUI (e.g. the GUI 2790) indicative of instructions (verbal and/or visual) regarding how to manually extract the surgical device (e g manually retract the firing member such that the jaws can release any tissue clamped therebetween). From the Bailout-Attempt State 2836, the operation can proceed to the Non-Recoverable State 2838.

The operation 2800 can enter the Non-Recoverable State 2838 from the Bailout-Attempt State 2836 and/or the Retraction-Stalled State 2832, for example. The surgical device can be non-recoverable upon entering the Non-Recoverable State 2838. In various instances, the control circuit (e.g. the control circuit 2728) can provide signals to the GUI (e.g. the GUI 2790) regarding the non-recoverable condition of the surgical tool. In such instances, a new clamping operation 2840 and/or a new transection operation 2800 can be prevented. The surgical tool can be retired and/or returned to the manufacturer for inspection and/or repair, in certain instances.

EXAMPLES

Various aspects of the subject matter described herein are set out in the following numbered examples.

Example 1—A surgical tool configured to receive rotary inputs from a robotic surgical system. The surgical tool comprises a distal end effector comprising jaws for clamping tissue therebetween, an intermediate shaft portion coupled to the distal end effector, and a proximal housing coupled to the intermediate shaft portion. The proximal housing comprises an arrangement of rotary drives comprising a first rotary drive. The first rotary drive comprises an input shaft configured to receive a rotary input from the robotic surgical system, a transition nut slidably positioned on the input shaft, and an output gear. The first rotary drive further comprises a high-speed gear configured to selectively drive the output gear, a high-torque gear configured to selectively drive the output gear, and a spring arrangement configured to bias the transition nut along the input shaft from a high-speed operating state, in which the transition nut is in driving engagement with the high-speed gear, to a high-torque operating state, in which the transition nut is in driving engagement with the high-torque gear upon obtaining a threshold torque.

Example 2—The surgical tool of Example 1, wherein the transition nut comprises a perimeter, a first end, and an array of sloping teeth around the perimeter extending to the first end.

Example 3—The surgical tool of Example 2, wherein the high-torque gear comprises an array of complementary sloping receptacles configured to receive the array of sloping teeth when the transition nut is in the high-torque operating state.

Example 4—The surgical tool of Examples 1, 2, or 3, wherein the transition nut further comprises a second end, and a first array of teeth around the perimeter extending to the second end.

Example 5—The surgical tool of Example 4, further comprising a grasping gear drivingly engaged with the high-speed gear, wherein the grasping gear comprises a second array of teeth configured to receive the first array of teeth when the transition nut is in the high-speed operating state.

Example 6—The surgical tool of Example 5, wherein the spring arrangement comprises a first spring configured to bias the first array of teeth toward the second array of teeth.

Example 7—The surgical tool of Examples 1, 2, 3, 4, 5, or 6, wherein the spring arrangement further comprises a second spring configured to bias the first end of the transition nut away from the second end of the transition nut.

Example 8—The surgical tool of Examples 1, 2, 3, 4, 5, 6, or 7, further comprising an output shaft drivingly coupled to the output gear, wherein the output shaft is configured to drive a rotary drive screw to effect a closure of the jaws.

Example 9—The surgical tool of Examples 1, 2, 3, 4, 5, 6, 7, or 8, wherein the first rotary drive further comprises a gear train comprising the high-speed gear, and wherein the gear train comprises a speed ratio greater than one.

Example 10—A surgical tool for a robotic surgical system. The surgical tool comprises a distal end effector comprising jaws for clamping tissue therebetween, an intermediate shaft portion coupled to the distal end effector, and a proximal housing coupled to the intermediate shaft portion. The proximal housing comprises an input shaft configured to receive a rotary input from the robotic surgical system, a transition nut slidably positioned on the input shaft, and an output gear. The proximal housing further comprises a first rotary drive configured to selectively drive the output gear, a second rotary drive configured to selectively drive the output gear, and a spring arrangement configured to bias the transition nut along the input shaft to couple the input shaft with either the first rotary drive or the second rotary drive based on a threshold torque applied to the transition nut.

Example 11—The surgical tool of Example 10, wherein the transition nut rotates with the input shaft.

Example 12—The surgical tool of Examples 10 or 11, wherein the spring arrangement comprises a first spring configured to bias the transition nut out of engagement with the second rotary drive and into engagement with the first rotary drive when the threshold torque is exceeded.

Example 13—The surgical tool of Examples 10, 11, or 12, wherein the transition nut comprises a perimeter, a first end, and an array of sloping teeth around the perimeter extending to the first end. The transition nut further comprises a second end, a first array of teeth around the perimeter extending to the second end, and a second spring configured to bias the first end away from the second end.

Example 14—The surgical tool of Example 13, wherein the first rotary drive comprises a high-torque gear comprising complementary sloping receptacles configured to receive the array of sloping teeth when the input shaft is engaged with the first rotary drive, and wherein the surgical tool is in a high-torque operating state when the first rotary drive is engaged with the input shaft.

Example 15—The surgical tool of Examples 13 or 14, wherein the second rotary drive comprises a high-speed gear and a grasping gear drivingly engaged with the high-speed gear, wherein the grasping gear comprises a second array of teeth configured to receive the first array of teeth when the input shaft is engaged with the second rotary drive, and wherein the surgical tool is in a high-speed operating state when the second rotary drive is engaged with the input shaft.

Example 16—The surgical tool of Examples 10, 11, 12, 13, 14, or 15, wherein the second rotary drive further comprises a gear train comprising the high-speed gear, and wherein the gear train comprises a speed ratio greater than one.

Example 17—The surgical tool of Examples 10, 11, 12, 13, 14, 15, or 16, further comprising an output shaft drivingly coupled to the output gear, wherein the output shaft is configured to drive a rotary drive screw to effect a closure of the jaws.

Example 18—A rotary drive system for rotating a drive screw in a robotic surgical tool. The rotary drive system comprises an input shaft configured to receive a rotary input from a robotic surgical system, a transition nut slidably positioned on the input shaft, and an output gear drivingly coupled to an output shaft. The rotary drive system further comprises a first rotary drive configured to selectively drive the output gear, a second rotary drive configured to selectively drive the output gear, and a spring arrangement configured to bias the transition nut along the input shaft into engagement with either the first rotary drive or the second rotary drive based on a threshold torque applied to the transition nut.

Example 19—The rotary drive system of Example 18, wherein the first rotary drive comprises a high-torque gear that comprises complementary sloping receptacles configured to receive an array of sloping teeth on the transition nut when the input shaft is engaged with the first rotary drive.

Example 20—The rotary drive system of Examples 18 or 19, wherein the second rotary drive comprises a high-speed gear and a grasping gear drivingly engaged with the high-speed gear, wherein the grasping gear comprises an array of teeth configured to engage the transition nut when the input shaft is engaged with the second rotary drive.

Example 21—A robotic surgical system that comprises a closure system. The closure system comprises a first pinion drivingly coupled to a first motor, a second pinion drivingly coupled to a second motor, and a closure gear selectively driven by the first pinion and the second pinion. The robotic surgical system further comprises a control circuit configured to implement a motor crosscheck operation. The control circuit is configured to receive a first parameter indicative of a first torque generated by the first motor, receive a second parameter indicative of a second torque generated by the second motor, compare the first parameter to the second parameter, and transmit a signal to a communication device, wherein the signal is based on the comparison and indicative of a status of the closure system.

Example 22—The robotic surgical system of Example 21, wherein the control circuit is further configured to determine when the closure system has achieved a steady state in the motor crosscheck operation, and compare the first parameter to the second parameter after the closure system has achieved the steady state.

Example 23—The robotic surgical system of Examples 21 or 22, wherein the first pinion and the second pinion simultaneously drive the closure gear to effect a closure stroke.

Example 24—The robotic surgical system of Examples 21, 22, or 23, wherein the status transmitted by the control circuit corresponds to a fault state when the comparison of the first parameter to the second parameter exceeds a threshold value.

Example 25—The robotic surgical system of Example 24, wherein the robotic surgical system is configured to implement a lockout when the status corresponds to the fault state.

Example 26—The robotic surgical system of Examples 21, 22, 23, 24, or 25, wherein, to implement the motor crosscheck operation, the first motor is configured to drive the closure gear in a first direction, and wherein the second motor is configured to drive the closure gear in a second direction opposite to the first direction.

Example 27—The robotic surgical system of Examples 21, 22, 23, 24, 25, or 26, wherein the first motor is configured to transfer torque to the second pinion.

Example 28—The robotic surgical system of Examples 21, 22, 23, 24, 25, 26, or 27, wherein the second motor is configured to transfer torque to the first pinion.

Example 29—The robotic surgical system of Examples 21, 22, 23, 24, 25, 26, 27, or 28, wherein the second pinion is configured to move through a backlash region prior to the closure system achieving a steady state.

Example 30—The robotic surgical system of Example 29, wherein the control circuit is further configured to record a duration of the backlash region and obtain the duration to a stored value.

Example 31—A non-transitory computer readable medium storing computer readable instructions which, when executed, cause a machine to receive a first parameter indicative of a first torque generated by a first motor of a closure system, receive a second parameter indicative of a second torque generated by a second motor of the closure system, and implement a motor crosscheck. The first motor and the second motor are configured to concurrently drive a closure gear. The motor crosscheck comprises compare the first parameter to the second parameter, and transmit a signal to a communication device, wherein the signal is based on the comparison and indicative of a status of the closure system.

Example 32—The non-transitory computer readable medium storing computer readable instructions of Example 31, which, when executed, further cause the machine to determine when the closure system has achieved a steady state, and compare the first parameter to the second parameter after the closure system has achieved the steady state.

Example 33—The non-transitory computer readable medium storing computer readable instructions of Examples 31 or 32, which, when executed, further cause the machine to enter a fault state when the comparison of the first parameter to the second parameter exceeds a threshold value.

Example 34—The non-transitory computer readable medium storing computer readable instructions of Example 33, which, when executed, further cause the machine to implement a lockout state when the status corresponds to the fault state.

Example 35—A robotic surgical system that comprises a closure system. The closure system comprises a first pinion drivingly coupled to a first motor, a second pinion drivingly coupled to a second motor, and a closure gear selectively driven by the first pinion and the second pinion. The closure system further comprises a processor and a memory coupled to the processor. The memory storing instructions executable by the processor to receive a first parameter indicative of a first torque from the first motor, receive a second parameter indicative of a second torque from the second motor, and receive a third parameter indicative of a first angular displacement of the first motor. The memory further stores instructions executable by the processor to receive a fourth parameter indicative of a second angular displacement of the second motor, and determine a status of the closure system based on the first parameter, the second parameter, the third parameter, and the fourth parameter. The memory further stores instructions executable by the processor to transmit a signal to a communication device indicative of the status of the closure system.

Example 36—The robotic surgical system of Example 35, wherein the memory further stores instructions executable by the processor to implement a motor crosscheck in which the first pinion and the second pinion are rotated in opposite directions.

Example 37—The robotic surgical system of Example 35, wherein the memory further stores instructions executable by the processor to implement a motor crosscheck in which the first pinion is driven by the first motor and the second pinion is not driven by the second motor.

Example 38—The robotic surgical system of Examples 35, 36 or 37, wherein the memory further stores instructions executable by the processor to measure a backlash angle during the motor crosscheck, and compare the backlash angle to a backlash value stored in the memory.

Example 39—The robotic surgical system of Examples 35, 36, 37, or 38, wherein the memory further stores instructions executable by the processor to implement a motor crosscheck in which a stiffness of the first pinion is computed from the first torque and the first angular displacement, and the stiffness is compared to a threshold.

Example 40—The robotic surgical system of Examples 35, 36, 37, 38, or 39, wherein the memory stores instructions executable by the processor to implement a motor crosscheck after at least one of a homing operation or clamping event by the closure system.

Example 41—A control circuit for use with a robotic surgical system. The control circuit is configured to receive a parameter indicative of a rotary position of an articulation motor. The articulation motor is configured to drive an articulation joint of a robotic surgical tool, wherein the articulation motor is configured to move through a first range of positions and a second range of positions. The first range of positions and the second range of positions are non-overlapping. The control circuit is further configured to implement a first operating state, and implement a second operating state when the parameter corresponds to a transition of the articulation motor from the first range of positions to the second range of positions. The second operating state is different than the first operating state. The control circuit is further configured to re-implement the first operating state when the parameter corresponds to a return of the articulation motor from the second range of positions into the first range of positions by a threshold anti-dither angle.

Example 42—The control circuit of Example 41, wherein the first range of positions and the second range of positions are contiguous.

Example 43—The control circuit of Examples 41 or 42, wherein the second range of positions comprises an upper mechanical limit of the articulation joint.

Example 44—The control circuit of Examples 41, 42, or 43, wherein a maximum allowable speed of the articulation motor is less in the second operating state than in the first operating state when the parameter is moving away from the first range of positions.

Example 45—The control circuit of Examples 41, 42, 43, or 44, wherein a maximum allowable torque of the articulation motor is less in the second operating state than in the first operating state when the parameter is moving away from the first range of positions.

Example 46—The control circuit of Examples 41, 42, or 43, wherein a maximum allowable speed and a maximum allowable torque of the articulation motor is less in the second operating state than in the first operating state when the parameter is moving away from the first range of positions.

Example 47—The control circuit of Examples 41, 42, 43, 44, 45, or 46, wherein the parameter comprises a first parameter indicative of a rotary position of a first articulation motor, and wherein the control circuit is further configured to receive a second parameter indicative of a second rotary position of a second articulation motor, wherein the second articulation motor is configured to drive the articulation joint of the robotic surgical tool, wherein the second articulation motor is configured to move through a third range of positions and a fourth range of positions, and wherein the third range of positions and the fourth range of positions are non-overlapping.

Example 48—The control circuit of Example 47, wherein the control circuit is further configured to implement a third operating state when the second parameter corresponds to a transition of the second articulation motor from the third range of positions to the fourth range of positions, wherein the third operating state is different than the first operating state. The control circuit is further configured to re-implement the first operating state when the second parameter corresponds to a return of the second articulation motor from the fourth range of positions into the third range of positions by a threshold anti-dither angle.

Example 49—The control circuit of Examples 47 or 48, wherein the fourth range of positions comprises a lower mechanical limit of the articulation joint.

Example 50—A non-transitory computer readable medium storing computer readable instructions which, when executed, cause a machine to receive a first parameter indicative of a rotary position of a first articulation motor, receive a second parameter indicative of a rotary position of a second articulation motor, and implement a first operating state. The non-transitory computer readable medium storing computer readable instructions which, when executed, further cause a machine to transition from the first operating state to a second operating state when the first parameter corresponds to a transition of the first articulation motor from a first range of positions to an upper range of positions, wherein the second operating state is different than the first operating state. The non-transitory computer readable medium storing computer readable instructions which, when executed, further cause a machine to return to the first operating state from the second operating state when the first parameter corresponds to a return of the first articulation motor from the upper range of positions into the first range of positions by a first anti-dither angle. The non-transitory computer readable medium storing computer readable instructions which, when executed, further cause a machine to implement a third operating state when the second parameter corresponds to a transition of the second articulation motor from a second range of positions to a lower range of positions, wherein the third operating state is different than the first operating state. The non-transitory computer readable medium storing computer readable instructions which, when executed, further cause a machine to return to the first operating state from the third operating state when the second parameter corresponds to a return of the second articulation motor from the lower range of positions into the second range of positions by a second anti-dither angle.

Example 51—A robotic surgical tool that comprises a housing, an end effector, and an elongate shaft extending distally from the housing to the end effector. The robotic surgical tool further comprises an articulation joint configured to articulate the end effector relative to the elongate shaft during an articulation motion, an internal shaft extending distally from the housing through the elongate shaft, and an articulation drive system. The articulation drive system comprises an articulation yoke coupled to the internal shaft, an articulation band coupled to the articulation yoke and extending distally along the internal shaft to the articulation joint, and rolling elements intermediate the internal shaft and the articulation yoke, wherein the articulation yoke is configured to roll along the rolling elements during the articulation motion.

Example 52—The robotic surgical tool of Example 51, wherein the rolling elements are positioned around the circumference of the internal shaft.

Example 53—The robotic surgical tool of Examples 51 or 52, further comprises a rolling element pad. The rolling element pad comprises a base secured to the internal shaft, a retainer secured to the base, wherein the base and the retainer form a continuous loop track therebetween. The rolling element pad further comprises the rolling elements, wherein the rolling elements comprise spheres positioned in the continuous loop track.

Example 54—The robotic surgical tool of Example 53, wherein the retainer comprises a window, and wherein a set of the rolling elements protrude through the window and contact the articulation yoke.

Example 55—The robotic surgical tool of Examples 53 or 54, wherein the rolling element pad is press-fit into a recess in the internal shaft.

Example 56—The robotic surgical tool of Examples 53, 54, or 55, wherein the continuous loop track comprises a first continuous loop track, and wherein the base and the retainer form a second continuous loop track configured to receive a plurality of the rolling elements therein.

Example 57—The robotic surgical tool of Example 56, wherein the articulation yoke comprises a first articulation yoke configured to slidably engage the rolling elements positioned in the first continuous loop track during the articulation motion, wherein the articulation drive system further comprises a second articulation yoke coupled to the internal shaft at a location distal to the first articulation yoke, and wherein the second articulation yoke is configured to slidably engage the rolling elements positioned in the second continuous loop track during the articulation motion.

Example 58—The robotic surgical tool of Example 57, wherein the articulation band comprises a first articulation band attached to the first articulation yoke and extending along the internal shaft to the articulation joint, and wherein the articulation drive system further comprises a second articulation band attached to the second articulation yoke and extending along the internal shaft to the articulation joint.

Example 59—The robotic surgical tool of Examples 57 or 58, wherein the articulation drive system is configured to move the first articulation yoke and second articulation yoke relative to each other and along the internal shaft to effect the articulation motion.

Example 60—A surgical tool that comprises a surgical end effector comprising opposing jaws, an elongate shaft extending distally to the surgical end effector, and a housing defining a passage therethrough, wherein the elongate shaft extends through the passage. The surgical tool further comprises an actuation mechanism configured to selectively move the housing along the elongate shaft relative to the surgical end effector. The actuation mechanism comprises a pulley, a cable engaged with the pulley, and a lock arrangement configured to releasably lock the housing relative to the elongate shaft. The lock arrangement comprises a washer positioned around the elongate shaft. The cable is engaged with the washer. An actuation of the pulley is configured to apply a tension to the cable to pivot the washer relative to the elongate shaft from a locked orientation to an unlocked orientation.

Example 61—The surgical tool of Example 60, wherein the washer comprises a first washer, wherein the lock arrangement further comprises a second washer positioned around the elongate shaft, wherein the cable is engaged with the second washer, and wherein the second washer is configured to pivot relative to the elongate shaft between a locked orientation and an unlocked orientation.

Example 62—The surgical tool of Example 61, wherein, in their locked orientations, the first washer and the second washer are obliquely-oriented relative to a longitudinal axis of the elongate shaft, and wherein the first washer and the second washer are configured to pivot toward a parallel orientation when they move to their unlocked orientations.

Example 63—The surgical tool of Examples 61 or 62, wherein the lock arrangement further comprises a spring between the first washer and the second washer, and wherein the spring biases a portion of the first washer away from a portion of the second washer.

Example 64—The surgical tool of Example 63, wherein the tension applied by the actuation of the pulley is configured to overcome a biasing force of the spring to move the first washer and the second washer from their locked orientations to their unlocked orientations.

Example 65—The surgical tool of Examples 61, 62, 63, or 64, wherein the tension in the cable applied by the actuation of the pulley is configured to pivot the first washer and second washer to the unlocked orientation and then pull on the elongate shaft to move the housing along the elongate shaft.

Example 66—The surgical tool of Examples 60, 61, 62, 63, 64, or 65, wherein the housing comprises a body comprising an internal wall, wherein the internal wall defines a portion of an internal cavity in the body, and wherein the washer extends at least partially into the internal cavity.

Example 67—The surgical tool of Example 68, wherein the actuation of the pulley is configured to push the washer against the internal wall to draw the housing along the elongate shaft.

Example 68—The surgical tool of Examples 60, 61, 62, 63, 64, 65, 66, or 67, wherein the surgical end effector further comprises a firing member configured to cut tissue positioned between the opposing jaws.

Example 69—The surgical tool of Examples 60, 61, 62, 63, 64, 65, 66, 67, or 68, wherein the surgical end effector further comprises a staple cartridge comprising staples.

Example 70—A surgical tool that comprises a surgical end effector, an elongate shaft extending distally to the surgical end effector, and a housing defining a passage therethrough, wherein the elongate shaft extends through the passage. The surgical tool further comprises an actuation mechanism configured to selectively move the housing along the elongate shaft relative to the surgical end effector. The actuation mechanism comprises a pulley, a capstan, and a cable engaged with the pulley and the capstan. The actuation mechanism further comprises a lock arrangement configured to releasably lock the housing relative to the elongate shaft. The lock arrangement comprising a first washer positioned around the elongate shaft. A first end of the cable is engaged with the first washer. The first washer is configured to pivot relative to the elongate shaft between a locked orientation and an unlocked orientation. The lock arrangement further comprising a second washer positioned around the elongate shaft. A second end of the cable is engaged with the second washer. The second washer is configured to pivot relative to the elongate shaft between a locked orientation and an unlocked orientation. The lock arrangement further comprising a spring between the first washer and the second washer, wherein the spring is configured to bias a portion of the first washer away from a portion of the second washer to pivot the first washer and second washer into the locked orientations. A rotation of the capstan is configured to apply a tension to the cable to pivot the first washer and second washer to their unlocked orientations.

Example 71—The surgical tool of Example 70, wherein, in the locked orientations, the first washer and the second washer are obliquely-oriented relative to a longitudinal axis of the elongate shaft, and wherein the first washer and the second washer are configured to pivot toward parallel from their locked orientations to their unlocked orientations.

Example 72—The surgical tool of Examples 70 or 71, wherein the tension applied by the rotation of the capstan is configured to overcome the biasing force of the spring to move the first washer and the second washer from their locked orientations to their unlocked orientations.

Example 73—The surgical tool of Examples 70, 71, or 72, wherein the housing comprises a body comprising an internal wall, wherein the internal wall defines a portion of an internal cavity in the body, and wherein the first washer extends at least partially into the internal cavity.

Example 74—The surgical tool of Example 73, wherein the rotation of the capstan is configured to push the first washer against the internal wall to draw the housing along the elongate shaft.

Example 75—The surgical tool of Examples 70, 71, 72, 73, or 74, wherein the tension in the cable applied by the rotation of the capstan is configured to pivot the first washer and second washer to their unlocked orientations and pull the housing along the elongate shaft.

Example 76—A surgical tool that comprises an elongate shaft, and a housing defining a passage therethrough, wherein the elongate shaft extends through the passage. The surgical tool further comprises an actuation mechanism configured to selectively move the housing along the elongate shaft. The actuation mechanism comprises a pulley arrangement, and a lock arrangement configured to releasably lock the housing relative to the elongate shaft. The lock arrangement comprises a lock positioned around the elongate shaft. An actuation of the pulley arrangement is configured to move the lock from a locked orientation to an unlocked orientation.

Example 77—The surgical tool of Example 76, wherein the lock is configured to pivot from the locked orientation to the unlocked orientation.

Example 78—The surgical tool of Examples 76 or 77, wherein, in the locked orientation, the lock is obliquely-oriented relative to a longitudinal axis of the elongate shaft.

Example 79—The surgical tool of Examples 76, 77, or 78, wherein the lock arrangement further comprises a spring configured to bias the lock toward the locked orientation.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical tool configured to receive rotary inputs from a robotic surgical system, the surgical tool comprising:
   a distal end effector comprising jaws for clamping tissue therebetween;
   an intermediate shaft portion coupled to the distal end effector; and
   a proximal housing coupled to the intermediate shaft portion, the proximal housing comprising an arrangement of rotary drives comprising a first rotary drive, the first rotary drive comprising:
      an input shaft configured to receive a rotary input from the robotic surgical system to effect rotation of the input shaft about a rotation axis;
      a transition nut rotatably driven by the input shaft about the rotation axis, wherein the transition nut is slidably positioned on the input shaft;
      an output gear;
      a high-speed gear configured to selectively drive the output gear;
      a high-torque gear configured to selectively drive the output gear; and
      a spring configured to apply a spring force to bias the transition nut along the input shaft toward a high-speed operating state, in which the transition nut is in driving engagement with the high-speed gear, wherein the application of a threshold torque to the transition nut is configured to overcome the spring force to move the transition nut toward a high-torque operating state, in which the transition nut is in driving engagement with the high-torque gear.

2. The surgical tool of claim 1, wherein the transition nut comprises:
   a perimeter;
   a first end; and
   an array of sloping teeth around the perimeter extending to the first end.

3. The surgical tool of claim 2, wherein the high-torque gear comprises an array of complementary sloping receptacles configured to receive the array of sloping teeth when the transition nut is in the high-torque operating state.

4. The surgical tool of claim 3, wherein the transition nut further comprises:
   a second end; and
   a first array of teeth around the perimeter extending to the second end.

5. The surgical tool of claim 4, further comprising a grasping gear drivingly engaged with the high-speed gear, wherein the grasping gear comprises a second array of teeth configured to receive the first array of teeth when the transition nut is in the high-speed operating state.

6. The surgical tool of claim 5, wherein the spring is configured to bias the first array of teeth toward the second array of teeth.

7. The surgical tool of claim 6, further comprising a second spring configured to bias the first end of the transition nut away from the second end of the transition nut.

8. The surgical tool of claim 1, further comprising an output shaft drivingly coupled to the output gear, wherein the output shaft is configured to drive a rotary drive screw to effect a closure of the jaws.

9. The surgical tool of claim 1, wherein the first rotary drive further comprises a gear train comprising the high-speed gear, and wherein the gear train comprises a speed ratio greater than one.

10. A surgical tool for a robotic surgical system, the surgical tool comprising:
    a distal end effector comprising jaws for clamping tissue therebetween;
    an intermediate shaft portion coupled to the distal end effector; and
    a proximal housing coupled to the intermediate shaft portion, the proximal housing comprising:
       an input shaft configured to receive a rotary input from the robotic surgical system to effect rotation of the input shaft about a rotation axis;
       a transition nut slidably positioned on the input shaft along an axis;
       an output gear;
       a first rotary drive configured to selectively drive the output gear;
       a second rotary drive configured to selectively drive the output gear; and
       a spring axially aligned with the rotation axis and configured to bias the transition nut along the input shaft to couple the input shaft with either the first rotary drive or the second rotary drive based on a threshold torque applied to the transition nut.

11. The surgical tool of claim 10, wherein the transition nut rotates with the input shaft.

12. The surgical tool of claim 11, wherein the spring is configured to apply a spring force to bias the transition nut toward the second rotary drive, wherein the application of the threshold torque to the transition nut is configured to overcome the spring force to move the transition nut out of engagement with the second rotary drive.

13. The surgical tool of claim 12, wherein the transition nut comprises:
    a perimeter;
    a first end;
    an array of sloping teeth around the perimeter extending to the first end;
    a second end;
    a first array of teeth around the perimeter extending to the second end; and
    a second spring configured to bias the first end away from the second end.

14. The surgical tool of claim 13, wherein the first rotary drive comprises a high-torque gear comprising complementary sloping receptacles configured to receive the array of sloping teeth when the input shaft is engaged with the first rotary drive, and wherein the surgical tool is in a high-torque operating state when the first rotary drive is engaged with the input shaft.

15. The surgical tool of claim 13, wherein the second rotary drive comprises a high-speed gear and a grasping gear drivingly engaged with the high-speed gear, wherein the grasping gear comprises a second array of teeth configured to receive the first array of teeth when the input shaft is engaged with the second rotary drive, and wherein the surgical tool is in a high-speed operating state when the second rotary drive is engaged with the input shaft.

16. The surgical tool of claim 15, wherein the second rotary drive further comprises a gear train comprising the high-speed gear, and wherein the gear train comprises a speed ratio greater than one.

17. The surgical tool of claim 10, further comprising an output shaft drivingly coupled to the output gear, wherein the output shaft is configured to drive a rotary drive screw to effect a closure of the jaws.

18. A rotary drive system for rotating a drive screw in a robotic surgical tool, the rotary drive system comprising:
an input shaft configured to receive a rotary input from a robotic surgical system to effect rotation of the input shaft about a rotation axis;
a transition nut slidably positioned on the input shaft;
an output gear drivingly coupled to an output shaft;
a first rotary drive configured to selectively drive the output gear in a first operating state;
a second rotary drive configured to selectively drive the output gear in a second operating state; and
a spring configured to apply a spring force along the rotation axis to bias the transition nut along the input shaft into engagement with the first rotary drive, wherein the application of a threshold torque to the transition nut is configured to overcome the spring force to move the transition nut into engagement with the second rotary drive.

19. The rotary drive system of claim 18, wherein the first rotary drive comprises a high-torque gear that comprises complementary sloping receptacles configured to receive an array of sloping teeth on the transition nut when the input shaft is engaged with the first rotary drive.

20. The rotary drive system of claim 19, wherein the second rotary drive comprises a high-speed gear and a grasping gear drivingly engaged with the high-speed gear, wherein the grasping gear comprises an array of teeth configured to engage the transition nut when the input shaft is engaged with the second rotary drive.

\* \* \* \* \*